US012528823B2

(12) United States Patent
Wasmuth

(10) Patent No.: US 12,528,823 B2
(45) Date of Patent: Jan. 20, 2026

(54) INHIBITORS OF ALDOSE REDUCTASE

(71) Applicant: Applied Therapeutics, Inc., New York, NY (US)

(72) Inventor: Andrew Wasmuth, New York, NY (US)

(73) Assignee: Applied Therapeutics, Inc., New York, NY (US)

( * ) Notice: Subject to any disclaimer, the term of this patent is extended or adjusted under 35 U.S.C. 154(b) by 928 days.

(21) Appl. No.: 17/489,022

(22) Filed: Sep. 29, 2021

(65) Prior Publication Data

US 2022/0017535 A1 Jan. 20, 2022

Related U.S. Application Data

(63) Continuation of application No. PCT/US2020/025928, filed on Mar. 31, 2020.

(60) Provisional application No. 62/827,362, filed on Apr. 1, 2019, provisional application No. 62/928,735, filed on Oct. 31, 2019.

(51) Int. Cl.

| | |
|---|---|
| ***C07D 495/04*** | (2006.01) |
| ***A61P 9/00*** | (2006.01) |
| ***C07H 15/26*** | (2006.01) |

(52) U.S. Cl.

CPC .............. *C07D 495/04* (2013.01); *A61P 9/00* (2018.01); *C07H 15/26* (2013.01)

(58) Field of Classification Search

CPC ....... A61P 9/00; C07D 487/04; C07D 495/04; C07H 15/26

See application file for complete search history.

(56) References Cited

U.S. PATENT DOCUMENTS

| | | | |
|---|---|---|---|
| 4,868,301 A | 9/1989 | Mylari et al. | |
| 4,939,140 A | 7/1990 | Larson et al. | |
| 4,954,629 A | 9/1990 | Mylari et al. | |
| 4,996,204 A | 2/1991 | Mylari et al. | |
| 5,155,259 A | 10/1992 | Suzuki et al. | |
| 5,304,557 A | 4/1994 | Mylari | |
| 5,677,342 A | 10/1997 | Malamas et al. | |
| 5,728,704 A | 3/1998 | Mylari et al. | |
| 6,159,976 A | 12/2000 | Lambert et al. | |
| 6,544,756 B1 | 4/2003 | Uchida et al. | |
| 6,570,013 B2 | 5/2003 | Mylari | |
| 6,579,879 B2 | 6/2003 | Mylari | |
| 6,696,407 B1 | 2/2004 | Longo et al. | |
| 6,849,629 B2 | 2/2005 | Mylari | |
| 6,916,824 B1 | 7/2005 | Hua et al. | |
| 7,572,910 B2 | 8/2009 | Mylari | |
| 8,916,563 B2 | 12/2014 | Wasmuth et al. | |
| 9,650,383 B2 | 5/2017 | Wasmuth et al. | |
| 9,921,221 B2 | 3/2018 | King et al. | |
| 10,052,324 B2 | 8/2018 | Wasmuth et al. | |
| 10,150,779 B2 | 12/2018 | Wasmuth et al. | |
| 10,639,306 B2 | 5/2020 | Wasmuth et al. | |
| 10,647,726 B2 * | 5/2020 | Wasmuth | A61Q 19/08 |
| 10,870,658 B2 * | 12/2020 | Wasmuth | A61P 17/00 |
| 11,498,925 B2 * | 11/2022 | Wasmuth | A61P 17/00 |
| 11,529,349 B2 | 12/2022 | Wasmuth et al. | |
| 11,730,737 B2 | 8/2023 | Wasmuth et al. | |
| 12,077,547 B2 | 9/2024 | Wasmuth et al. | |
| 2002/0068740 A1 | 6/2002 | Mylari | |
| 2006/0293265 A1 | 12/2006 | Srivastava et al. | |
| 2006/0293371 A1 | 12/2006 | Kamiyama | |
| 2007/0060533 A1 | 3/2007 | Yoshikawa et al. | |
| 2010/0215726 A1 | 8/2010 | Roh | |
| 2011/0092566 A1 | 4/2011 | Srivastava et al. | |
| 2013/0029983 A1 | 1/2013 | Ballatore et al. | |
| 2013/0225592 A1 | 8/2013 | Wasmuth et al. | |
| 2014/0113380 A1 | 4/2014 | Lawrence et al. | |
| 2015/0018240 A1 | 1/2015 | Jackson et al. | |
| 2015/0072989 A1 | 3/2015 | Wasmuth et al. | |

(Continued)

FOREIGN PATENT DOCUMENTS

| | | |
|---|---|---|
| CA | 1299178 | 4/1992 |
| CA | 2366858 | 10/2000 |

(Continued)

OTHER PUBLICATIONS

Alexander et al., "(Acyloxy)alkyl carbamates as novel bioreversible prodrugs for amines: increased permeation through biological membranes", J. Med. Chem., 31, pp. 318-322 (1988).

Antonetti et al., "Vascular Permeability in Experimental Diabetes is Associated with Reduced Endothelial Occludin Content: Vascular Endothelial Growth Factor Decreases Occludin in Retinal Endothlial Cells", Diabetes, 47, pp. 1953-1959 (Dec. 1998).

Aydin-Azemir et al. "Galactosemia and phantom absence seizures" Journal of Pediatric Neurosciences, Dec. 2014, vol. 9, p. 253-256; p. 1, introduction: para 1.

(Continued)

*Primary Examiner* — Pancham Bakshi

(74) *Attorney, Agent, or Firm* — Hogan Lovells US LLP

(57) ABSTRACT

The present disclosure relates to novel compounds and pharmaceutical compositions thereof, and methods for promoting healthy aging of skin, the treatment of skin disorders, the treatment of cardiovascular disorders, the treatment of renal disorders, the treatment of angiogenesis disorders, such as cancer, treatment of tissue damage, such as non-cardiac tissue damage, the treatment of evolving myocardial infarction, the treatment of ischemic injury, and the treatment of various other disorders, such as complications arising from diabetes with the compounds and compositions of the invention. Other disorders can include, but are not limited to, atherosclerosis, cardiomyopathy, coronary artery disease, diabetic nephropathy, diabetic neuropathy, diabetic retinopathy, diabetic cardiomyopathy, infections of the skin, peripheral vascular disease, stroke, galactosemia, asthma, PMM2-CDG and the like.

6 Claims, No Drawings

(56) References Cited

U.S. PATENT DOCUMENTS

| | | | |
|---|---|---|---|
| 2015/0079104 | A1 | 3/2015 | Zhou et al. |
| 2015/0079105 | A1 | 3/2015 | Chambers et al. |
| 2016/0029983 | A1 | 2/2016 | Verna et al. |
| 2017/0216291 | A1 | 8/2017 | Wasmuth et al. |
| 2017/0216292 | A1 | 8/2017 | Wasmuth et al. |
| 2017/0319584 | A1 | 11/2017 | Wasmuth et al. |
| 2017/0362237 | A1 | 12/2017 | Mylari |
| 2018/0085437 | A1 | 3/2018 | Fan |
| 2018/0209997 | A1 | 7/2018 | Cohen et al. |
| 2018/0237451 | A1 | 8/2018 | Wasmuth et al. |
| 2018/0271865 | A1 | 9/2018 | Wasmuth et al. |
| 2018/0312828 | A1 | 11/2018 | Liu et al. |
| 2019/0201400 | A1 | 7/2019 | Wasmuth et al. |
| 2020/0028345 | A1 | 1/2020 | Roy et al. |
| 2020/0131203 | A1 | 4/2020 | Shendelman |
| 2020/0230139 | A1 | 7/2020 | Shendelman |
| 2020/0268755 | A1 | 8/2020 | Wasmuth et al. |
| 2020/0283451 | A1 | 9/2020 | Wasmuth et al. |
| 2020/0289512 | A1 | 9/2020 | Wasmuth et al. |
| 2021/0284652 | A1 | 9/2021 | Wasmuth et al. |
| 2022/0017535 | A1 | 1/2022 | Wasmuth |
| 2022/0071880 | A1 | 3/2022 | Shendelman |
| 2022/0125890 | A1 | 4/2022 | Zuchner et al. |
| 2022/0226323 | A1 | 7/2022 | Perfetti et al. |
| 2022/0249624 | A1 | 8/2022 | Zuchner et al. |
| 2023/0058134 | A1 | 2/2023 | Shendelman |
| 2023/0121312 | A1 | 4/2023 | Shendelman |
| 2023/0293642 | A9 | 9/2023 | Zuchner |
| 2023/0312599 | A1 | 10/2023 | Wasmuth et al. |
| 2024/0180907 | A1 | 6/2024 | Wasmuth et al. |
| 2024/0238288 | A1 | 7/2024 | Shendelman |
| 2024/0374693 | A1 | 11/2024 | Zuchner et al. |
| 2025/0163073 | A1 | 5/2025 | Wasmuth et al. |

FOREIGN PATENT DOCUMENTS

| | | | |
|---|---|---|---|
| CN | 101143868 | | 3/2008 |
| CN | 102512407 | | 6/2012 |
| EP | 0256629 | A2 | 2/1988 |
| EP | 0189272 | A2 | 7/1988 |
| EP | 0325375 | A1 | 7/1989 |
| EP | 0397350 | A1 | 11/1990 |
| EP | 0401981 | A1 | 12/1990 |
| EP | 0436307 | A1 | 7/1991 |
| EP | 0222576 | | 3/1992 |
| EP | 2065038 | A1 | 6/2009 |
| EP | 3597650 | A1 | 1/2020 |
| EP | 3757107 | A1 | 12/2020 |
| FR | 2647676 | | 12/1990 |
| JP | 2003-155274 | | 5/2003 |
| WO | 198905791 | | 6/1989 |
| WO | 198906651 | | 7/1989 |
| WO | 1991009019 | | 6/1991 |
| WO | 1995026347 | A1 | 10/1995 |
| WO | 1998042324 | A2 | 10/1998 |
| WO | 1999015529 | | 4/1999 |
| WO | 1999050268 | | 10/1999 |
| WO | 2000059510 | A1 | 10/2000 |
| WO | 2002079198 | A1 | 10/2002 |
| WO | 2003061660 | A1 | 7/2003 |
| WO | 2008002678 | A1 | 1/2008 |
| WO | 2010028132 | A2 | 3/2010 |
| WO | 2012009553 | A1 | 1/2012 |
| WO | 2014113380 | A1 | 7/2014 |
| WO | 2014126885 | A1 | 8/2014 |
| WO | 2017191274 | A1 | 11/2017 |
| WO | 2017223179 | A1 | 12/2017 |
| WO | 2018090006 | A1 | 5/2018 |
| WO | 2018200258 | A1 | 11/2018 |
| WO | 2019023648 | A1 | 1/2019 |
| WO | 2020040831 | A1 | 2/2020 |
| WO | 2020167937 | A1 | 8/2020 |
| WO | 2020205846 | A1 | 10/2020 |
| WO | 2020227430 | A1 | 11/2020 |
| WO | 2021071965 | A1 | 4/2021 |
| WO | 2021202523 | A1 | 10/2021 |
| WO | 2021222165 | A1 | 11/2021 |

OTHER PUBLICATIONS

Ayres et al., "Synthesis of derivates of cyclobuteno[c]thiophen and attempts to synthesise thiophen analogues of bipheneylene", Tetrahedron, 31, pp. 1755-1760 (1975).

Berge et al., "Pharmaceutical Salts", J. Pharm. Sci., 66(1), pp. 1-19 (1977).

Beyer-Mears et al., "Glomerular Polyol Accumulation in Diabetes and its Prevention by Oral Sorbinil", Diabetes, Jun. 1984, vol. 33, No. 6, pp. 604-607.

Caliceti et al., "New Insights from Pharmacological Aspects to Clinical Evidences in the Management of Metabolic Disorders", Curr. Med. Chem. (2016) vol. 23, No. 14, pp. 1460-1476.

Cannon, "Chapter Nineteen: Analog Design," Burger's Medicinal Chemistry and Drug Discovery: fifth edition, vol. 1: Principles and Practice, Wiley-Interscience, pp. 783-802 (1995).

Carbone et al., "Structure of Aldehyde reductase in ternary complex with a 5-arylidene-2,4-thiazolidinedione aldose reductase inhibitor", European Journal of Medicinal Chemistry, 45(3):1140-1145, Mar. 31, 2010 available online Dec. 21, 2009 (5 pages).

Chatzopoulou et al. "Novel Aldose Reductase Inhibitors: a patent survey (2006-present)", Expert Opinion on Therapeutic Patents, 2012, vol. 22:11, pp. 1303-1323, p. 1307, Figure 4.

Cheng et al., "The effect of high glucose and oxidative stress on lens metabolism, aldose reductase, and senile cataractogenesis", Abstract only, Metabolism, Apr. 1986, vol. 35, No. 4 Suppl. 1, pp. 10-14.

Cheung et al., "Aldose Reductase Deficiency Prevents Diabetes-Induced Blood-Retinal Barrier Breakdown, Apoptosis, and Glial Reactivation in the Retina of db/db Mice," Diabetes, Nov. 2005, vol. 54, No. 11 pp. 3119-3125.

Coelho et al. "Sweet and sour: an update on classic galactosemia" Journal of Inherited Metabolic Disease Mar. 9, 2017 vol. 40, p. 325-342; p. 331, left col. Para 4, p. 332, left col, para 4, p. 33, left col, para 3.

Cortese et al., "Biallelic Mutations in SORD cause a common and Potentially Treatable Hereditary Neuropathy with Implications for Diabetes", Nature Genetics, Articles https://doi.org/10.1038/s41588-020-0615-4, 19 pages.

Coyle et al. "A Recovered Case of COVID-19 Myocarditis and ARDS Treated with Corticosteroids, Tocilizumab, and Experimental AT-001", JACC. Case Reports, vol. 2, No. 9, Jul. 15, 2020, pp. 1331-1336, XP009528095, ISSN: 2666-0849, DOI: 10.1016/J.JACCAS 2020.04.025 [retrieved on May 3, 2020] example 4.

Digiacomao, M. "Synthesis and functional evaluation of novel aldose reductase inhibitors" The Open Medicinal Chemistry Journal, Apr. 2017, vol. 11.

Ghosh Sutapa et al., "Recent Advances in Drug Discovery Research Using Structure-Based Virtual Screening Techniques: Examples of Success for Diverse Protein Targets" in "Drug Discovery Research", Jun. 8, 2007, John Wiley & Sons, Inc., Hoboken NJ, USA, XP05514110, ISBN: 978-0-471-67200-5 pp. 24-62, DOI: 10.1002/9780470131862.ch2 Retrieved from the Internet: https://doi.org/10.1002/9780470131862.ch2.

Grewal et al., "Updates on Aldose Reductase Inhibitors for Management of Diabetic Complications and Non-diabetic Diseases" (Mini-Reviews in Medicinal Chemistry, 2016, vol. 16(2), pp. 120-162, [online], [retrieved Mar. 17, 2022] found in PubMed, RMS: 26349493, doi: 10.2174/1389557515666150909143737).

Gu et al., "Effects of lignans extracted from Eucommia ulmoides and aldose reductase inhibitor epalrestat on hypertensive vascular remodeling", Abstract only, J. Ethnopharmacol, Jan. 17, 2011, vol. 133, No. 1, pp. 6-13.

Hartsock et al., "A Mouse Model of Retinal Ischemia-Reperfusion Injury Through Elevation of Intraocular Pressure", Journal of Visualized Experiments, 113, e54065, 6 pages (2016).

Hiohman et al. "Probing the Inhibitor-binding site of aldose reductase with site-directed mutagenesis", Eur. J. Biochem 1998, vol. 256, pp. 310-316.

(56) References Cited

OTHER PUBLICATIONS

Hotta et al., "Stratified analyses for selecting appropriate target patients with diabetic peripheral neuropathy for long- term treatment with an aldose reductase inhibitor, epalrestat", Diabet. Med. (2008), vol. 25, No. 7, pp. 818-825.
Hotta et al., "Short Report: Treatment—Long-term clinical effects of epalrestat, an aldose reductase inhibitor, on progression of diabetic neuropathy and other microvascular complications; multiverse epidemiological analysis based on patient background factors and severity of diabetic neuropathy", Diabetic Medicine, 29:1529-1533, 2012 (5 pages).
Hotta et al. "Long-Term Clinical Effects of Epalrestat, an Aldose Reductase Inhibitor, on Diabetic Peripheral Neuropathy", Diabetes Care, 29(7), pp. 1538-1544 (Jul. 2006).
Hu et al., "Efficacy and Safety of aldose reductase inhibitor for the treatment of diabetic cardiovascular autonomic neuropathy: systematic review and meta-analysis", Plos One, 9(2), e87096, pp. 1-11 (2014).
Hwang et al., "Central role for aldose reductase pathway in myocardial ischemic injury" The FASEB Journal, Aug. 2004, vol. 18, No. 11, pp. 1192-1199.
Iyer et al. "Repurposing the aldose reductase inhibitor and diabetic neuropathy drug epalrestat for the congenital disorder of glycosylation PMM2-CDG" Dis. Model. Mech. (2019) 12(11). bioRxiv preprint first posted online May 3, 2019; doi: http://dx.doi.org/10.1101/626697.
Jacoby et al., "Acute Myocardial Infarction in the Diabetic Patient: Pathophysiology, Clinical course and Prognosis", J. Am. Coll. Cardio., vol. 20, No. 3, pp. 736-744 (1992).
Johnson et al., "Cardiac Abnormalities in Diabetic Patients with Neuropathy", Diabetes Care, Feb. 2004, vol. 27, No. 2, pp. 448-454.
Kajiwara et al., "Lower incidence of myocardial infarction in type 2 diabetic patients with polyneuropathy who were treated with an aldose reductacse inhibitor (epalrestat): a retrospective study", Presentation Abstract, Presentation humber 1241, 47th EASD Annual Meeting, Lisbon, 2011.
Kalofoutis et al., "Type II diabetes mellitus and cardiovascular risk factors: current therapeutic approaches" Exp. Clin. Cardiol., 2007, vol. 12, No. 1 pp. 17-28.
Kasajima et al., "Enhanced in situ expression of aldose reductase in peripheral nerve and renal glomeruli in diabetic patients", Abstract only, Virchows Arch., Jul. 2001, vol. 439, No. 1.
Kinoshita, "A thirty year journey in the polyol pathway", Exp. Eye. Res., vol. 50, No. 6, pp. 567-573 (1990).
Lao et al. "Yeast Models of Phosphomannomutase 2 Deficiency, a Congenital Disorder of Glycosylation" G3 (Bethesda, Md.), Feb. 7, 2019, 9(2):413-423.
Li et al., "Polyol pathway and modulation of ischemia-reperfusion injury in Type 2 diabetic BBZ rat hearts", Cardiovascular Diabetology, Oct. 28, 2008, vol. 7, No. 33, 11 pages.
Li et al., "Redox State-Dependent and Sorbitol Accumulation-Independent Diabetic Albuminuria in Mice with Transgene-Derived Human Aldose Reductase and Sorbitol Dehydrogenase Deficiency", Diabetologia, Feb. 14, 2004, vol. 47, No. 3, pp. 541-548 entire document.
Lightman, S. "Does Aldose Reductase have a role in the development of the ocular complications of diabetes?" Eye, 1993, vol. 7, pp. 238-241.
Liu et al., "Genetic deficiency of aldose reductase counteracts the development of diabetic nephropathy in C57BL/6 mice", Diabetologia, Jan. 27, 2011, vol. 54, No. 5, pp. 1242-1251.
Lorenzi, "The Polyol Pathway as a Mechanism for Diabetic Retinopathy: Attractive, Elusive and Resilient", Experimental Diabetes Resarch, vol. 2007, Article ID 61038, 10 pages (2007).
Maratha et al., Classical Galactosaemia and CDG, the N-Glycosylation Interface, A review, JIMD Reports, Aug. 9, 2016, vol. 34, pp. 33-42; p. 34.
Marin-Neto et al., "Cardiovascular effects of berberine in patients with severe congestive heart failure," Clin. Cardiol., Apr. 1988, vol. 11, No. 4, pp. 253-260.
Mylari, Banavara L. et al., "Novel, Potent Aldose Reductase Inhibitors: 3,4-Dihydro-4-oxo-3-[5-(trifuoromethyl)-2-benzothiazolyl]-1-phthalazine-acetic Acid (Zopolrestat) and Congeners", J. Med. Chem., 1991, vol. 34, pp. 108-122.
Mylari, Banavara L., et al., "Potent, Orally Active Aldose Reductase Inhibitors Related to Zopolrestat: Surrogates for Benzothiazole Side Chain", J. Med. Chem., 1992, vol. 35, pp. 457-465.
Mylari et al., "Orally active aldose reductase inhibitors: indazoleacetic, oxopyridazineacetic, and oxopyridopyridazineacetic acid derivatives", J. Med. Chem. 1992, 35, 2155-2162.
Mylari et al., "A Novel Series of Non-Carboxylic Acid, Non-Hydantoin Inhibitors of Aldose Reductase with Potent Oral Activity in Diabetic Rat Models: 6-(5-Chloro-3-methylbenzofuran-2-sulfony)-2H-pyridazin-3-one and Congeners", J. Med. Chem., 48, pp. 6326-6339 (2005).
Nour et al. "Ischemia-Reperfusion Injury in Stroke" Intervent Neurol, 2012, vol. 1, pp. 185-199.
Price et al., "Mitogen-Activated Protein Kinase p38 Mediates Reduced Nerve Conduction Velocity in Experimental Diabetic Neuropathy", Diabetes, Jul. 2004, vol. 53, No. 7 pp. 1851-1856.
Ramana et al., "Inhibiton of aldose reductase prevents growth factor-induced G1-S phase transition through the AKT/phosphoinositide 3-kinase/E2F-1 pathway in human colon cancer cells", Mol. Cancer ther., 9(4), pp. 813-824 (2010).
Ramasamy et al., "Aldose reductase and cardiovascular diseases, creating human-like diabetic complications in an experimental model" Circ Res, May 2010, vol. 106, No. 9, pp. 1449-1458.
Ridel et al., "An Updated Review of the Long-Term Neurological Effects of Galactosemia," Pediatric Neurology(2005) 33(3):153-161.
International Search Report and Written Option mailed on Jun. 17, 2020 for PCT/US2020/025928 (12 pages).
Hao, W. et al., "Hyperglycemia Promotes Schwann Cell De-differentiation and De-myelination via Sorbitol Accumulation and Igf1 Protein Down-regulation", The Journal of Biological Chemistry (2015) 290(28):17106-17115.
Miyamoto, S., et al., "Recent advances in aldose reductase inhibitors: potential agents for the treatment of diabetic complications", Expert Opin. Ther. Pat. (2002) 12(5):621-631.
Nambu, H., et al., "Attenuation of aldose reductase gene suppresses high-glucose-induced apoptosis and oxidative stress in rat lens epithelial cells", Diabetes Res. Clin. Pract. (2008) 82(1):18-24.
Obrosova, I. G., et al., "Aldose Reductase Inhibition Counteracts Oxidative-Nitrosative Stress and Poly(ADP- Ribose) Polymerase Activation in Tissue Sites for Diabetes Complications", American Diabetes Association (2005) 54(1):234-242.
Patil et al., "The Fate of Aldose Reductase Inhibition and Sorbitol Dehydrogenase Activation", Austin Journal of Endocrinology and Diabetes (2019) 6(1):1-7.
Roy, Thomas M. et al., "The effect of an aldose reductase inhibitor on cardiovascular performance in patients with diabetes mellitus", Diabetes Research and Clinical Practice 1990, vol. 10, pp. 91-97.
Sato et al. "Dose-Dependent Prevention of Sugar Cataracts in Galactose-fed Dogs by the Aldose Reductase Inhibitor M79175" Laboratory of Ocular Therapeutics, National Eye Institute, National Institutes of Health, Exo. Eye Res. (1998) 66:217-222.
Satoh et al., "Effect of Ranirestat on Sensory and Motor Nerve Function in Japanese Patients with Diabetic Polyneuropathy: A Randomized Double-Blind Placebo-Controlled Study", J. Diabetes Res. 2016, article ID 5383797, 8 pages (2016).
Schulz et al., "Identification of novel downstream targets of platelet glycoprotein VI activation by differential proteosome analysis: implications for thrombus formation", Blood, May 20, 2010, vol. 115, No. 20, pp. 4102-4110.
Sheridan, "The most common replacements in Drug-like compounds", J. Chem. Inf. Comput. Sci., vol. 42, pp. 103-108 (2002).
Srivastava et al., "Aldose reductase inhibition suppressed oxidative stress-induced inflammatory disorders", author manuscript, published in final edited form as : Chem. Biol. Interact, 1991, pp. 330-338 (2011), 19 pages.
Tammali et al., "Inhibitor of Aldose Reductase Prevents Angiogenesis in vitro and in vivo", published in final edited form as: Angiogenesis, 14(2), pp. 209-221 (May 2011) 19 pages.

(56) References Cited

OTHER PUBLICATIONS

Tang et al., "Glucose and collagen regulate human platelet activity through aldose reductase induction of thromboxane", The Journal of Clinical Investigation, No. 2011, vol. 121, No. 11 pp. 4462-4476.
Tang et al., "Aldose reductase, oxidative stress, and diabetic mellitus", Frontiers in Pharmacology, May 9, 2012, vol. 3, Article 87, 8 pages.
Tawata et al., "Anti-platelet action of isoliquiritigenin, an aldose reductase inhibitor in licorice", abstract only, Eur. J. Pharmacol, Feb. 25, 1992, vol. 212, No. 1, pp. 87-92.
Tianhong Xu et al., "Indomethacin has a potent antiviral activity against SARS COV-2 in vitro and canine coronavirus in vivo" bioRxiv, Apr. 5, 2020, XP055742348, DOI: 10.1101/2020.04.01.017624 Retrieved from the Internet: URL: https://www.biorxiv.org/content/10.1101/2020.04.01.017624v1.full.pdf p. 5, para 2-3.
Trippier et al."Boronic Acids in Medicinal Chemistry: anticancer, antibacterial and antiviral applications", Med. Chem. Commun 2010, vol. 1, pp. 183-198. pg. 183, col. 1, para 4: p. 185, Table 2.
Vedantham et al., "Human Aldose Reductase Expression Accelerates Atherosclerosis in Diabetic apoE-/- Mice Reductase", Arteriosler. Thromb. Vasc. Biol. vol. 31, No. 8 pp. 1805-1813, Aug. 1, 2012.
Veves, "Aldose Reductase Inhibitors for the treatment of Diabetic Neuropathy", Contemporary Diabetes: Diabetic Neuropathy: Clinical Management, Second edition, Humana Press, chapter 18, pp. 309-320 (2007).
Wilson et al., "Refined 1.8 a structure of human aldose reductase complexed with the potent inhibitor zopolrestat", Proc. Natl. Acad. Sci. USA, vol. 90, No. 21, pp. 9847-9841 (Nov. 1993).
Xu et al., "Indomethacin has a potent antiviral activity against SARS COV-2 in vitro and canine coronavirus in vivo" bioRxiv, Apr. 5, 2020, XP055742348, DOI: 10.1101/2020.04.01.017624 Retrieved from the Internet: URL: https://www.biorxiv.org/content/10.1101/2020.04.01.017624v1.full.pdf p. 5, para 2-3.
Yagihashi et al., "Neuropathy in diabetic mice overexpressing human aldose reductse and effects of aldose reductase inhibitor", Brain, Dec. 2001, vol. 124, Pt. 12, pp. 2448-2458.
Zeng et al., "Efficacy and safety of berberine for congestive heart failure secondary to ischemic or idiopathic dilated cardiomyophaty", abstract only, Am. J. Cardiol. Jul. 15, 2003, vol. 92, No. 2, pp. 173-176.
Zhang et al. "Bioactivity Focus of α-Cyano-4-hydroxycinnamic acid (CHCA) Leads to Effective Multifunctional Aldose Reductase Inhibitors" Sci. Rep. (2016) 6:24942.
Zhou et al., "Neuroprotective effects of berberine on stroke models in vitro and in vivo", abstract only, Neurosci. Lett., Dec. 5, 2008, vol. 447, No. 1, pp. 31-36.
Zhu, C. "Aldose Reductase Inhibitors as Potential Therapeutics Drugs of Diabetic Complications", Chapter 2 of Diabetes Mellitus—Insights and Perspectives Jan. 23, 2013, pp. 17-46, book edited by Oluwafemi O. Oguntibeju, published: Jan. 23, 2013 under CC BY 3.0 License.
Clinical Trials.gov, "Ezetimibe Versus Nutraceuticals in Statin-intolerant Patients (ECLIPSE)", ClinicalTrials.Gov Identifier No. NTC01490229, First received Dec. 8, 2011, 4 pages.
Clinical Trials.gov, "Low-dose Statins, and Nutraceuticals in High-intensity Statin-intolerant Patients (ADHERENCE)", ClinicalTrials Gov identifier No. NTC02001883, first received Nov. 24, 2013, 4 pages.
Pubchem, Substance Record for SID 227698804, Available Date: Feb. 12, 2015, Retrieved from the internet: https://pubchem.ncbi.nlm.nih.gov/substance/227698804.
International Search Report & Written Opinion for PCT/US2018/027960 mailed on Jul. 11, 2018.
International Search Report & Written Opinion for PCT/US2018/044199 mailed Oct. 24, 2018.
International Search Report and Written Opinion for PCT/US2020/025928 mailed Jun. 17, 2020.
International Search Report and Written Opinion for PCT/US2020/054607 mailed Jan. 28, 2021.
International Search Report and Written Opinion for PCT/US2020/031708 mailed Aug. 12, 2020.
International Search Report and Written Opinion for PCT/US2021/024876 mailed Jun. 30, 2021.
International Search Report and Written Opinion for PCT/US2021/029286 mailed Aug. 11, 2021.
International Search Report and Written Opinion for PCT/US2011/044038 mailed Dec. 6, 2011.
Li et al., "Decarboxylative borylation", Science, 2017, 356 (6342), 16 pages.
Kamijo, M et al. "Galactosemia produces ARI-preventable nodal changes similar to those of diabetic neuropathy," Diabetes Research and Clinical Practice (1994) 25:117-129.
Monticelli, et al., "B-Glucose-1,6-Bisphosphate Stabilizes Pathological Phophomannomutase2 Mutants In Vitro and Represents a Lead Compound to Develop Pharmacological Chaperones for the Most Common Disorder of Glycosylation, PMM2-CDG", International Journal of Molecular Sciences (2019) 20(4164):3-15.
Oka, M., et al. "Aldose Reductase Inhibitors," Journal of Enzyme Inhibition (2001) 16:465-473.

* cited by examiner

INHIBITORS OF ALDOSE REDUCTASE

RELATED APPLICATIONS

This application filed under 35 U.S.C. 111(a) is a continuation of International Application No. PCT/US2020/025928, filed on Mar. 31, 2020, which claims the benefit of U.S. Provisional Application No. 62/827,362, filed on Apr. 1, 2019 and U.S. Provisional Application No. 62/928,735, filed on Oct. 31, 2019. The entire teachings of the above applications are incorporated herein by reference.

FIELD OF THE INVENTION

The present invention relates to novel compounds and pharmaceutical compositions thereof, and methods for promoting healthy aging of skin, the treatment of skin disorders, treatment of cutaneous aging, the treatment of cardiovascular disorders, the treatment of renal disorders, the treatment of angiogenesis disorders, such as cancer, treatment of tissue damage, such as non-cardiac tissue damage, the treatment of evolving myocardial infarction, the treatment of ischemic injury, and the treatment of various other disorders, such as complications arising from diabetes with the compounds and compositions of the invention. Other disorders can include, but are not limited to, atherosclerosis, cardiomyopathy, coronary artery disease, diabetic nephropathy, diabetic neuropathy, diabetic retinopathy, diabetic cardiomyopathy, infections of the skin, peripheral vascular disease, stroke, galactosemia, PMM2-CDG, asthma, and the like.

BACKGROUND OF THE INVENTION

An estimated 15 million people worldwide suffer from stroke each year. Stroke (cerebral infarction) is a condition in which poor blood flow to the brain results in cell death. There are two main types of stroke: ischemic, which is due to restricted blood flow, and hemorrhagic, which is due to bleeding. Ischemic strokes account for about 87% of cases. Both types of stroke can affect proper brain function, either temporarily or permanently.

Despite the ubiquity of strokes, few interventions exist. The only FDA approved drug to treat ischemic stroke is tissue plasminogen activator (tPA), which is a clot busting drug. tPA must be given within 3 to 4.5 hours of the first symptoms of stroke. (Xin et al., in *Neurochemistry International* 2014, 68, 18-27, which is hereby incorporated by reference in its entirety.) Medication may also be used to treat brain swelling that sometimes occurs after a stroke.

In addition to limiting the duration of ischemia via treatment of a clot busting drug, an alternative strategy is to limit the severity of ischemic injury (i.e., neuronal protection). Neuroprotective strategies can potentially preserve the penumbral tissues and extend the time window for revascularization techniques. At the present time, however, there are no neuroprotective treatments nor have any neuroprotective agents been shown to impact clinical outcomes in ischemic stroke.

Recent studies have indicated that much of the neural damage caused by stroke is related to high levels of endoplasmic reticulum stress and reactive oxygen species (ROS). Aldose reductase inhibitors (ARIs) have been shown to attenuate ROS production, and reduce stroke damage in mice. For example, the inhibition of the enzyme aldose reductase (AR) has a beneficial effect during ischemic stroke. AR-knockout (deficient) mice underwent a cerebral infarction (2 h of ischemia followed by 22 h of reprefusion) and the results were compared to those of normal mice. The results showed a significant reduction (25-33%) reduction in infarct volume in the brain slices of the AR-knockout mice compared to control groups. Additionally, using normal mice, it was shown that single dose treatment (orally) of the mice with an aldose reductase inhibitor (Fidarestat) either 30 mins before ischmia or 1 hand 45 mins after ischemia also showed significant reduction (16-25%) in infarct volume resulting from ischemic injury.

Aldose reductase (AR) is a monomeric, NADPH-dependent oxidoreductase from the aldo-keto reductase family of enzymes. It is an enzyme that is present in many parts of the body. Aldose reductase catalyzes the reduction of saturated and unsaturated aldehydes, including aldo sugars and monosaccharides, as well as a broad array of other substrates. Primarily, aldose reductase catalyzes the reduction of glucose to sorbitol, one of the steps in the sorbitol pathway that is responsible for fructose formation from glucose. AR has recently been implicated in a wide range of therapeutic areas including cancer, myocardial infarction and ischemic injury, asthma, transplantation, and in harmful inflammatory responses. (Chatzopoulou et al., *Expert Opin Drug Discov.* 2013, 8(11), 1365-80.)

Aldose reductase is also present in the human brain in appreciable amounts. Aldose reductase inhibitors may act as an adjunctive treatment offering neuroprotection during revascularization of the brain tissue. However, for aldose reductase inhibitors to be effective, they may need to cross the blood brain barrier. Thus, there is a need for aldose reductase inhibitor compounds that can cross the blood brain barrier.

SUMMARY

It is understood that any of the embodiments described below can be combined in any desired way, and that any embodiment or combination of embodiments can be applied to each of the aspects described below, unless the context indicates otherwise.

In one aspect, the invention provides a compound of Formula (I)

(I)

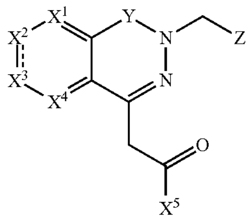

wherein,

- $X^1$ is N or $CR^1$;
- $X^2$ is N, $CR^2$, or S;
- $X^3$ is N, $CR^3$, or a bond;
- $X^4$ is N or $CR^4$; with the proviso that when $X^2$ is S, $X^1$ is $CR^1$, $X^4$ is $CR^4$, and $X^3$ is a single bond; or that two or three of $X^1$, $X^2$, $X^3$, or $X^4$ are N;
- Y is a bond, C=O, C=S, C=NH, or C=N($C_1$-$C_4$)-alkyl;

Z is

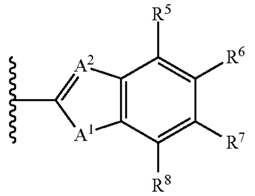

or

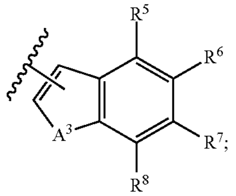

$A^1$ is $NR^9$, O, S or $CH_2$;

$A^2$ is N or CH;

$A^3$ is $NR^9$, O, or S;

$R^1$ through $R^8$ are independently hydrogen, halogen, cyano, acyl, haloalkyl, haloalkoxy, haloalkylthio, trifluoroacetyl, $(C_1\text{-}C_4)$-alkyl, $(C_1\text{-}C_4)$-alkoxy, $(C_1\text{-}C_4)$-alkylthio, $(C_1\text{-}C_4)$-alkylsulfinyl, or $(C_1\text{-}C_4)$-alkylsulfonyl; or two of $R^1$ through $R^4$ or two of $R^5$ through $R^8$ taken together are $(C_1\text{-}C_4)$-alkylenedioxy;

$R^9$ is hydrogen, $C_1\text{-}C_4$ alkyl, or C(O)O—$(C_1\text{-}C_4)$-alkyl;

$X^5$ is Q-$R^{10}$;

Q is O, NH, O—$(C_1\text{-}C_6)$-alkyl, O—$(C_1\text{-}C_6)$-hydroxyalkyl, O—$(C_1\text{-}C_6)$-aminoalkyl, O-aryl, O-heteroaryl, O-biaryl, O-benzyl, NH—$(C_1\text{-}C_6)$-alkyl, NH—$(C_1\text{-}C_6)$-hydroxyalkyl, NH—$(C_1\text{-}C_6)$-aminoalkyl, NH-aryl, NH-heteroaryl, NH-biaryl, NH-benzyl, or a bond;

$R^{10}$ is

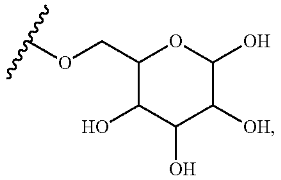

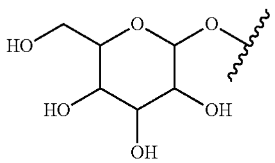

,

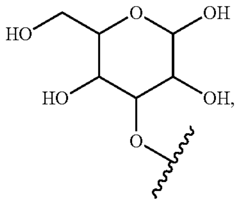

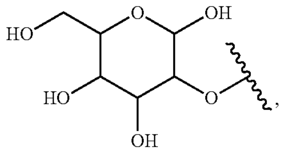

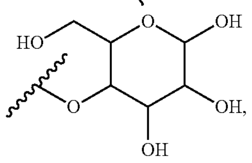

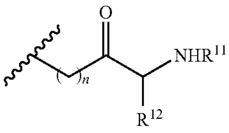

,

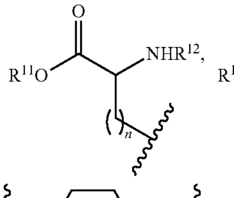

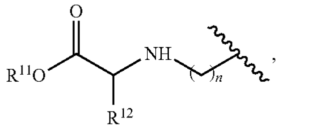

,

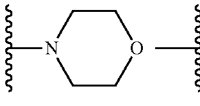

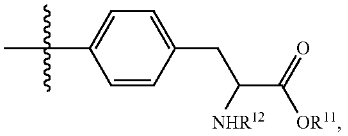

aryl, heteroaryl, biaryl, benzyl, heterocycle, C(O)$OR^{11}$ and OH, with the proviso that when Q is NH, $R^{10}$ can also be H; and $R^{11}$ and $R^{12}$ are independently H or $(C_1\text{-}C_6)$-alkyl optionally substituted with one or more substituents selected from the group consisting of $OR^{13}$, $NHR^{13}$, $SR^{13}$, $CO_2R^{13}$, $CONHR^{13}$, aryl, hydroxyaryl, indolyl, imidazolyl, and $NH(CNH)NH_2$;

or $R^{11}$ and $R^{12}$, taken together with the atoms to which they are attached, form a 3-7 membered heterocyclic ring;

$R^{13}$ is H or $(C_1\text{-}C_6)$-alkyl; and n is 0, 1, or 2; or a pharmaceutically acceptable salt thereof.

In Formula (I), $R^{10}$ can be bonded to any substitutable atom in Q. For example, when Q is O—$(C_1\text{-}C_6)$alkyl, $R^{10}$ can be bonded to any of the carbon atoms in the alkyl.

In some embodiments, $X^1$ and $X^4$ are N, and $X^2$ and $X^3$ are CH; or $X^1$ is $CR^1$, $X^4$ is $CR^4$, $X^2$ is S, and $X^3$ is a bond; or a pharmaceutically acceptable salt or solvate thereof.

In some embodiments, Y is C═O;

$A^1$ is $NR^9$, O, or S;

$A^2$ is N;

$A^3$ is O, or S; and $R^5$ through $R^8$ are independently hydrogen, halogen, cyano, acyl, haloalkyl, haloalkoxy, haloalkylthio, trifluoroacetyl, $(C_1\text{-}C_4)$-alkyl, $(C_1\text{-}C_4)$-alkoxy, $(C_1\text{-}C_4)$-alkylthio, $(C_1\text{-}C_4)$-alkylsulfinyl, or $(C_1\text{-}C_4)$-alkylsulfonyl;

or a pharmaceutically acceptable salt or solvate thereof.

In some embodiments, $R^5$ through $R^8$ are independently hydrogen, halogen, or haloalkyl; and $R^9$ is hydrogen, $(C_1\text{-}C_4)$-alkyl, or C(O)O-tert-butyl; or a pharmaceutically acceptable salt or solvate thereof.

In some embodiments, Z is

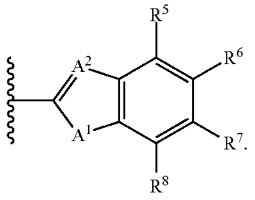

In some embodiments, Y is C═0;

$A^1$ is $NR^9$, O, or S;

$A^2$ is N;

$R^5$ through $R^8$ are independently hydrogen, halogen, cyano, acyl, haloalkyl, haloalkoxy, haloalkylthio, $(C_1\text{-}C_4)$-alkyl, $(C_1\text{-}C_4)$-alkoxy, $(C_1\text{-}C_4)$-alkylthio, $(C_1\text{-}C_4)$-alkylsulfinyl, or $(C_1\text{-}C_4)$-alkylsulfonyl; and $R^9$ is hydrogen, $C_1\text{-}C_4$ alkyl, or C(O)O—$(C_1\text{-}C_4)$-alkyl; or a pharmaceutically acceptable salt or solvate thereof.

In some embodiments, Y is C═O;

$A^1$ is $NR^9$, O or S;

$A^2$ is N;

$R^5$ through $R^8$ are independently hydrogen, halogen, or haloalkyl; and $R^9$ is hydrogen, $(C_1\text{-}C_4)$-alkyl, or C(O)O-tert-butyl; or a pharmaceutically acceptable salt or solvate thereof.

In some embodiments, Y is C═O;

$A^1$ is $NR^9$, O or S;

$A^2$ is N;

$R^5$ through $R^8$ are independently hydrogen, halogen, or $CF_3$; and $R^9$ is hydrogen, $(C_1\text{-}C_4)$-alkyl, or C(O)O-tert-butyl; or a pharmaceutically acceptable salt or solvate thereof.

In some embodiments, $X^1$ is $CR^1$, $X^4$ is $CR^4$, $X^2$ is S, and $X^3$ is a bond;

Y is C═O;
$A^1$ is S;
$A^2$ is N; and
$R^5$ through $R^8$ are independently hydrogen, halogen, or haloalkyl;
or a pharmaceutically acceptable salt or solvate thereof In some embodiments, $X^1$ and $X^4$ are N, and $X^2$ and $X^3$ are CH;
Y is C═O;
$A^1$ is S;
$A^2$ is N; and
$R^5$ through $R^8$ are independently hydrogen, halogen, or haloalkyl;
or a pharmaceutically acceptable salt or solvate thereof.

In some embodiments, Q is a bond and
$R^{10}$ is

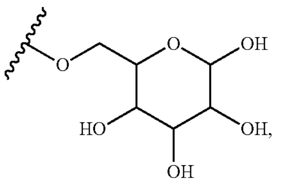

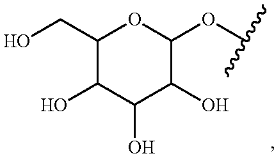
,
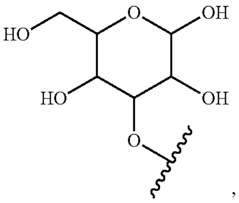
,
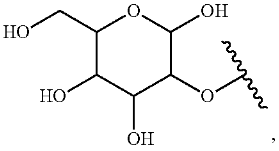
, or
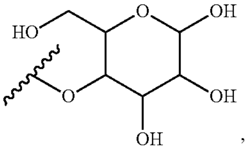
,

In some embodiments, Q is O—($C_1$-$C_6$)-alkyl, O—($C_1$-$C_6$)-hydroxyalkyl, O—($C_1$-$C_6$)-aminoalkyl, and $R^{10}$ is

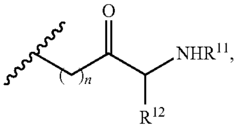
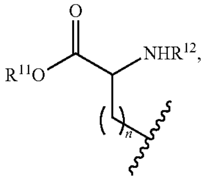
or
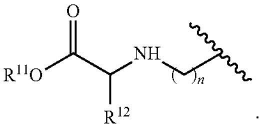
.

In some embodiments, Q is O—($C_1$-$C_6$)-aminoalkyl; $R^{10}$ is

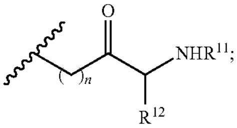

and n is 0.

In some embodiments, Q is NH—($C_1$-$C_6$)-alkyl, NH—($C_1$-$C_6$)-hydroxyalkyl, NH—($C_1$-$C_6$)-aminoalkyl, and $R^{10}$ is

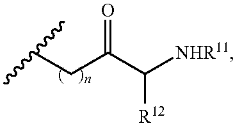
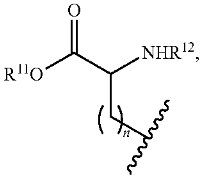
or
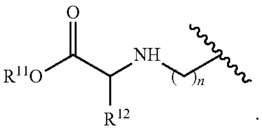
.

In some embodiments, Q is NH—($C_1$-$C_6$)-aminoalkyl; $R^{10}$ is

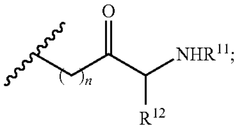

and n is 0.

In some embodiments, Q is O—($C_1$-$C_6$)-alkyl, or NH—($C_1$-$C_6$)-alkyl, or a bond; and $R^{10}$ is

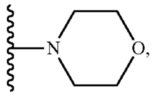 [SMILES: *N1CCOCC1]

aryl, heteroaryl, biaryl, benzyl, or heterocycle.

The disclosure relates to a compound of Formula (I-4)

(I-4)

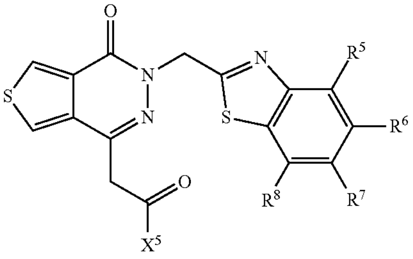

wherein $R^5$, $R^6$, $R^7$, $R^8$ and $X^5$ are as defined in Formula (I) and pharmaceutically acceptable salts thereof. In embodiments of compounds of Formula (I-4), $X^5$ is selected from a group consisting of

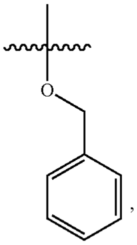
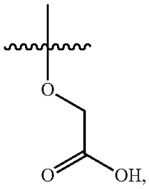
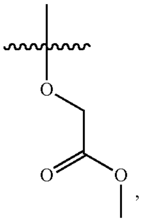
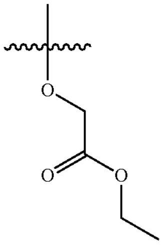
,
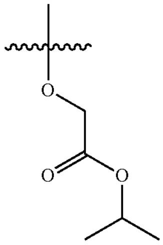
,
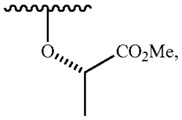
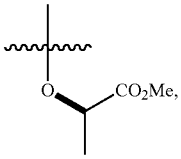
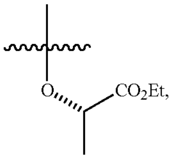
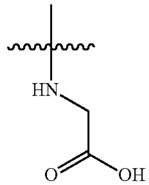
,
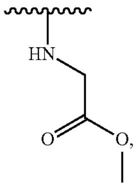
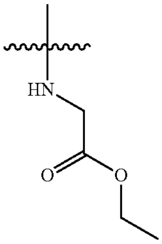
,
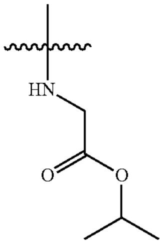
,
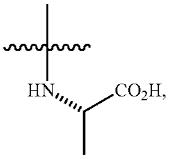
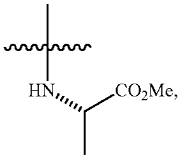
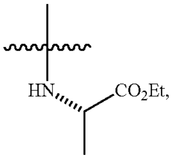
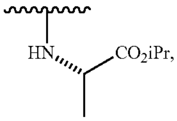
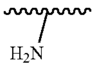
,
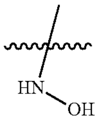
,
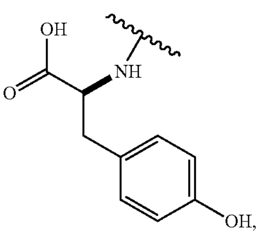
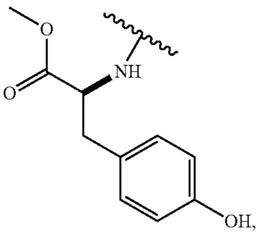
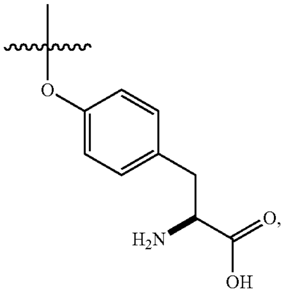
-continued
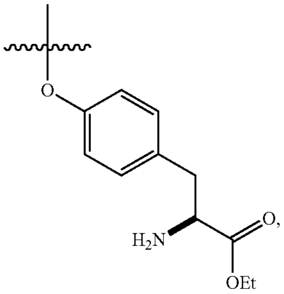
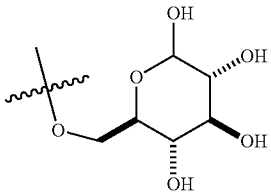
and
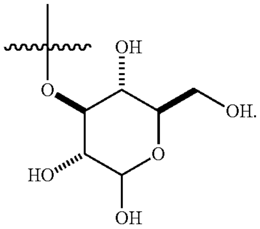
In certain preferred embodiments of compounds of Formula (I-4), $R^5$, $R^7$ and $R^8$ are each H; and $R^6$ is halogen of haloalkyl, preferably $R^6$ is trifluoromethyl, and $X^5$ is selected from a group consisting of
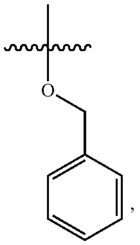
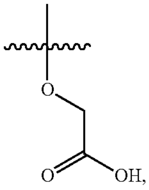
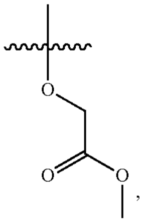
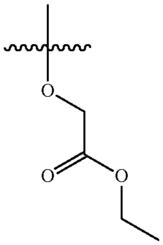
,
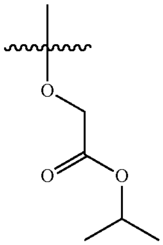
,
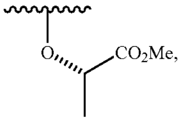
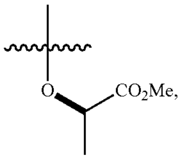
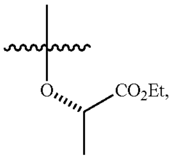
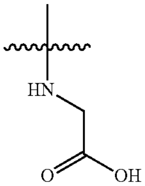
, -continued

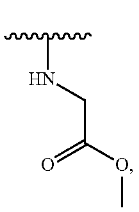

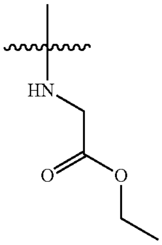

,

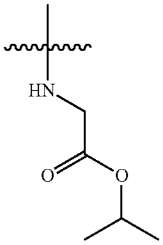

,

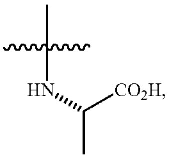

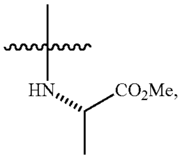

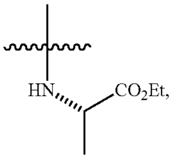

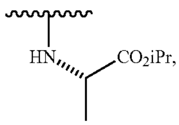

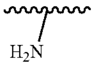

,

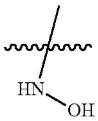

,

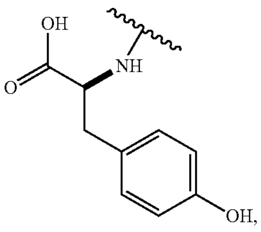

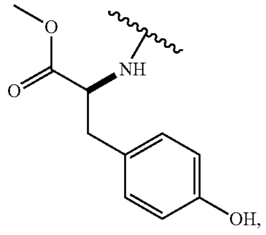

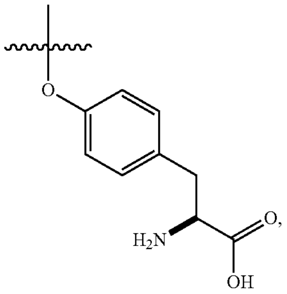

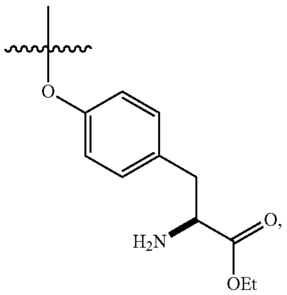

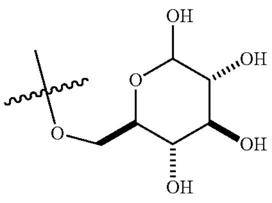

and

-continued

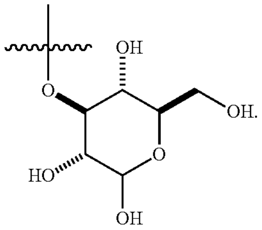

This disclosure further relates to compounds of Formula (II)

(II)

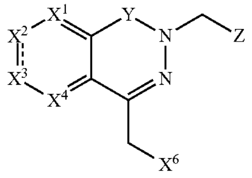

wherein, $X^1$ is N or $CR^1$;

$X^2$ is N, $CR^2$, or S;

$X^3$ is N, $CR^3$, or a bond;

$X^4$ is N or $CR^4$; with the proviso that when $X^2$ is S, $X^1$ is $CR^1$, $X^4$ is $CR^4$, and $X^3$ is a single bond; or that two or three of $X^1$, $X^2$, $X^3$, or $X^4$ are N;

Y is a bond, C═O, C═S, C═NH, or C═N($C_1$-$C_4$)-alkyl;

Z is

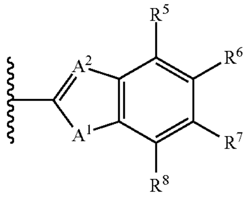

or

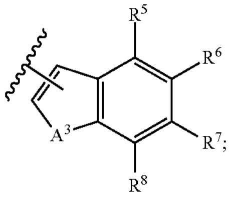

$A^1$ is $NR^9$, O, S or $CH_2$;

$A^2$ is N or CH;

$A^3$ is $NR^9$, O, or S;

$R^1$ through $R^8$ are independently hydrogen, halogen, cyano, acyl, haloalkyl, haloalkoxy, haloalkylthio, trifluoroacetyl, ($C_1$-$C_4$)-alkyl, ($C_1$-$C_4$)-alkoxy, ($C_1$-$C_4$)-alkylthio, ($C_1$-$C_4$)-alkylsulfinyl, or ($C_1$-$C_4$)-alkylsulfonyl; or two of $R^1$ through $R^4$ or two of $R^5$ through $R^8$ taken together are ($C_1$-$C_4$)-alkylenedioxy;

$R^9$ is hydrogen, $C_1$-$C_4$ alkyl, or C(O)O—($C_1$-$C_4$)-alkyl;

$X^6$ is $S(O)_2$—$OR^{13}$, $S(O)_2$—$NHR^{13}$, heteroaryl or heterocycloalkyl; and $R^{13}$ is H or ($C_1$-$C_6$)-alkyl; and pharmaceutically acceptable salts thereof.

This disclosure further relates to a compound selected from

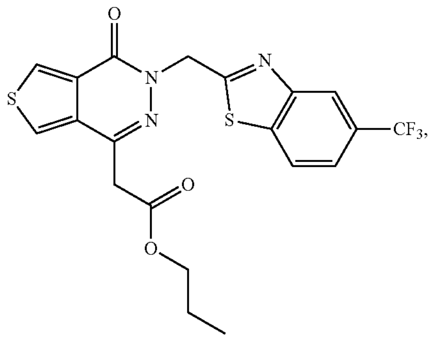
,

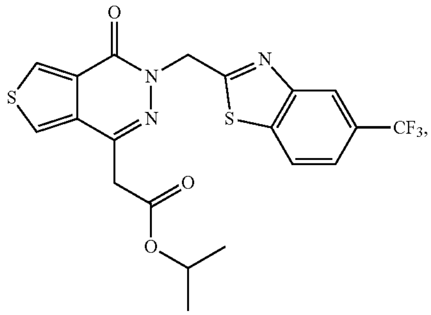
,

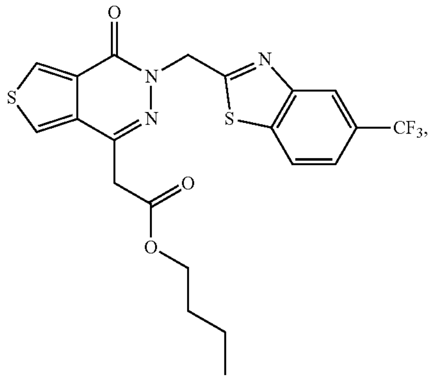
,

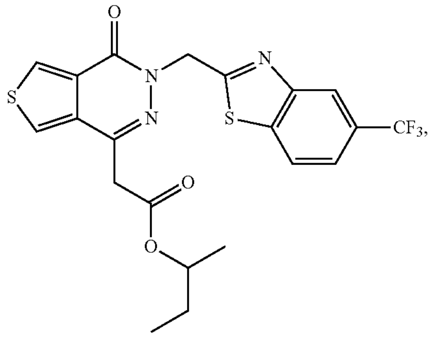
,

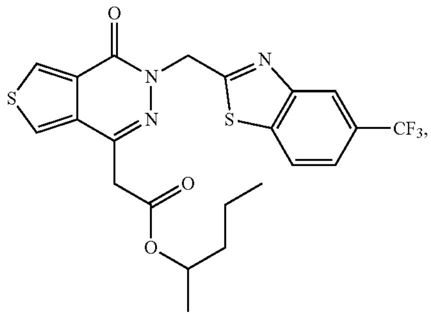
,

-continued (37)

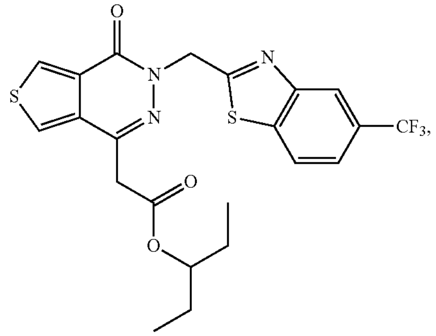
, and

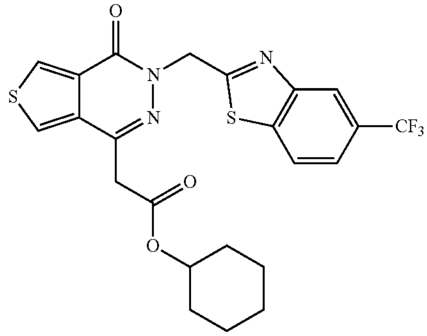

and pharmaceutically acceptable salts thereof.

This disclosure further relates to a compound selected from

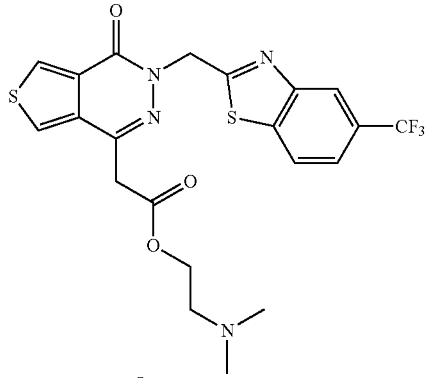
and

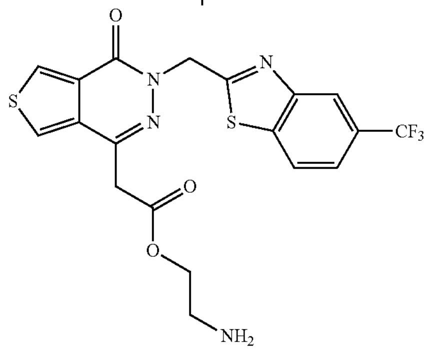

and pharmaceutically acceptable salts thereof.

In another aspect, the invention provides a pharmaceutical composition comprising a compound of Formula (I) or other compound disclosed herein and a pharmaceutically acceptable carrier.

In another aspect, the invention provides a method of inhibiting aldose reductase activity in a subject comprising administration of a therapeutically effective amount of a compound of Formula (I) or other compound disclosed herein to a subject in need thereof.

In some embodiments, the subject is a human.

In another aspect, the invention provides a method of treating a disorder in a subject comprising administration of a therapeutically effective amount of a compound of Formula (I) or other compound disclosed herein to a subject in need thereof.

In some embodiments, the disorder is stroke.

In some embodiments, the disorder is ischemic stroke.

In some embodiments, the disorder is tissue damage.

In some embodiments, the disorder is brain damage.

In some embodiments, the disorder is neural damage.

In some embodiments, the disorder is an autoimmune disease.

In some embodiments, the disorder is galactosemia.

In some embodiments, the disorder is phosphomannomutase 2-congenital disorder of glycosylation (PMM2-CDG).

This disclosure also relates to methods of treating complication of diabetes comprising administering a therapeutically effective amount of a compound of Formula (I) or other compound disclosed herein to a subject in need thereof. The complication of diabetes can be diabetic cardiomyopathy, diabetic retinopathy, diabetic neuropathy or diabetic nephropathy.

This disclosure also relates to methods of treating a cardiovascular disorder comprising administering a therapeutically effective amount of a compound of Formula (I) or other compound disclosed herein to a subject in need thereof. The cardiovascular disorder can be cardiomyopathy.

This disclosure also relates to methods for treating cutaneous aging comprising administering to a subject in need thereof a therapeutically effective amount of a compound of Formula (I) or other compound disclosed herein. The compound can be administered topically to the skin The present invention is based, in part, on certain discoveries which are described more fully in the Examples section of the present application. For example, the present invention is based, in part, on the discovery of compounds of Formula (I) or other compound disclosed herein and the aldose reductase inhibition exhibited by such compounds.

These and other embodiments of the invention are further described in the following sections of the application, including the Detailed Description, Examples, and Claims. Still other objects and advantages of the invention will become apparent by those of skill in the art from the disclosure herein, which are simply illustrative and not restrictive. Thus, other embodiments will be recognized by the ordinarily skilled artisan without departing from the spirit and scope of the invention.

DETAILED DESCRIPTION

Aldose reductase inhibitors are described, for example, in WO 2017/223179; U.S. Pat. Nos. 8,916,563; 5,677,342; 5,304,557; 5,155,259; 4,954,629; 4,939,140; U.S. Publication Number US 2006/0293265; Roy et al., in *Diabetes Research and Clinical Practice* 1990, 10(1), 91-97; CN101143868A; and Chatzopoulou et al., in *Expert Opin. Ther. Pat.* 2012, 22, 1303; and references cited therein; each of which hereby incorporated by reference in its entirety. Aldose reductase inhibitors include, for example, zopolrestat, epalrestat, ranirestat, berberine and sorbinil. A novel family of aldose reductase inhibitors has been discovered and is described herein. Surprisingly, this novel family comprises compounds that exhibit dramatically improved properties such as, for example, binding affinity, solubility, and polarity relative to other aldose reductase inhibitors such as, for example, zopolrestat. Compounds such as zopolrestat are described, for example in U.S. Pat. Nos. 4,939,140; 6,159,976; and 6,570,013; each of which hereby incorporated by reference in its entirety.

The compounds and/or compositions of the invention may be effective in treating, reducing, and/or suppressing complications related to aldose reductase activity such as, for example, atherosclerosis, neuropathy, retinopathy, nephropathy, cardiomyopathy, and multiple complications in diabetic patients. The compounds and/or compositions of the invention may also be effective in treating, reducing, and/or reducing cardiovascular and renal disorders in non-diabetic patients, as well as promoting healthy aging of skin or wound healing. Treatment using aldose reductase inhibitors is described in, e.g., CN102512407 A; WO2008002678A2; CN101143868A; Srivastava et al., in *Chem Biol Interact.* 2011, 30, 330; Hu et al., in *PLoS One* 2014, 9(2), e87096; Satoh et al., in *J Diabetes Res.* 2016, 2016, U.S. Pat. No. 5,383,797; Chatzopoulou et al., in *Expert Opin. Ther. Pat.* 2012, 22, 1303; each of which is hereby incorporated by reference in its entirety.

REAGENT ABBREVIATIONS $CDCl_3$ deuterated chloroform
CDI 1,1'-carbonyldiimidazole
$CD_3OD$ deuterated methanol
DMAP 4-(dimethylamino)pyridine
DMF N,N-dimethylformamide
$D_2O$ deuterium oxide
EDC-HCl N-(3-dimethylaminopropyl)-N'-ethylcarbodiimide hydrochloride
EtOAc ethyl acetate
EtOH ethanol
HCl hydrochloric acid
HOBT 1-hydroxybenzotriazole
$H_3PO_4$ phosphoric acid
$H_2SO_4$ sulfuric acid
LiOH lithium hydroxide
KOH potassium hydroxide
MeOH methanol
NaBr sodium bromide
$NaHCO_3$ sodium bicarbonate
NaI sodium iodide
NaOH sodium hydroxide
$Na_2SO_4$ sodium sulfate
NMP 1-methyl-2-pyrrolidinone
NHS N-hydroxysuccinimide
$^iPr_2NEt$ N,N-diisopropylethylamine
$^iPrOH$ isopropanol
TBAB tetrabutylammonium bromide
TBAC tetrabutylammonium chloride
TBAI tetrabutylammonium iodide
TEA triethylamine
TFA trifluoroacetic acid
THF tetrahydrofuran

ABBREVIATIONS AND DEFINITIONS

The term "aldose reductase inhibitor" refers to compounds and salts or solvates thereof that function by inhibiting the activity of the enzyme aldose reductase, which is primarily responsible for regulating metabolic reduction of aldoses. Exemplary aldoses include, but are not limited to, glucose or galactose, and their corresponding polyols, such as sorbitols and galactitols.

The term “compound of the invention” as used herein means a compound of Formula (I). The term is also intended to encompass salts, hydrates, pro-drugs and solvates thereof.

The term “composition(s) of the invention” as used herein means compositions comprising a compound of the invention, and salts, hydrates, pro-drugs, or solvates thereof. The compositions of the invention may further comprise other agents such as, for example, excipients, stabilants, lubricants, solvents, and the like.

The term “alkyl”, as used herein, unless otherwise indicated, refers to a monovalent aliphatic hydrocarbon radical having a straight chain, branched chain, monocyclic moiety, or polycyclic moiety or combinations thereof, wherein the radical is optionally substituted at one or more carbons of the straight chain, branched chain, monocyclic moiety, or polycyclic moiety or combinations thereof with one or more substituents at each carbon, where the one or more substituents are independently $C_1$-$C_{10}$ alkyl. Examples of “alkyl” groups include methyl, ethyl, propyl, isopropyl, butyl, isobutyl, sec-butyl, tert-butyl, pentyl, hexyl, heptyl, cyclopropyl, cyclobutyl, cyclopentyl, cyclohexyl, cycloheptyl, norbomyl, and the like.

The term “solvate” as used herein means a compound, or a pharmaceutically acceptable salt thereof, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a “hydrate.”

The term “pharmaceutically acceptable salt” is intended to include salts derived from inorganic or organic acids including, for example hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluroacetic, trichloroacetic, naphthalene-2 sulfonic and other acids; and salts derived from inorganic or organic bases including, for example sodium, potassium, calcium, magnesium, zinc, ammonia, lysine, arginine, histidine, polyhydroxylated amines, alkylamines, dialkylamines, trialkylamines, or tetrafluoroborate. Exemplary pharmaceutically acceptable salts are found, for example, in Berge, et al. (*J Pharm. Sci.* 1977, 66(1), 1; and U.S. Pat. Nos. 6,570,013 and 4,939,140; (each hereby incorporated by reference in its entirety). Pharmaceutically acceptable salts are also intended to encompass hemi-salts, wherein the ratio of compound:acid is respectively 2:1. Exemplary hemi-salts are those salts derived from acids comprising two carboxylic acid groups, such as malic acid, fumaric acid, maleic acid, succinic acid, tartaric acid, glutaric acid, oxalic acid, adipic acid and citric acid. Other exemplary hemi-salts are those salts derived from diprotic mineral acids such as sulfuric acid. Exemplary preferred hemi-salts include, but are not limited to, hemimaleate, hemifumarate, and hemisuccinate.

The term “acid” contemplates all pharmaceutically acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically acceptable aliphatic, alicyclic and aromatic carboxylic acids, dicarboxylic acids, tricarboxylic acids, and fatty acids. Preferred acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, fumaric acid, acetic acid, propionic acid, isopropionic acid, valeric acid, alpha-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tataric acid and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

As used herein the term “about” is used herein to mean approximately, roughly, around, or in the region of. When the term “about” is used in conjunction with a numerical range, it modifies that range by extending the boundaries above and below the numerical values set forth. In general, the term “about” is used herein to modify a numerical value above and below the stated value by a variance of 20 percent up or down (higher or lower).

An “effective amount”, “sufficient amount” or “therapeutically effective amount” as used herein is an amount of a compound that is sufficient to effect beneficial or desired results, including clinical results. As such, the effective amount may be sufficient, for example, to reduce or ameliorate the severity and/or duration of afflictions related to aldose reductase, or one or more symptoms thereof, prevent the advancement of conditions or symptoms related to afflictions related to aldose reductase, or enhance or otherwise improve the prophylactic or therapeutic effect(s) of another therapy. An effective amount also includes the amount of the compound that avoids or substantially attenuates undesirable side effects.

As used herein and as well understood in the art, “treatment” is an approach for obtaining beneficial or desired results, including clinical results. Beneficial or desired clinical results may include, but are not limited to, alleviation or amelioration of one or more symptoms or conditions, diminution of extent of disease or affliction, a stabilized (i.e., not worsening) state of disease or affliction, preventing spread of disease or affliction, delay or slowing of disease or affliction progression, amelioration or palliation of the disease or affliction state and remission (whether partial or total), whether detectable or undetectable. “Treatment” can also mean prolonging survival as compared to expected survival if not receiving treatment.

The phrase “in need thereof” refers to the need for symptomatic or asymptomatic relief from conditions related to aldose reductase activity or that may otherwise be relieved by the compounds and/or compositions of the invention.

Without wishing to be bound by any particular theory, it is believed that the compounds disclosed herein are prodrugs that can be converted into their corresponding free carboxylic acid forms in vivo following administration. The free carboxylic acid form may have greater aldose reductase inhibitor activity than the compounds disclosed herein. It is also believed that the compounds disclosed herein more readily cross the blood brain barrier into the central nervous system (e.g., via passive transcellular diffusion or by active transport, such as via activity of monocarboxylic acid transporter 1, large neutral amino acid transporter 1 (LAT1), glucose transporter 1 GLUT1, and the like).

In one embodiment, aldose reductase inhibitors described herein encompass compounds of Formula (I) or pharmaceutically acceptable salts, and pro-drugs thereof,

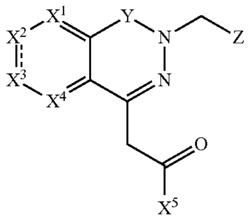

(I)

wherein, $X^1$ is N or $CR^1$;

$X^2$ is N, $CR^2$, or S;

$X^3$ is N, $CR^3$, or a bond;

$X^4$ is N or $CR^4$; with the proviso that when $X^2$ is S, $X^1$ is $CR^1$, $X^4$ is $CR^4$, and $X^3$ is a single bond; or that two or three of $X^1$, $X^2$, $X^3$, or $X^4$ are N;

Y is a bond, C═O, C═S, C═NH, or C═N($C_1$-$C_4$)-alkyl;

Z is

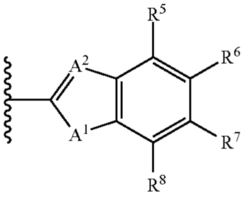

or

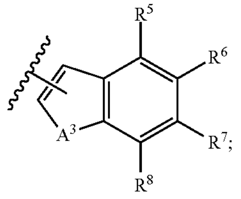

$A^1$ is $NR^9$, O, S or $CH_2$;

$A^2$ is N or CH;

$A^3$ is $NR^9$, O, or S;

$R^1$ through $R^8$ are independently hydrogen, halogen, cyano, acyl, haloalkyl, haloalkoxy, haloalkylthio, trifluoroacetyl, ($C_1$-$C_4$)-alkyl, ($C_1$-$C_4$)-alkoxy, ($C_1$-$C_4$)-alkylthio, ($C_1$-$C_4$)-alkylsulfinyl, or ($C_1$-$C_4$)-alkylsulfonyl; or two of $R^1$ through $R^4$ or two of $R^5$ through $R^8$ taken together are ($C_1$-$C_4$)-alkylenedioxy;

$R^9$ is hydrogen, $C_1$-$C_4$ alkyl, or C(O)O—($C_1$-$C_4$)-alkyl;

$X^5$ is Q-$R^{10}$;

Q is O, NH, O—($C_1$-$C_6$)-alkyl, O—($C_1$-$C_6$)-hydroxyalkyl, O—($C_1$-$C_6$)-aminoalkyl, O-aryl, O-heteroaryl, O-biaryl, O-benzyl, NH—($C_1$-$C_6$)-alkyl, NH—($C_1$-$C_6$)-hydroxyalkyl, NH—($C_1$-$C_6$)-aminoalkyl, NH-aryl, NH-heteroaryl, NH-biaryl, NH-benzyl, or a bond;

$R^{10}$ is

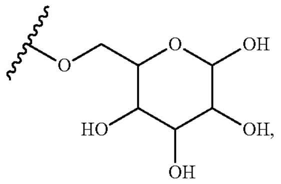

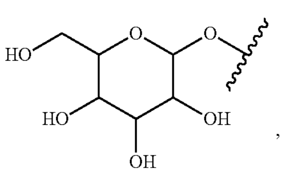

,

-continued

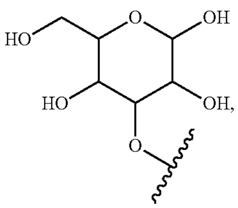

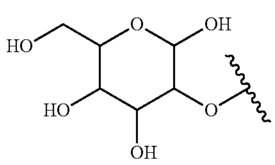

,

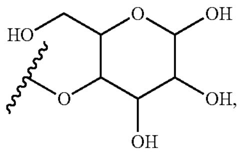

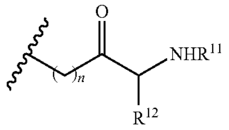

,

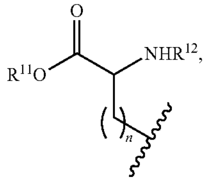

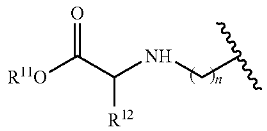

,

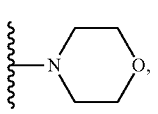

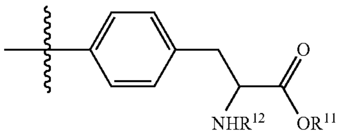

, aryl, heteroaryl, biaryl, benzyl, heterocycle, C(O)$OR^{11}$ and OH, with the proviso that when Q is NH, $R^{10}$ can also be H; and $R^{11}$ and $R^{12}$ are independently H or ($C_1$-$C_6$)-alkyl optionally substituted with one or more substituents selected from the group consisting of $OR^{13}$, $NHR^{13}$, $SR^{13}$, $CO_2R^{13}$, $CONHR^{13}$, benzyl, aryl, hydroxyaryl, indolyl, imidazolyl, and $NH(CNH)NH_2$;

or $R^{11}$ and $R^{12}$, taken together with the atoms to which they are attached, form a 3-7 membered heterocyclic ring;

$R^{13}$ is H or ($C_1$-$C_6$)-alkyl; and n is 0, 1, or 2; or a pharmaceutically acceptable salt thereof.

In Formula (I), $R^{10}$ can be bonded to any substitutable atom in Q. For example, when Q is O—($C_1$-$C_6$)alkyl, $R^{10}$ can be bonded to any of the carbon atoms in the alkyl.

It will be recognized by those of skill in the art that the designation of Z is

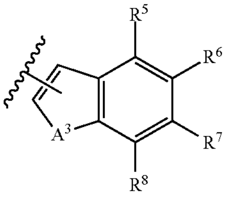

indicates that Z is

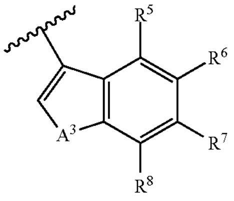

or Z is

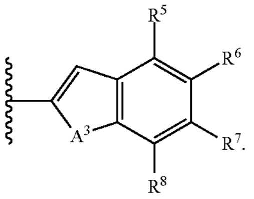

It will be recognized by those of skill in the art that the designation of Z is

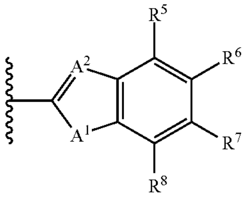

or Z

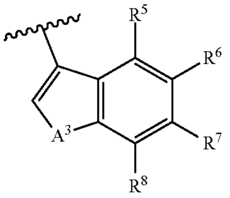

or

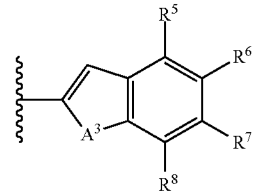

Z is indicates that when Z is

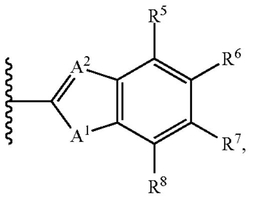

the compounds of Formula (I) are understood to encompass (I-1)

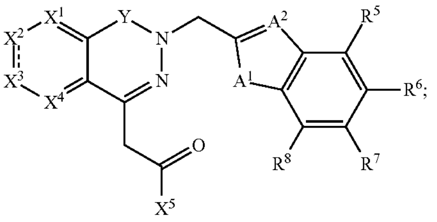

when Z is

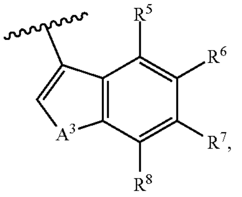

the compounds of Formula (I) are understood to encompass (I-2)

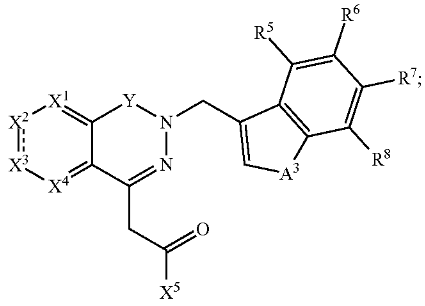

and when Z is

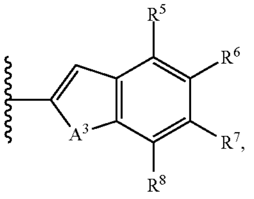

the compounds of Formula (I) are understood to encompass (I-3)

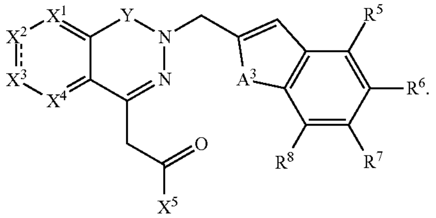

In certain embodiments, $X^1$ and $X^4$ are N, and $X^2$ and $X^3$ are CH. In certain embodiments, $X^1$ is $CR^1$, $X^4$ is $CR^4$, $X^2$ is S, and $X^3$ is a bond. In certain embodiments, $X^1$ and $X^4$ are each CH, $X^2$ is S, and $X^3$ is a bond.

In certain embodiments, $R^1$ and $R^4$ are hydrogen. In certain embodiments, $R^1$ and $R^4$ are halogen. In certain embodiments, $R^1$ and $R^4$ are Cl.

In certain embodiments, $R^1$ and $R^4$ are independently hydrogen or halogen. In certain embodiments, $R^1$ is hydrogen and $R^4$ is Cl. In certain embodiments, $R^1$ is Cl and $R^4$ is hydrogen.

In certain embodiments, Q is O or NH. In certain embodiments, Q is O. In certain embodiments, Q is NH. In certain embodiments, Q is a bond.

In certain embodiments, Q is O—($C_1$-$C_6$)-alkyl, O—($C_1$-$C_6$)-hydroxyalkyl, O—($C_1$-$C_6$)-aminoalkyl. In certain embodiments, Q is O—($C_1$-$C_4$)-alkyl, O—($C_1$-$C_4$)-hydroxyalkyl, O—($C_1$-$C_4$)-aminoalkyl. In certain embodiments, Q is O—($C_1$-$C_3$)-alkyl, O—($C_1$-$C_3$)-hydroxyalkyl, O—($C_1$-$C_3$)-aminoalkyl. In certain embodiments, Q is O—($C_1$-$C_2$)-alkyl, O—($C_1$-$C_2$)-hydroxyalkyl, O—($C_1$-$C_2$)-aminoalkyl. In certain embodiments, Q is O—($C_1$-$C_6$)-alkyl. In certain embodiments, Q is O—($C_1$-$C_6$)-hydroxyalkyl. In certain embodiments, Q is O—($C_1$-$C_6$)-aminoalkyl.

In certain embodiments, Q is O—($C_1$-$C_6$)-n-alkyl, O—($C_1$-$C_6$)-hydroxy-n-alkyl, O—($C_1$-$C_6$)-amino-n-alkyl. In certain embodiments, Q is O—($C_1$-$C_4$)-n-alkyl, O—($C_1$-$C_4$)-hydroxy-n-alkyl, O—($C_1$-$C_4$)-amino-n-alkyl. In certain embodiments, Q is O—($C_1$-$C_3$)-n-alkyl, O—($C_1$-$C_3$)-hydroxy-n-alkyl, O—($C_1$-$C_3$)-amino-n-alkyl. In certain embodiments, Q is O—($C_1$-$C_2$)-n-alkyl, O—($C_1$-$C_2$)-hydroxy-n-alkyl, O—($C_1$-$C_2$)-amino-n-alkyl. In certain embodiments, Q is O—($C_1$-$C_6$)-n-alkyl. In certain embodiments, Q is O—($C_1$-$C_6$)-hydroxy-n-alkyl. In certain embodiments, Q is O—($C_1$-$C_6$)-amino-n-alkyl.

In certain embodiments, Q is NH—($C_1$-$C_6$)-alkyl, NH—($C_1$-$C_6$)-hydroxyalkyl, NH—($C_1$-$C_6$)-aminoalkyl. In certain embodiments, Q is NH—($C_1$-$C_4$)-alkyl, NH—($C_1$-$C_4$)-hydroxyalkyl, NH—($C_1$-$C_4$)-aminoalkyl. In certain embodiments, Q is NH—($C_1$-$C_3$)-alkyl, NH— ($C_1$-$C_3$)-hydroxyalkyl, NH—($C_1$-$C_3$)-aminoalkyl. In certain embodiments, Q is NH—($C_1$-$C_2$)-alkyl, NH—($C_1$-$C_2$)-hydroxyalkyl, NH—($C_1$-$C_2$)-aminoalkyl. In certain embodiments, Q is NH—($C_1$-$C_6$)-alkyl. In certain embodiments, Q is NH—($C_1$-$C_6$)-hydroxyalkyl. In certain embodiments, Q is NH—($C_1$-$C_6$)-aminoalkyl.

In certain embodiments, Q is NH—($C_1$-$C_6$)-n-alkyl, NH—($C_1$-$C_6$)-hydroxy-n-alkyl, NH—($C_1$-$C_6$)-amino-n-alkyl. In certain embodiments, Q is NH—($C_1$-$C_4$)-n-alkyl, NH—($C_1$-$C_4$)-hydroxy-n-alkyl, NH—($C_1$-$C_4$)-amino-n-alkyl. In certain embodiments, Q is NH—($C_1$-$C_3$)-n-alkyl, NH—($C_1$-$C_3$)-hydroxy-n-alkyl, NH—($C_1$-$C_3$)-amino-n-alkyl. In certain embodiments, Q is NH—($C_1$-$C_2$)-n-alkyl, NH—($C_1$-$C_2$)-hydroxy-n-alkyl, NH—($C_1$-$C_2$)-amino-n-alkyl. In certain embodiments, Q is NH—($C_1$-$C_6$)-n-alkyl. In certain embodiments, Q is NH—($C_1$-$C_6$)-hydroxy-n-alkyl. In certain embodiments, Q is NH—($C_1$-$C_6$)-amino-n-alkyl.

In certain embodiments, Q is O-aryl, O-heteroaryl, O-biaryl, or O-benzyl. In certain embodiments, Q is O-aryl, O-heteroaryl, or O-benzyl. In certain embodiments, Q is O-aryl or O-benzyl. In certain embodiments, Q is O-aryl or O-heteroaryl. In certain embodiments, Q is O-aryl. In certain embodiments, Q is O-heteroaryl. In certain embodiments, Q is O-biaryl. In certain embodiments, Q is O-benzyl.

In certain embodiments, Q is NH-aryl, NH-heteroaryl, NH-biaryl, or NH-benzyl. In certain embodiments, Q is NH-aryl, NH-heteroaryl, or NH-benzyl. In certain embodiments, Q is NH-aryl or NH-benzyl. In certain embodiments, Q is NH-aryl or NH-heteroaryl. In certain embodiments, Q is NH-aryl. In certain embodiments, Q is NH-heteroaryl. In certain embodiments, Q is NH-biaryl. In certain embodiments, Q is NH-benzyl.

In certain embodiments, $R^{10}$ is

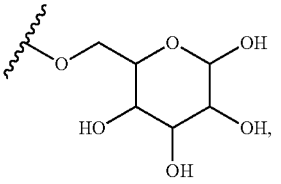 [SMILES: *OCC1OC(O)C(O)C(O)C1O]

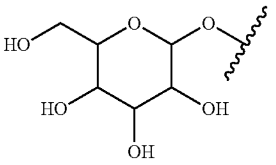

,

-continued

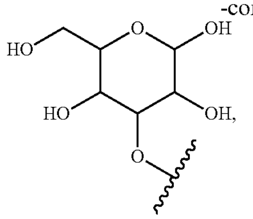

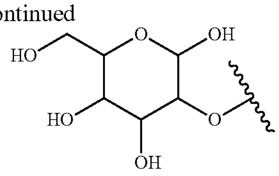

,

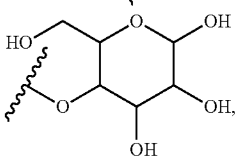

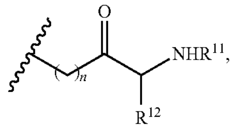

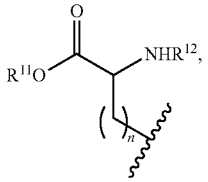

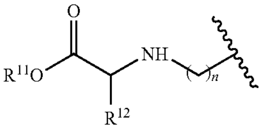

,

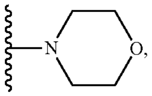

aryl, heteroaryl, biaryl, benzyl, or heterocycle.

In certain embodiments, $R^{10}$ is

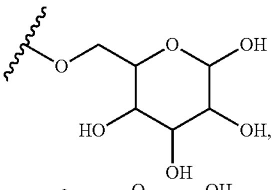

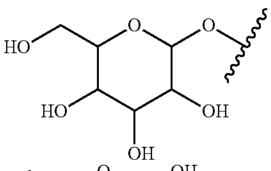

,

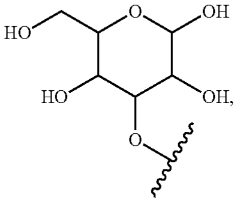

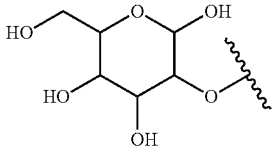

, or

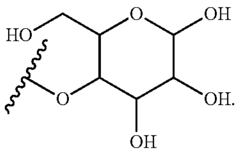

In certain embodiments, $R^{10}$ is

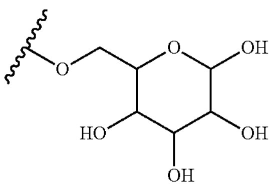

or

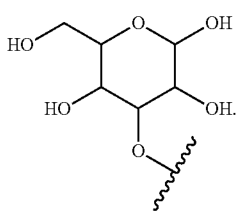

In certain embodiments, $R^{10}$ is
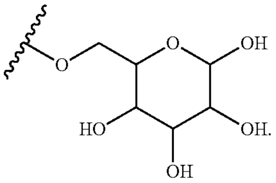
In certain embodiments, $R^{10}$ is
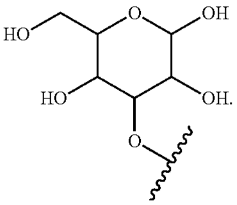 [SMILES: *OC1C(O)C(O)OC(CO)C1O]
In certain embodiments, $R^{10}$ is
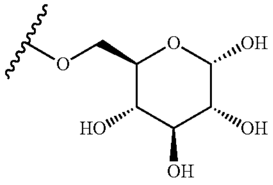
or
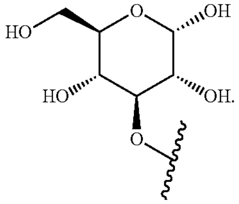
In certain embodiments, $R^{10}$ is
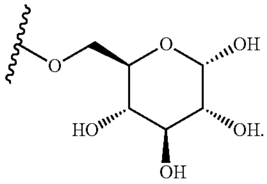 [SMILES: *OC[C@H]1O[C@H](O)[C@H](O)[C@@H](O)[C@@H]1O]
In certain embodiments, $R^{10}$ is
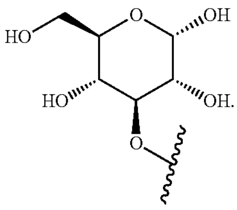 [SMILES: *O[C@@H]1[C@@H](O)[C@@H](O)O[C@H](CO)[C@H]1O]
In certain embodiments, $R^{10}$ is
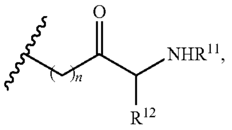
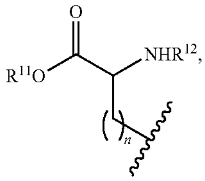
or
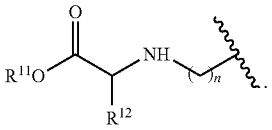
In certain embodiments, $R^{10}$ is
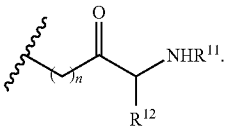
In certain embodiments, $R^{10}$ is
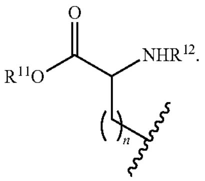
In certain embodiments, $R^{10}$ is
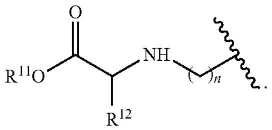
In certain embodiments, $R^{10}$ is
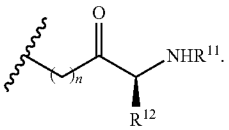
In certain embodiments, $R^{10}$ is
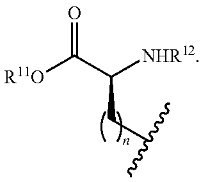

In certain embodiments, $R^{10}$ is

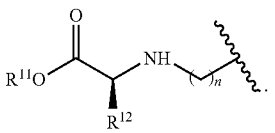

In certain embodiments, $R^{10}$ is

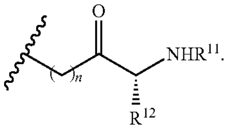

In certain embodiments, $R^{10}$ is

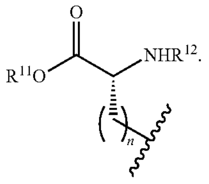

In certain embodiments, $R^{10}$ is

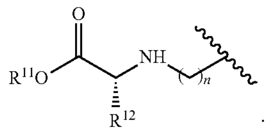

In certain embodiments, $R^{10}$ is

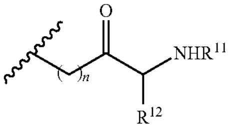

and n is 0. In certain embodiments, $R^{10}$ is

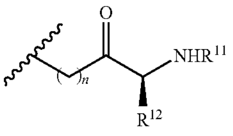

and n is 0. In certain embodiments, $R^{10}$ is

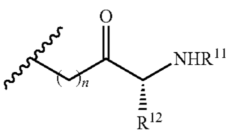

and n is 0.

In certain embodiments, $R^{10}$ is

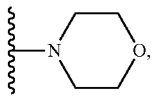

aryl, heteroaryl, biaryl, benzyl, or heterocycloalkyl. In certain embodiments, $R^{10}$ is aryl, heteroaryl, biaryl, benzyl, or heterocycloalkyl. In certain embodiments, $R^{10}$ is aryl, heteroaryl, benzyl, or heterocycloalkyl. In certain embodiments, $R^{10}$ is aryl or benzyl. In certain embodiments, $R^{10}$ is heteroaryl. In certain embodiments, $R^{10}$ is heterocycloalkyl.

In certain embodiments, $R^{11}$ and $R^{12}$ are independently H or $(C_1$-$C_6)$-alkyl optionally substituted with one or more substituents selected from the group consisting of $OR^{13}$, $NHR^{13}$, $SR^{13}$, $CO_2R^{13}$, $CONHR^{13}$, benzyl, aryl, hydroxyaryl, indolyl, imidazolyl, and $NH(CNH)NH_2$. In certain embodiments, $R^{11}$ and $R^{12}$, taken together with the atoms to which they are attached, form a 3-7 membered heterocyclic ring.

In certain embodiments, $R^{11}$ and $R^{12}$ are independently H or $(C_1$-$C_6)$-alkyl. In certain embodiments, $R^{11}$ and $R^{12}$ are independently H or $(C_1$-$C_4)$-alkyl. In certain embodiments, $R^{11}$ and $R^{12}$ are independently H or $(C_1$-$C_3)$-alkyl. In certain embodiments, $R^{11}$ and $R^{12}$ are independently H or $(C_1$-$C_2)$-alkyl.

In certain embodiments, $R^{11}$ and $R^{12}$ are independently H or $(C_1$-$C_6)$-alkyl optionally substituted with one or more substituents selected from the group consisting of $OR^{13}$, $NHR^{13}$, $SR^{13}$, $CO_2R^{13}$, $CONHR^{13}$, benzyl, aryl, hydroxyaryl, indolyl, imidazolyl, and $NH(CNH)NH_2$. In certain embodiments, $R^{11}$ and $R^{12}$ are independently H or $(C_1$-$C_4)$-alkyl optionally substituted with one or more substituents selected from the group consisting of $OR^{13}$, $NHR^{13}$, $SR^{13}$, $CO_2R^{13}$, $CONHR^{13}$, benzyl, aryl, hydroxyaryl, indolyl, imidazolyl, and $NH(CNH)NH_2$. In certain embodiments, $R^{11}$ and $R^{12}$ are independently H or $(C_1$-$C_3)$-alkyl optionally substituted with one or more substituents selected from the group consisting of $OR^{13}$, $NHR^{13}$, $SR^{13}$, $CO_2R^{13}$, $CONHR^{13}$, benzyl, aryl, hydroxyaryl, indolyl, imidazolyl, and $NH(CNH)NH_2$. In certain embodiments, $R^{11}$ and $R^{12}$ are independently H or $(C_1$-$C_2)$-alkyl optionally substituted with one or more substituents selected from the group consisting of $OR^{13}$, $NHR^{13}$, $SR^{13}$, $CO_2R^{13}$, $CONHR^{13}$, benzyl, aryl, hydroxyaryl, indolyl, imidazolyl, and $NH(CNH)NH_2$.

In certain embodiments, $R^{11}$ and $R^{12}$ are H; n is 0; and $R^{10}$ is

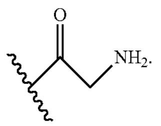 [SMILES: *C(=O)CN]

In certain embodiments, $R^{11}$ is H; $R^{12}$ is $CH_3$; n is 0; and $R^{10}$ is

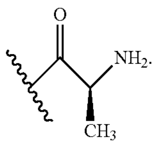 [SMILES: *C(=O)[C@H](C)N]

In certain embodiments, $R^{11}$ is H; $R^{12}$ is $(C_1\text{-}C_3)$-alkyl; n is 0; and $R^{10}$ is

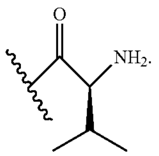 [SMILES: *C(=O)[C@@H](N)C(C)C]

In certain embodiments, $R^{11}$ is H; $R^{12}$ is $(C_1\text{-}C_4)$-alkyl; n is 0; and $R^{10}$ is

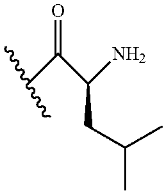

or

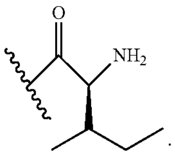

In certain embodiments, $R^{10}$ is

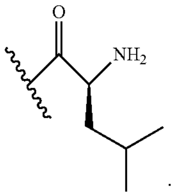 [SMILES: *C(=O)[C@@H](N)CC(C)C]

In certain embodiments, $R^{10}$ is

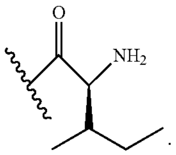 [SMILES: *C(=O)[C@@H](N)C(C)CC]

In certain embodiments, $R^{11}$ is H; $R^{12}$ is $CH_2OH$; n is 0; and $R^{10}$ is

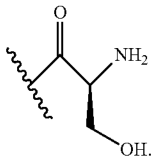 [SMILES: *C(=O)[C@@H](N)CO]

In certain embodiments, $R^{11}$ is H; $R^{12}$ is $CH(CH_3)(OH)$; n is 0; and $R^{10}$ is

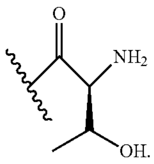 [SMILES: *C(=O)[C@@H](N)C(C)O]

In certain embodiments, $R^{11}$ is H; $R^{12}$ is $CH_2SH$; n is 0; and $R^{10}$ is is

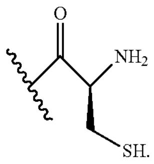 [SMILES: *C(=O)[C@@H](N)CS]

In certain embodiments, $R^{11}$ is H; $R^{12}$ is $CH_2CH_2SCH_3$; n is 0; and $R^{10}$ is

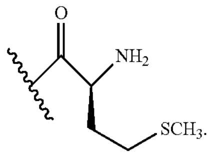 [SMILES: *C(=O)[C@@H](N)CCSC]

In certain embodiments, $R^{11}$ is H; $R^{12}$ is benzyl; n is 0; and $R^{10}$ is

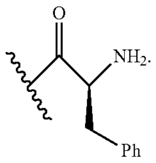 [SMILES: *C(=O)[C@@H](N)Cc1ccccc1]

In certain embodiments, $R^{11}$ is H; $R^{12}$ is 4-hydroxybenzyl; n is 0; and $R^{10}$ is

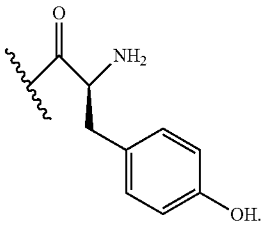 [SMILES: *C(=O)[C@@H](N)Cc1ccc(O)cc1]

In certain embodiments, $R^{11}$ is H; $R^{12}$ is 2-indolyl; n is 0; and $R^{10}$ is

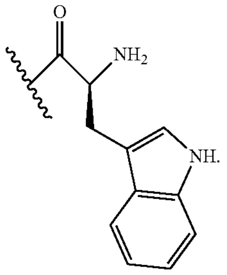 [SMILES: *C(=O)[C@@H](N)Cc1c[nH]c2ccccc12]

In certain embodiments, $R^{11}$ is H; $R^{12}$ is $CH_2CO_2H$; n is 0; and $R^{10}$ is

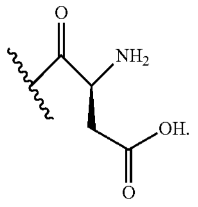 [SMILES: *C(=O)[C@@H](N)CC(=O)O]

In certain embodiments, $R^{11}$ is H; $R^{12}$ is $CH_2CH_2CO_2H$; n is 0; and $R^{10}$ is

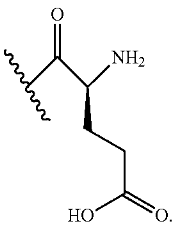 [SMILES: *C(=O)[C@@H](N)CCC(=O)O]

In certain embodiments, $R^{11}$ is H; $R^{12}$ is $CH_2CONH_2$; n is 0; and $R^{10}$ is

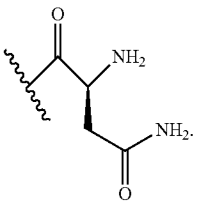 [SMILES: *C(=O)[C@@H](N)CC(N)=O]

In certain embodiments, $R^{11}$ is H; $R^{12}$ is $CH_2CH_2CONH_2$; n is 0; and $R^{10}$ is

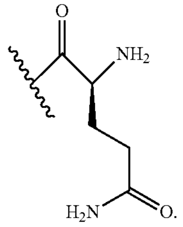 [SMILES: *C(=O)[C@@H](N)CCC(N)=O]

In certain embodiments, $R^{11}$ is H; $R^{12}$ is 5-imidazolyl; n is 0; and $R^{10}$ is

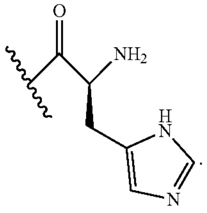 [SMILES: *C(=O)[C@@H](N)Cc1cnc[nH]1]

In certain embodiments, $R^{11}$ is H; $R^{12}$ is $CH_2(CH_2)_3NH_2$; n is 0; and $R^{10}$ is

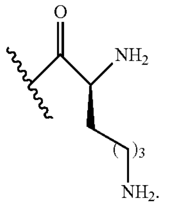

In certain embodiments, $R^{11}$ is H; $R^{12}$ is $CH_2(CH_2)_2NH(CNH)NH_2$; n is 0, and $R^{10}$ is

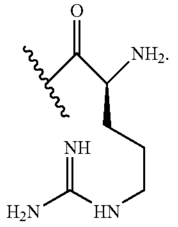

In certain embodiments, $R^{11}$ is $CH_3$ and $R^{12}$ is $CH_2CH_3$ and $R^{11}$ and $R^{12}$, taken together with the atoms to which they are attached, form a pyrrolidine ring; n is 0; and $R^{10}$ is

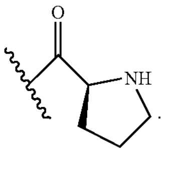 [SMILES: *C(=O)[C@@H]1CCCN1]

In certain embodiments, $R^{11}$ is $CH_2CH_3$ and $R^{12}$ is $CH_3$ and $R^{11}$ and $R^{12}$, taken together with the atoms to which they are attached, form a pyrrolidine ring; n is 0; and $R^0$ is

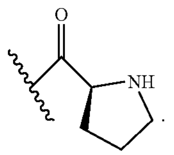 [SMILES: *C(=O)[C@@H]1CCCN1]

In certain embodiments, $R^{11}$ and $R^{12}$, taken together with the atoms to which they are attached, form a 3-7 membered heterocyclic ring. In certain embodiments, $R^{11}$ and $R^{12}$, taken together with the atoms to which they are attached, form a 3-membered heterocyclic ring. In certain embodiments, $R^{11}$ and $R^{12}$, taken together with the atoms to which they are attached, form a 4-membered heterocyclic ring. In certain embodiments, $R^{11}$ and $R^{12}$, taken together with the atoms to which they are attached, form a 5-membered heterocyclic ring. In certain embodiments, $R^{11}$ and $R^{12}$, taken together with the atoms to which they are attached, form a 6-membered heterocyclic ring. In certain embodiments, $R^{11}$ and $R^{12}$, taken together with the atoms to which they are attached, form a 7-membered heterocyclic ring.

In certain embodiments, $R^{13}$ is H or $(C_1$-$C_6)$-alkyl. In certain embodiments, $R^{13}$ is H. In certain embodiments, $R^{13}$ $(C_1$-$C_6)$-alkyl. In certain embodiments, $R^{13}$ $(C_1$-$C_4)$-alkyl. In certain embodiments, $R^{13}$ $(C_1$-$C_3)$-alkyl. In certain embodiments, $R^{13}$ $(C_1$-$C_2)$-alkyl.

In certain embodiments, n is 0, 1, or 2. In certain embodiments, n is 0. In certain embodiments, n is 1. In certain embodiments, n is 2.

In certain embodiments, Z is R

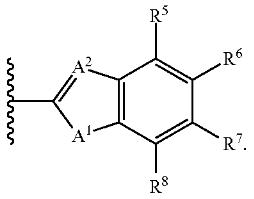

In certain embodiments, Z is

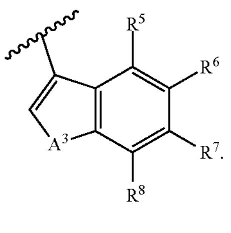

In certain embodiments, Z is

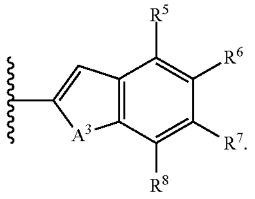

In certain embodiments, $R^5$ through $R^8$ are independently hydrogen, halogen, cyano, acyl, haloalkyl, haloalkoxy, haloalkylthio, trifluoroacetyl, $(C_1$-$C_4)$-alkyl, $(C_1$-$C_4)$-alkoxy, $(C_1$-$C_4)$-alkylthio, $(C_1$-$C_4)$-alkylsulfinyl, or $(C_1$-$C_4)$-alkylsulfonyl.

In certain embodiments, $R^5$ through $R^8$ are independently hydrogen, halogen or haloalkyl. In certain embodiments, $R^5$ through $R^8$ are independently hydrogen, halogen or trihaloalkyl.

In certain embodiments, $R^5$ through $R^8$ are hydrogen. In certain embodiments, $R^5$, $R^7$, and $R^8$ are hydrogen.

In certain embodiments, $R^6$ is hydrogen, halogen or haloalkyl. In certain embodiments, $R^6$ is hydrogen. In certain embodiments, $R^6$ is halogen. In certain embodiments, $R^6$ is haloalkyl. In certain embodiments, $R^6$ is $CF_3$.

In certain embodiments, $R^5$ through $R^8$ are hydrogen. In certain embodiments, $R^5$, $R^7$, $R^8$ are hydrogen and $R^6$ is halogen or haloalkyl. In certain embodiments, $R^5$, $R^7$, $R^8$ are hydrogen and $R^6$ is haloalkyl. In certain embodiments, $R^5$, $R^7$, $R^8$ are hydrogen and $R^6$ is $CF_3$. In certain embodiments, $R^5$, $R^7$, $R^8$ are hydrogen and $R^6$ is halogen. In certain embodiments, $R^5$, $R^7$, $R^8$ are hydrogen and $R^6$ is F. In certain embodiments, $R^5$, $R^7$, $R^8$ are hydrogen and $R^6$ is Cl.

In certain embodiments, Y is C═O, C═S, C═NH, or C═N$(C_1$-$C_4)$-alkyl. In certain embodiments, Y is C═O or C═S. In certain embodiments, Y is C═O. In certain embodiments, Y is C═S. In certain embodiments, Y is C═NH, or C═N$(C_1$-$C_4)$-alkyl.

In certain embodiments, $A^1$ is $NR^9$, O, S or $CH_2$. In certain embodiments, $A^1$ is $NR^9$, O, or S. In certain embodiments, $A^1$ is $NR^9$, S or $CH_2$. In certain embodiments, $A^1$ is $NR^9$ or O. In certain embodiments, $A^1$ is $NR^9$ or S. In certain embodiments, $A^1$ is $NR^9$. In certain embodiments, $A^1$ is O. In certain embodiments, $A^1$ is S.

In certain embodiments, $A^2$ is N or CH. In certain embodiments, $A^2$ is N. In certain embodiments, $A^2$ is CH.

In certain embodiments, $A^3$ is $NR^9$, O, or S. In certain embodiments, $A^3$ is O. In certain embodiments, $A^3$ is S. In certain embodiments, $A^3$ is $NR^9$.

In certain embodiments, $R^9$ is hydrogen, $C_1$-$C_4$ alkyl, or C(O)O—$(C_1$-$C_4)$-alkyl. In certain embodiments, $R^9$ is hydrogen. In certain embodiments, $R^9$ is $C_1$-$C_4$ alkyl. In certain embodiments, $R^9$ is $C_1$-$C_3$ alkyl. In certain embodiments, $R^9$ is $C_1$-$C_2$ alkyl. In certain embodiments, $R^9$ is $C_1$-$C_4$ n-alkyl. In certain embodiments, $R^9$ is $C_1$-$C_3$ n-alkyl. In certain embodiments, $R^9$ is C(O)O—$(C_1$-$C_4)$-alkyl. In certain embodiments, $R^9$ is C(O)O—$(C_1$-$C_3)$-alkyl. In certain embodiments, $R^9$ is C(O)O—$(C_1$-$C_2)$-alkyl. In certain embodiments, $R^9$ is C(O)O—$(C_1$-$C_4)$-n-alkyl. In certain embodiments, $R^9$ is C(O)O—$(C_1$-$C_3)$-n-alkyl.

In certain embodiments, $X^1$ and $X^4$ are N, and $X^2$ and $X^3$ are CH; or $X^1$ is $CR^1$, $X^4$ is $CR^4$, $X^2$ is S, and $X^3$ is a bond.

In certain embodiments, Y is C═0;

$A^1$ is $NR^9$, O, or S;

$A^2$ is N;

$A^3$ is O, or S; and $R^5$ through $R^8$ are independently hydrogen, halogen, cyano, acyl, haloalkyl, haloalkoxy, haloalkylthio, trifluoroacetyl, $(C_1\text{-}C_4)$-alkyl, $(C_1\text{-}C_4)$-alkoxy, $(C_1\text{-}C_4)$-alkylthio, $(C_1\text{-}C_4)$-alkylsulfinyl, or $(C_1\text{-}C_4)$-alkylsulfonyl;

or a pharmaceutically acceptable salt or solvate thereof.

In certain embodiments, $R^5$ through $R^8$ are independently hydrogen, halogen, or haloalkyl; and $R^9$ is hydrogen, $(C_1\text{-}C_4)$-alkyl, or C(O)O-tert-butyl; or a pharmaceutically acceptable salt or solvate thereof.

In certain embodiments, Z is

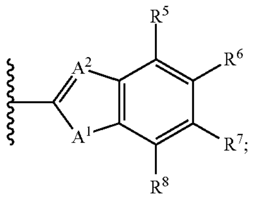

Y is C═O;

$A^1$ is $NR^9$, O, or S;

$A^2$ is N;

$R^5$ through $R^8$ are independently hydrogen, halogen, cyano, acyl, haloalkyl, haloalkoxy, haloalkylthio, $(C_1\text{-}C_4)$-alkyl, $(C_1\text{-}C_4)$-alkoxy, $(C_1\text{-}C_4)$-alkylthio, $(C_1\text{-}C_4)$-alkylsulfinyl, or $(C_1\text{-}C_4)$-alkylsulfonyl; and $R^9$ is hydrogen, $C_1\text{-}C_4$ alkyl, or C(O)O—$(C_1\text{-}C_4)$-alkyl; or a pharmaceutically acceptable salt or solvate thereof.

In certain embodiments, Y is C═0;

$A^1$ is $NR^9$, O, or S;

$A^2$ is N;

$R^5$ through $R^8$ are independently hydrogen, halogen, cyano, acyl, haloalkyl, haloalkoxy, haloalkylthio, $(C_1\text{-}C_4)$-alkyl, $(C_1\text{-}C_4)$-alkoxy, $(C_1\text{-}C_4)$-alkylthio, $(C_1\text{-}C_4)$-alkylsulfinyl, or $(C_1\text{-}C_4)$-alkylsulfonyl; and $R^9$ is hydrogen, $C_1\text{-}C_4$ alkyl, or C(O)O—$(C_1\text{-}C_4)$-alkyl; or a pharmaceutically acceptable salt or solvate thereof.

In certain embodiments, Y is C═O;

$A^1$ is $NR^9$, O or S;

$A^2$ is N;

$R^5$ through $R^8$ are independently hydrogen, halogen, or haloalkyl; and $R^9$ is hydrogen, $(C_1\text{-}C_4)$-alkyl, or C(O)O-tert-butyl; or a pharmaceutically acceptable salt or solvate thereof.

In certain embodiments, Y is C═0;

$A^1$ is $NR^9$, O or S;

$A^2$ is N;

$R^5$ through $R^8$ are independently hydrogen, halogen, or $CF_3$; and $R^9$ is hydrogen, $(C_1\text{-}C_4)$-alkyl, or C(O)O-tert-butyl; or a pharmaceutically acceptable salt or solvate thereof.

In certain embodiments, $X^1$ is $CR^1$, $X^4$ is $CR^4$, $X^2$ is S, and $X^3$ is a bond;

Y is C═O;

$A^1$ is S;

$A^2$ is N; and $R^5$ through $R^8$ are independently hydrogen, halogen, or haloalkyl;

or a pharmaceutically acceptable salt or solvate thereof

In certain embodiments, $X^1$ and $X^4$ are N, and $X^2$ and $X^3$ are CH;

Y is C═O;

$A^1$ is S;

$A^2$ is N; and $R^5$ through $R^8$ are independently hydrogen, halogen, or haloalkyl;

or a pharmaceutically acceptable salt or solvate thereof.

In certain embodiments, Q is a bond and $R^{10}$ is

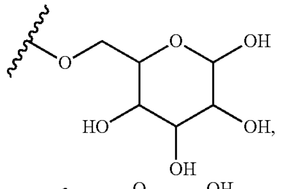

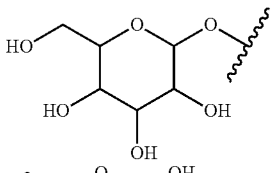

,

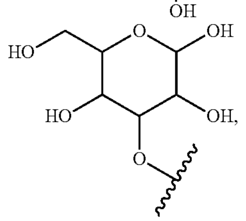

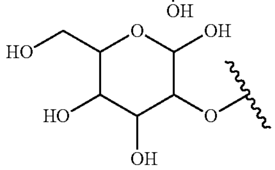

, or

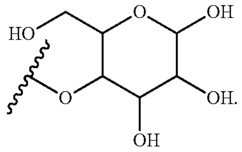

In certain embodiments, Q is O—$(C_1\text{-}C_6)$-alkyl, O—$(C_1\text{-}C_6)$-hydroxyalkyl, O—$(C_1\text{-}C_6)$-aminoalkyl, and $R^{10}$ is

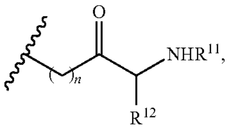

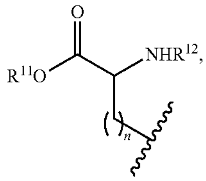

or

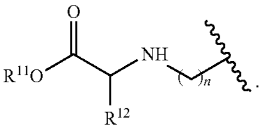

In certain embodiments, Q is O—$(C_1\text{-}C_6)$-aminoalkyl; $R^{10}$ is

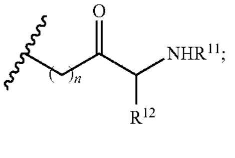

and n is 0.

In certain embodiments, Q is NH—$(C_1\text{-}C_6)$-alkyl, NH—$(C_1\text{-}C_6)$-hydroxyalkyl, NH—$(C_1\text{-}C_6)$-aminoalkyl, and $R^{10}$ is

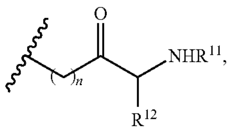

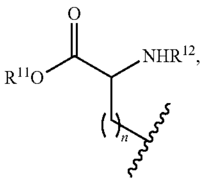

or

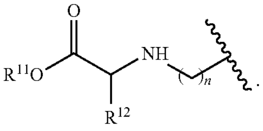

In certain embodiments, Q is NH—($C_1$-$C_6$)-aminoalkyl;

$R^{10}$ is

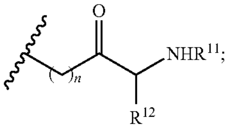

and n is 0.

In certain embodiments, Q is O—($C_1$-$C_6$)-alkyl, or NH—($C_1$-$C_6$)-alkyl, or a bond;

$R^{10}$ is

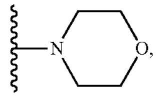 [SMILES: *N1CCOCC1]

aryl, heteroaryl, biaryl, benzyl, or heterocycle.

In certain embodiments, the pharmaceutically acceptable salt of a compound of Formula (I) is an alkyl amine salt.

In certain embodiments, the compound of Formula (I) is selected from the group consisting of:

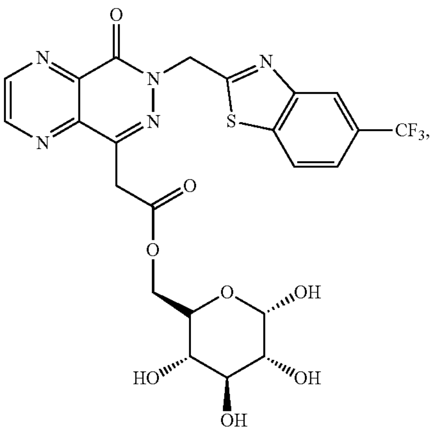

-continued

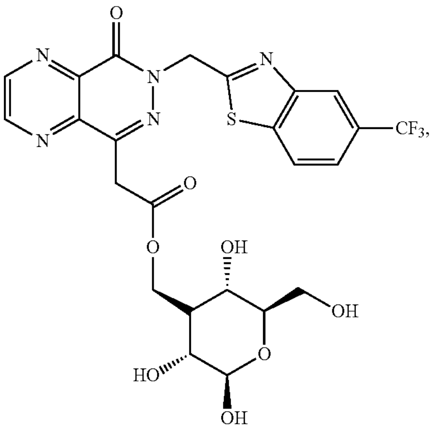

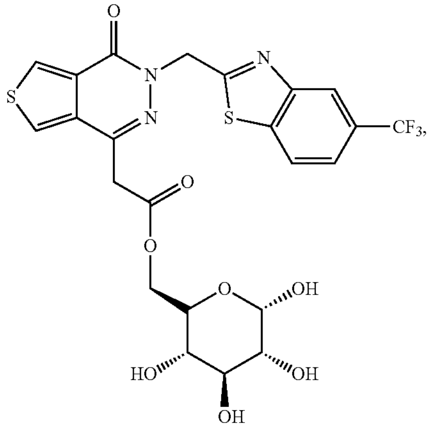

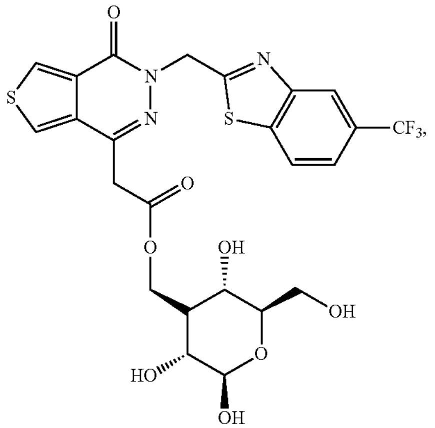

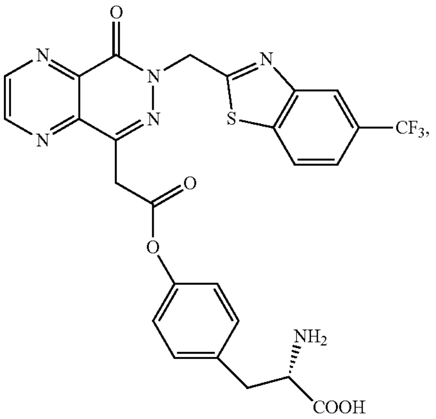

-continued
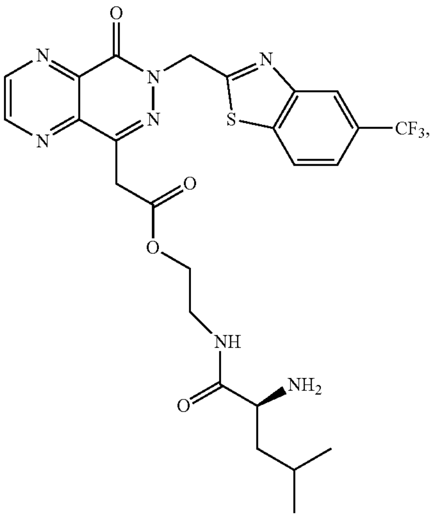
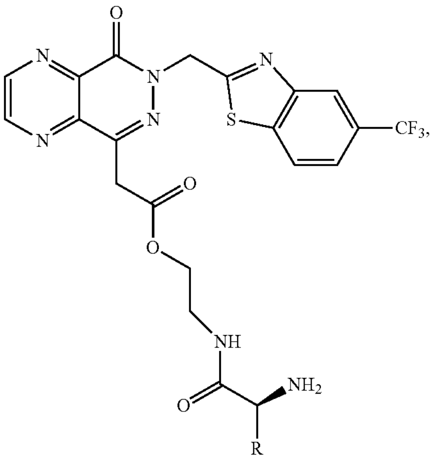
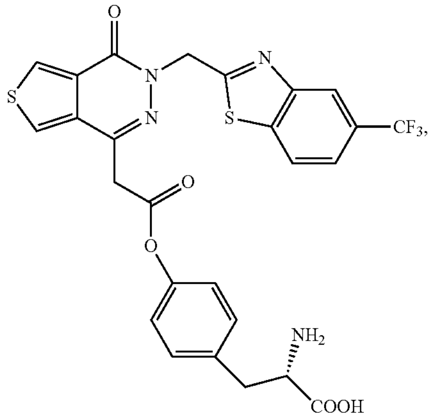
-continued
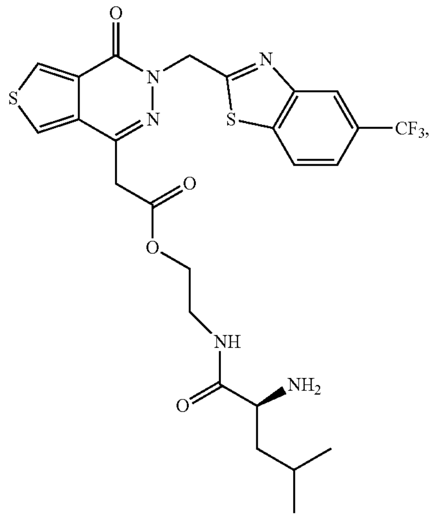
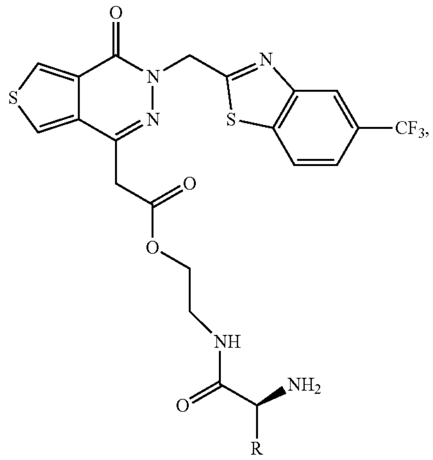
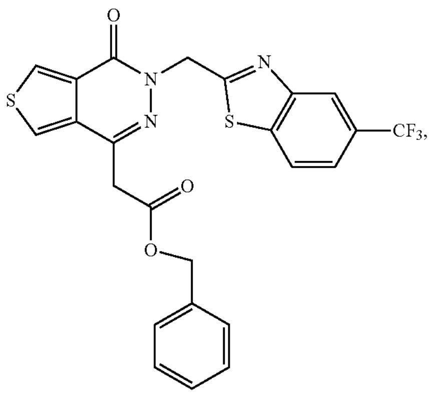
and -continued

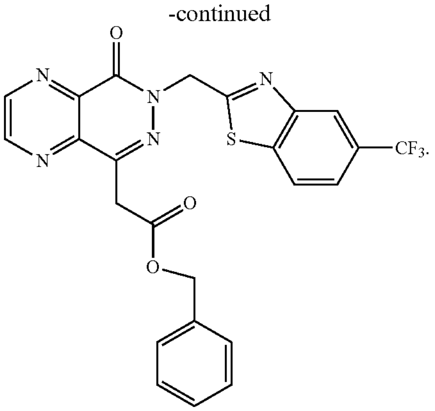

In embodiments, of the compound of Formula (I) $X^1$ is $CR^1$; $X^2$ is S;
$X^3$ is a single bond; $X^4$ is $CR^4$; Y is C=O; Z is

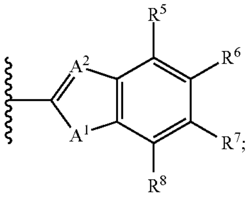

$A^1$ is S; $A^2$ is N and the compound is of Formula (I-4)

(I-4)

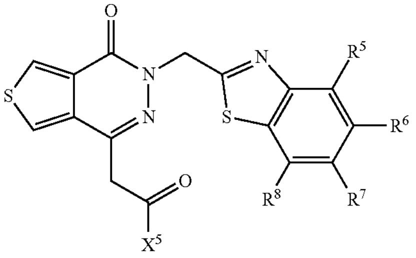

wherein $R^5$, $R^6$, $R^7$, $R^8$ and $X^5$ are as defined in Formula (I). For example, in embodiments, each of $R^5$ through $R^8$ is hydrogen. In certain embodiments, $R^5$, $R^7$, $R^8$ are hydrogen and $R^6$ is halogen or haloalkyl. In embodiments $R^5$, $R^7$, $R^8$ are hydrogen and $R^6$ is haloalkyl. In certain embodiments, $R^5$, $R^7$, $R^8$ are hydrogen and $R^6$ is $CF_3$. In certain embodiments, $R^5$, $R^7$, $R^8$ are hydrogen and $R^6$ is halogen. In certain embodiments, $R^5$, $R^7$, $R^8$ are hydrogen and $R^6$ is F. In certain embodiments, $R^5$, $R^7$, $R^8$ are hydrogen and $R^6$ is Cl. In preferred embodiments of Formula (I-4), $X^5$ is

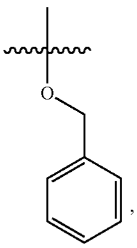, 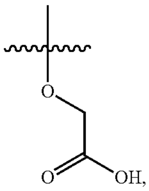 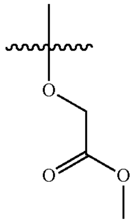,

-continued

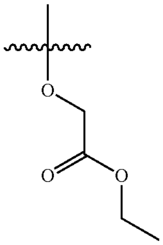, 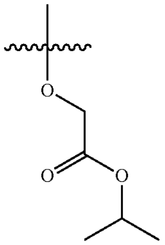, 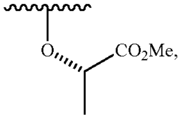

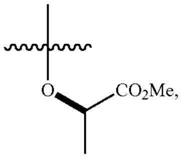 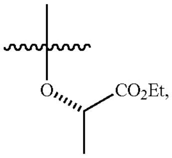 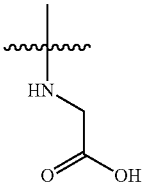,

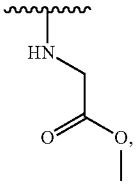 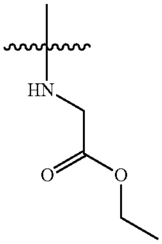, 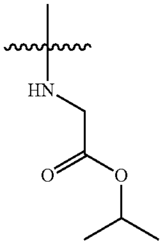,

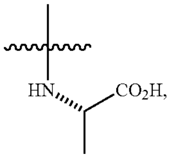 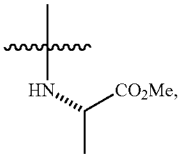 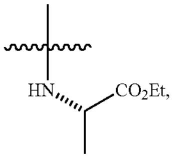

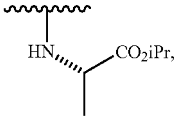 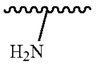, 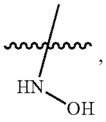,

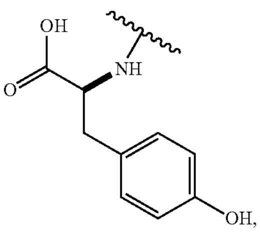 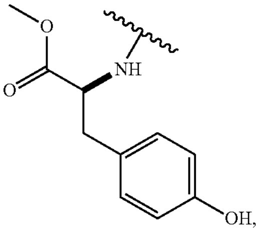

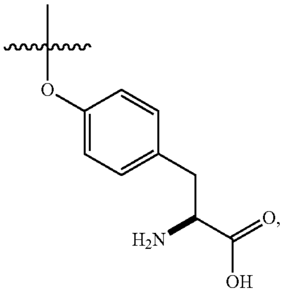

-continued

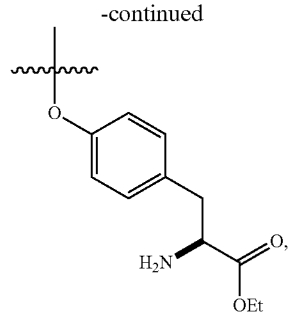

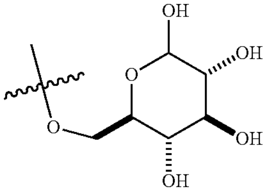

or

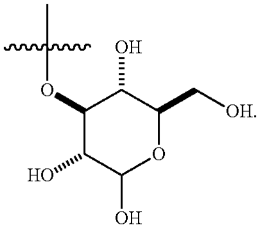

In embodiments, aldose reductase inhibitors described herein encompass compounds of Formula (II) or pharmaceutically acceptable salts, and pro-drugs thereof, (II)

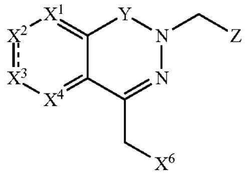

wherein, $X^1$ is N or $CR^1$;

$X^2$ is N, $CR^2$, or S;

$X^3$ is N, $CR^3$, or a bond;

$X^4$ is N or $CR^4$; with the proviso that when $X^2$ is S, $X^1$ is $CR^1$, $X^4$ is $CR^4$, and $X^3$ is a single bond; or that two or three of $X^1$, $X^2$, $X^3$, or $X^4$ are N;

Y is a bond, C═O, C═S, C═NH, or C═N($C_1$-$C_4$)-alkyl; Z is

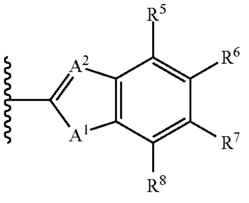

or

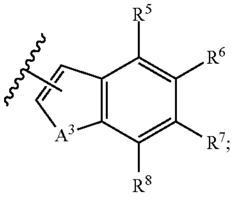

$A^1$ is $NR^9$, O, S or $CH_2$;

$A^2$ is N or CH;

$A^3$ is $NR^9$, O, or S;

$R^1$ through $R^8$ are independently hydrogen, halogen, cyano, acyl, haloalkyl, haloalkoxy, haloalkylthio, trifluoroacetyl, ($C_1$-$C_4$)-alkyl, ($C_1$-$C_4$)-alkoxy, ($C_1$-$C_4$)-alkylthio, ($C_1$-$C_4$)-alkylsulfinyl, or ($C_1$-$C_4$)-alkylsulfonyl; or two of $R^1$ through $R^4$ or two of $R^5$ through $R^8$ taken together are ($C_1$-$C_4$)-alkylenedioxy;

$R^9$ is hydrogen, $C_1$-$C_4$ alkyl, or C(O)O—($C_1$-$C_4$)-alkyl;

$X^6$ is $S(O)_2$—$OR^{13}$, $S(O)_2$—$NHR^{13}$, heteroaryl or heterocycloalkyl; and $R^{13}$ is H or ($C_1$-$C_6$)-alkyl; or a pharmaceutically acceptable salt thereof.

In embodiments, aldose reductase inhibitors described herein encompass the following compounds and pharmaceutically acceptable salts, and pro-drugs thereof.

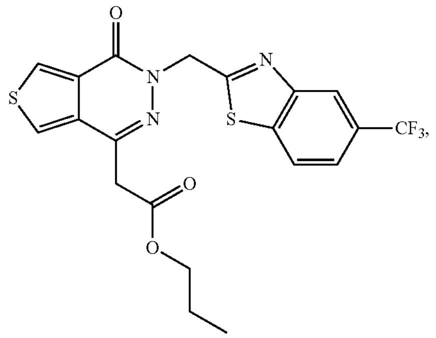

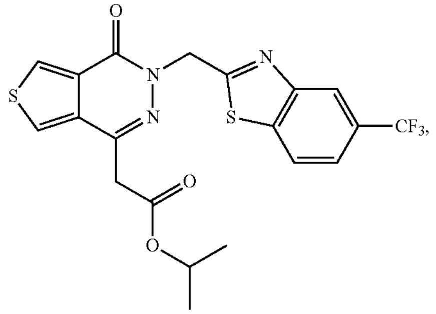

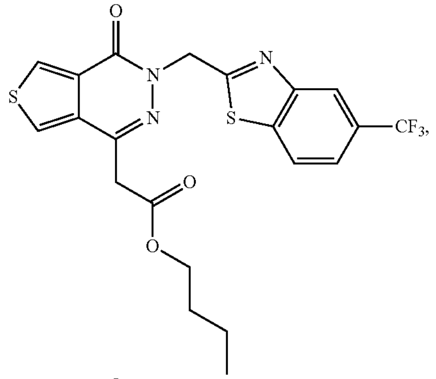

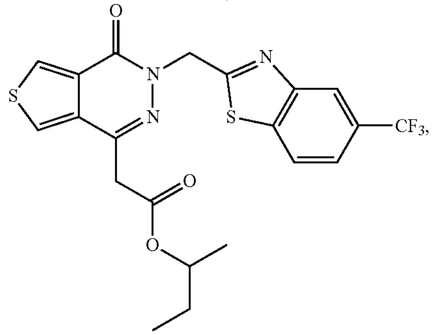

-continued

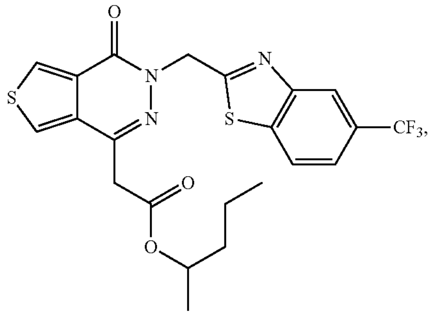

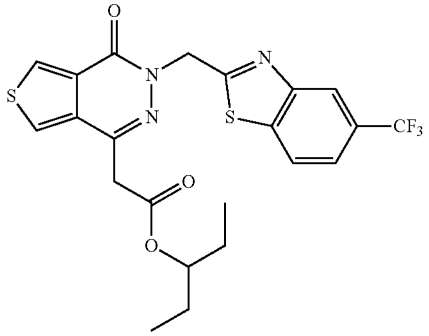

and

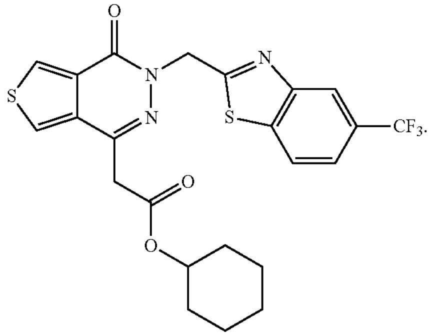

In embodiments, aldose reductase inhibitors described herein encompass the following compounds and pharmaceutically acceptable salts, and pro-drugs thereof.

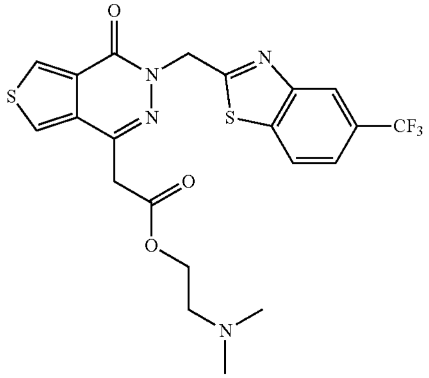

and

-continued

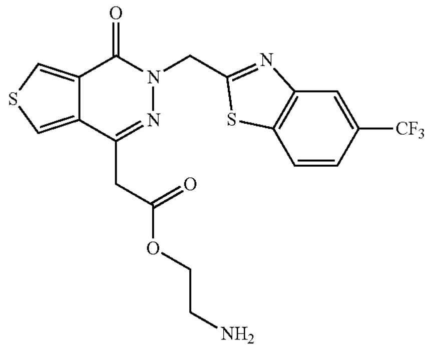

Preferred salts of these compounds include hydrochloride salts.

Synthesis

The compounds described herein can be prepared according to known processes. Schemes 1-10 represent general synthetic schemes for preparing compounds of Formula (I). These schemes are illustrative and are not meant to limit the possible techniques one skilled in the art may use to prepare compounds disclosed herein. Different methods will be evident to those skilled in the art. Various modifications to these methods may be envisioned by those skilled in the art to achieve similar results to that of the inventors provided below. For example, optional protecting groups can be used as described, for example, in Greene et al., *Protective Groups in Organic Synthesis* ($4^{th}$ ed. 2006).

The compounds of Formula (I-1) can generally be prepared, for example, according to Scheme 1:

Scheme 1

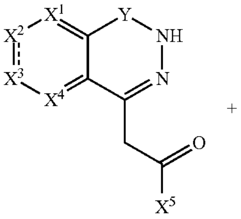

1

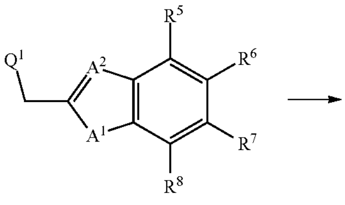

2

-continued

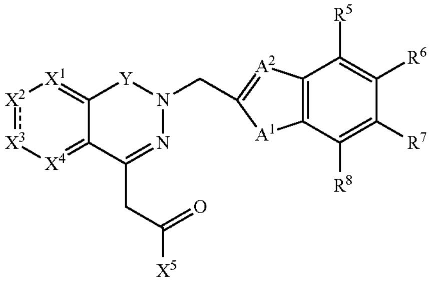

(I-1)

where $X^1$, $X^2$, $X^3$, $X^4$, $A^1$, $A^2$, $R^5$ through $R^9$ are defined as above and $Q^1$ is a halogen, such as Cl, Br, I, and the like, or any other leaving group, such as $OSO_2Me$, OMs, OTs, OTf, and the like.

The compounds of Formula (I-2) can generally be prepared, for example, according to Scheme 2:

Scheme 2

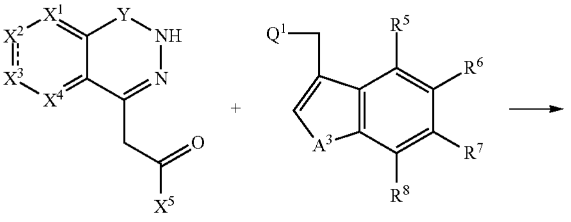

1 3

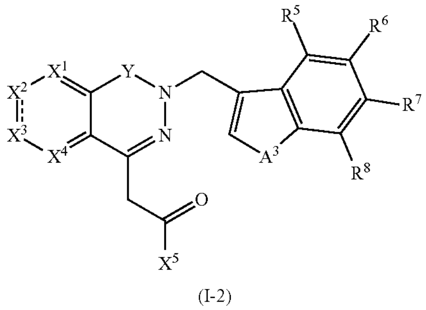

(I-2)

where $X^1$, $X^2$, $X^3$, $X^4$, $A^3$, $R^5$ through $R^9$ are defined as above and $Q^1$ is a halogen, such as Cl, Br, I, and the like, or any other leaving group, such as $OSO_2Me$, OMs, OTs, OTf, and the like.

The compounds of Formula (I-3) can generally be prepared, for example, according to Scheme 3:

Scheme 3

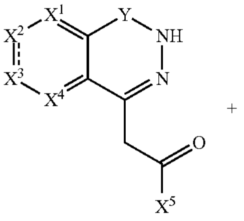

1

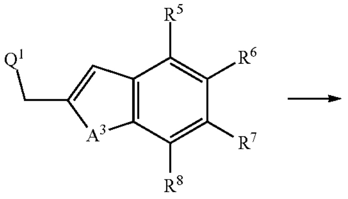

4

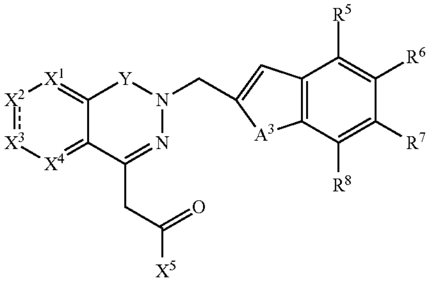

(I-3)

where $X^1$, $X^2$, $X^3$, $X^4$, $A^3$, $R^5$ through $R^9$ are defined as above and $Q^1$ is a halogen, such as Cl, Br, I, and the like, or any other leaving group, such as $OSO_2Me$, OMs, OTs, OTf, and the like.

In certain embodiments, the reaction can be carried out in the presence of a base, such as potassium tert-butoxide, sodium hydride, sodium methoxide, sodium ethoxide, and the like.

In certain embodiments, the reaction can be carried out using aprotic solvents, such as DMF, THF, NMP, and the like. In certain embodiments, the reaction can be carried out using alcohol solvents, such as methanol, ethanol, and the like.

In certain embodiments, the reaction can be carried out at temperatures of between about 5° C. to about 80° C., such as 20° C. to 30° C.

In certain embodiments, the reaction can be subsequently followed by further separation and purification steps, such as chromatography (e.g., flash, HPLC, MPLC, etc.), crystallization, and the like.

Other suitable reactions are possible, such as esterification of

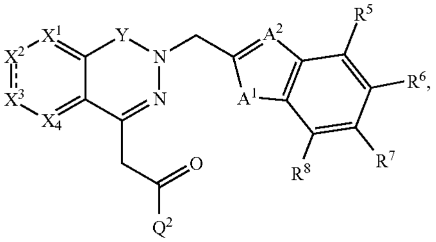

(5)

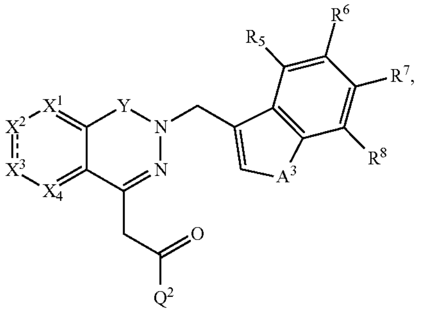

(6)

or

-continued

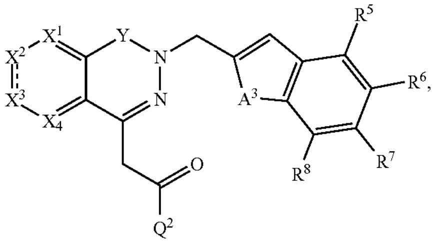

(7)

to obtain different forms of the compound of Formula (I-1), (I-2), or (I-3), respectively. For example, compounds having carboxylic acid group as $Q^2$ (e.g., 5) can be esterified by activating with a suitable reagent, such as thionyl chloride ($SOCl_2$), oxalyl chloride $(COCl)_2$, phosphoryl chloride ($POCl_3$), or the like, followed by reacting with a suitable reagent, such as (3aR,5S,6S,6aR)-5-((R)-2,2-dimethyl-1,3-dioxolan-4-yl)-2,2-dimethyltetrahydrofuro[2,3-d][1,3]dioxol-6-ol (9) to obtain a compound of Formula (I-1) having 3-glucosyl as $X^5$ (i.e., 10).

For example, the following exemplary synthesis can be carried out according to Scheme 4.

Scheme 4

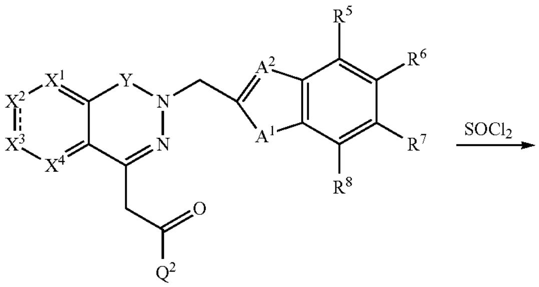

5

$Q^2$ = OH

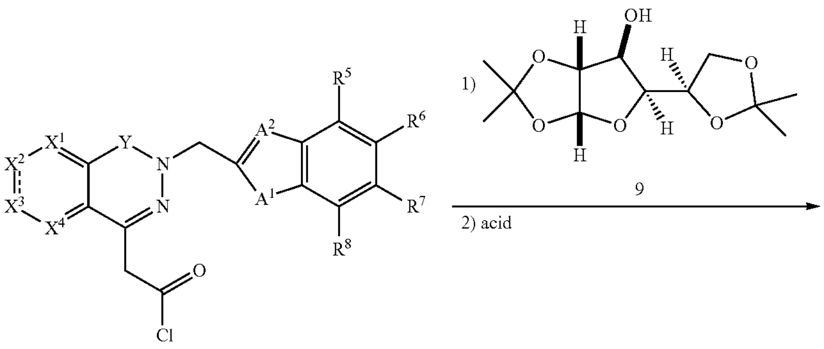

8

-continued

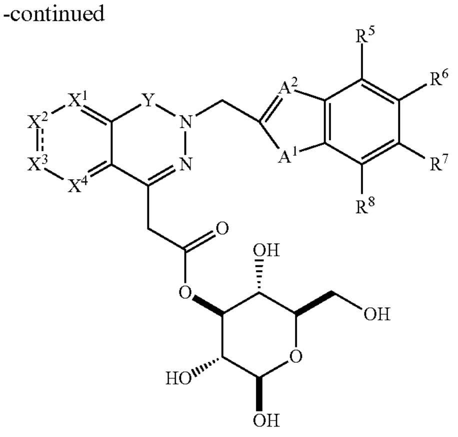

10

In certain embodiments, the reaction with compound 9 according to Scheme 4 can be carried out in the presence of a base, such as triethylamine, diisopropylethylamine, imidazole, pyridine, and the like.

In certain embodiments, the reaction with compound 9 according to Scheme 4 can be carried out in the presence of an additive, such as DMAP, and the like. In certain embodiments, the reaction with compound 9 can be carried out in the absence of an additive.

In certain embodiments, the reaction with compound 9 according to Scheme 4 can be carried out using aprotic solvents, such as DMF, THF, and the like.

In certain embodiments, the acid in the reaction according to Scheme 4 can be trifluoroacetic acid (TFA), and the like.

Other suitable esterification reactions of the compound of Formula (5), (6), or (7) are possible to obtain different forms of the compound of Formula (I-1), (I-2), or (I-3), respectively. For example, compounds having carboxylic acid group as $Q^2$ (e.g., 5) can be reacted with compound 9, in the presence of an additive such as N,N'-Dicyclohexylcarbodiimide (DCC), (Benzotriazol-1-yloxy)tris(dimethylamino) phosphonium hexafluorophosphate (BOP), carbonyldiimidazole (CDI), 1-Ethyl-3-(3-dimethylaminopropyl) carbodiimide (EDAC), or the like, to obtain a compound of Formula (I-1) having 3-glucosyl as $X^5$ (i.e., 10).

For example, the following exemplary synthesis can be carried out according to Scheme 5.

Scheme 5

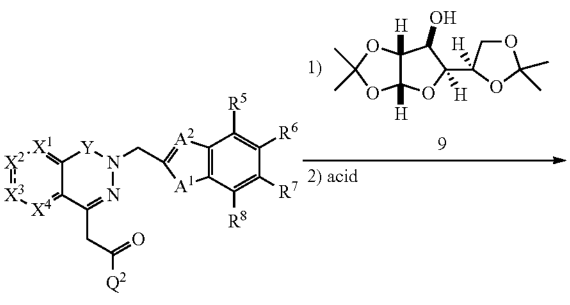

5

$Q^2$ = OH

-continued

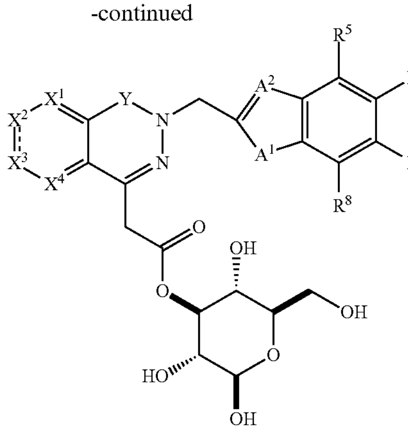

10

In certain embodiments, the reaction with compound 9 according to Scheme 5 can be carried out in the presence of a base, such as triethylamine, diisopropylethylamine, imidazole, pyridine, and the like.

In certain embodiments, the reaction with compound 9 according to Scheme 5 can be carried out with DMAP and DCC, BOP, CDI, EDAC, or the like. In certain embodiments, the reaction with compound 9 according to Scheme 5 can be carried out in the absence of DCC, BOP, CDI, EDAC, or the like.

In certain embodiments, the reaction with compound 9 according to Scheme 5 can be carried out using aprotic solvents, such as DMF, THF, and the like.

In certain embodiments, the acid in the reaction according to Scheme 5 can be trifluoroacetic acid (TFA), and the like.

Other suitable reactions are possible, such as esterification of the compound of Formula (5), (6), or (7) to obtain different forms of the compound of Formula (I-1), (I-2), or (I-3), respectively. For example, compounds having carboxylic acid group as $Q^2$ (e.g., 5) can be esterified by reacting with a suitable reagent, such as glucose (11) to obtain a compound of Formula (I-1) having 6-glucosyl as $X^5$ (i.e., (12)).

For example, the following exemplary synthesis can be carried out according to Scheme 6.

Scheme 6

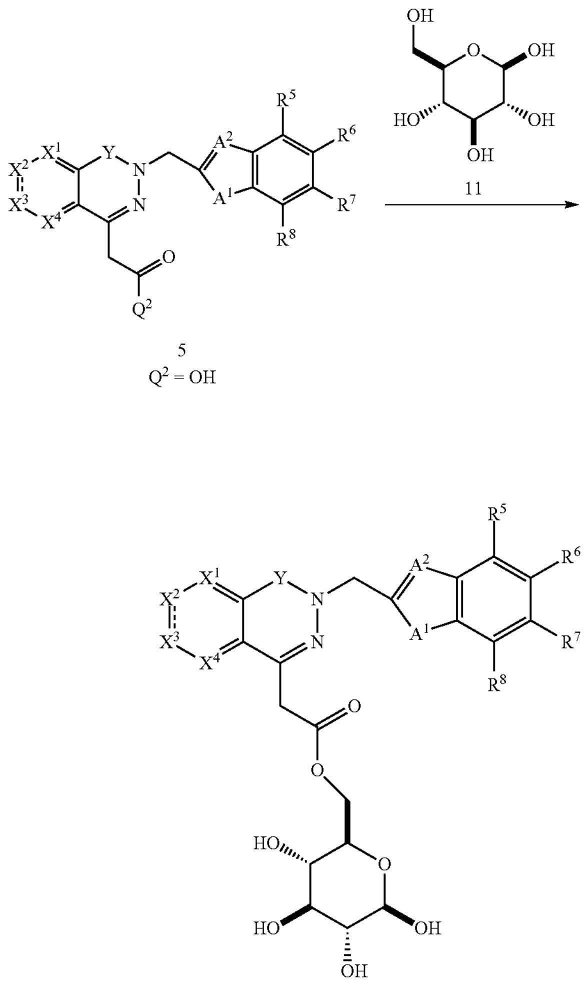

5

$Q^2 = OH$

11

12

Scheme 7

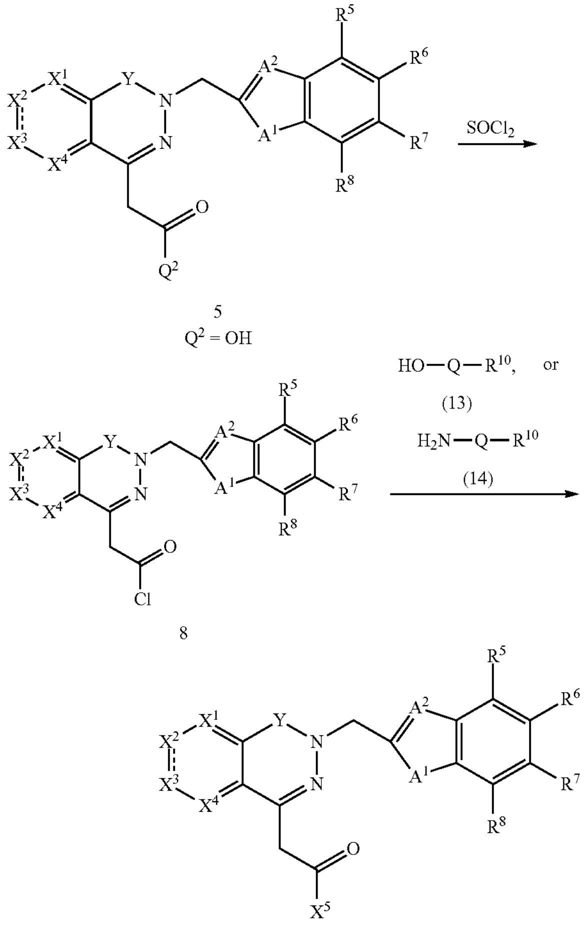

5

$Q^2 = OH$

8

15, $X^5$ = O—Q—$R^{10}$

16, $X^5$ = HN—Q—$R^{10}$

In certain embodiments, the reaction according to Scheme 6 can be carried out in the presence of an enzyme, such as lipase, triacylglycerol lipase, and the like.

In certain embodiments, the reaction according to Scheme 6 can be carried out in solvents such as tert-butanol, acetone, and the like.

In certain embodiments, the reaction can be carried out at temperatures of between about 20° C. to about 80° C., such as 20° C. to 30° C., 30° C. to 40° C., 40° C. to 50° C., 50° C. to 60° C., 60° C. to 70° C., 70° C. to 80° C., and the like.

Other suitable reactions of the compound of Formula (5), (6), or (7) are possible to obtain different forms of the compound of Formula (I-1), (I-2), or (I-3), respectively. For example, compounds having carboxylic acid group as $Q^2$ (e.g., 5) can be reacted with a suitable reagent, such as thionyl chloride ($SOCl_2$), oxalyl chloride $(COCl)_2$, phosphoryl chloride ($POCl_3$), or the like, followed by reaction with a suitable reagent, such as HO-Q-$R^{10}$ (13), $H_2N$-Q-$R^{10}$ (14), or the like, to obtain a compound of Formula (I-1), such as compound 15 or compound 16.

For example, the following exemplary synthesis can be carried out according to Scheme 7.

In certain embodiments, the reaction according to Scheme 7 can be carried out by replacing thionyl chloride ($SOCl_2$) with oxalyl chloride $(COCl)_2$, phosphoryl chloride ($POCl_3$), and the like.

In certain embodiments, the reaction with compound 13 or 14 according to Scheme 7 can be carried out in the presence of a base, such as triethylamine, diisopropylethylamine, imidazole, pyridine, and the like.

In certain embodiments, the reaction with compound 13 or 14 according to Scheme 7 can be carried out in the presence of an additive, such as DMAP, and the like. In certain embodiments, the reaction with compound 9 can be carried out in the absence of an additive.

In certain embodiments, the reaction with compound 13 or 14 according to Scheme 7 can be carried out using aprotic solvents, such as DMF, THF, and the like.

In certain embodiments, compounds such as 13 or 14 comprise protecting groups, which can be removed as described, for example, in Greene et al., *Protective Groups in Organic Synthesis* ($4^{th}$ ed. 2006). For example, compounds having carboxylic acid group as $Q^2$ (e.g., (5)) can be reacted with a suitable reagent, such as thionyl chloride ($SOCl_2$), oxalyl chloride $(COCl)_2$, phosphoryl chloride ($POCl_3$), or the like, followed by reaction with a suitable reagent, such as benzyl (1-((2-aminoethyl) amino)-1-oxopropan-2-yl) carbamate (18), or the like, to obtain compound 19. Deprotection of compound 19 provides a compound of formula 20.

For example, the following exemplary synthesis can be carried out according to Scheme 8.

Scheme 8

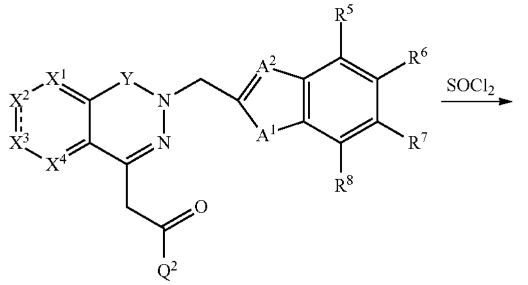

5

$Q^2$ = OH

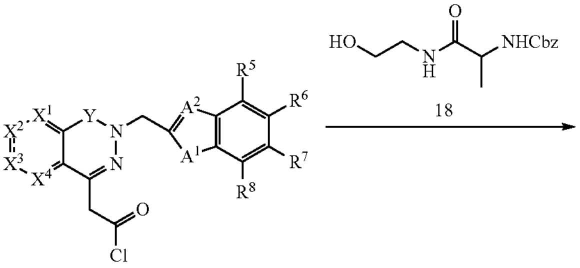

18

8

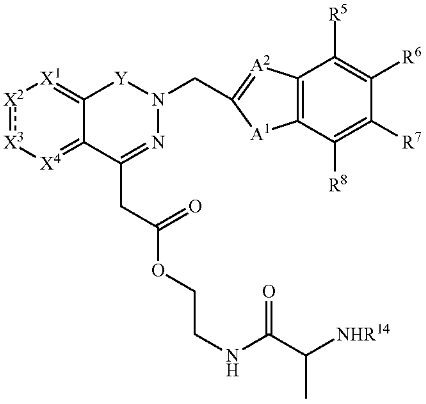

19, $R^{14}$ = Cbz

20, $R^{14}$ = H

Other suitable reactions of the compound of Formula (5), (6), or (7) are possible to obtain different forms of the compound of Formula (I-1), (I-2), or (I-3), respectively. For example, compounds having carboxylic acid group as $Q^2$ (e.g., 5) can be reacted with a suitable reagent, such as HO-Q-$R^{10}$ (13), $H_2N$-Q-$R^{10}$ (14), or the like, in the presence of an additive such as N,N-Dicyclohexylcarbodiimide (DCC), (Benzotriazol-1-yloxy)tris(dimethylamino)phosphonium hexafluorophosphate (BOP), carbonyldiimidazole (CDI), 1-Ethyl-3-(3-dimethylaminopropyl)carbodiimide (EDAC), or the like, to obtain a compound of Formula (I-1), such as compound 15 or 16.

For example, the following exemplary synthesis can be carried out according to Scheme 9.

Scheme 9

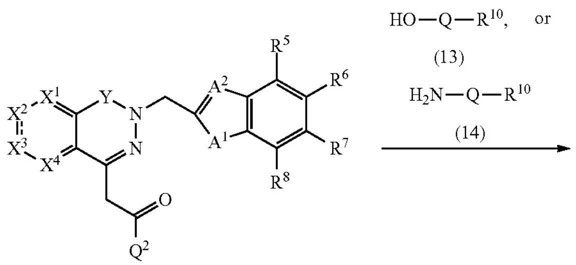

5

$Q^2$ = OH

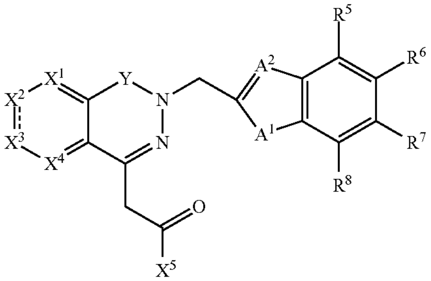

15, $X^5$ = O—Q—$R^{10}$

16, $X^5$ = HN—Q—$R^{10}$

In certain embodiments, the reaction according to Scheme 9 can be carried out in the presence of a base, such as triethylamine, diisopropylethylamine, imidazole, pyridine, and the like.

In certain embodiments, the reaction according to Scheme 9 can be carried out with DMAP and DCC, BOP, CDI, EDAC, or the like. In certain embodiments, the reaction according to Scheme 9 can be carried out in the absence of DCC, BOP, CDI, EDAC, or the like.

In certain embodiments, the reaction according to Scheme 9 can be carried out using aprotic solvents, such as DMF, THF, and the like.

Other suitable reactions of the compound of Formula (5), (6), or (7) are possible to obtain different forms of the compound of Formula (I-1), (I-2), or (I-3), respectively. For example, compounds having carboxylic acid group as $Q^2$ (e.g., 5) can be reacted with a suitable reagent, such as $X^6$-Q-$R^{10}$ (17), where $X^6$ is a halogen, in the presence of an additive such as tetra-n-butylammonium bromide (TBAB), tetra-n-butylammonium iodide (TBAI), tetra-n-butylammonium chloride (TBAC), or the like, to obtain a compound of Formula (I-1), such as compound 15.

For example, the following exemplary synthesis can be carried out according to Scheme 10.

Scheme 10

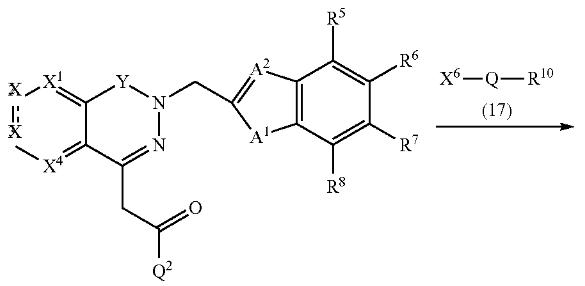

5
$Q^2$ = OH

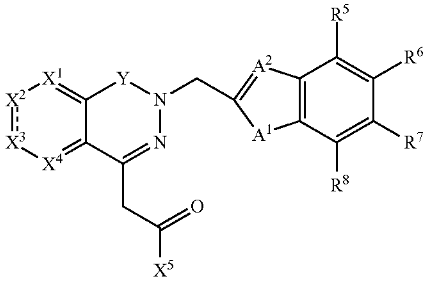

15, $X^5$ = O—Q—$R^{10}$

In certain embodiments, $X^6$-Q-$R^{10}$ (17) is Cl-Q-$R^{10}$. In certain embodiments, $X^6$-Q-$R^{10}$(17) is Br-Q-$R^{10}$. In certain embodiments, $X^6$-Q-$R^{10}$ (17) is I-Q-$R^{10}$.

In certain embodiments, the reaction according to Scheme 10 can be carried out in the presence of a base, such as triethylamine, diisopropylethylamine, imidazole, pyridine, and the like.

In certain embodiments, the reaction according to Scheme 10 can be carried out in the absence of TBAI, TBAB, or TBAC.

In certain embodiments, the reaction according to Scheme 10 can be carried out using aprotic solvents, such as DMF, THF, and the like.

The compounds of Formula (I-2) can also generally be prepared according to Schemes 4-9, by replacing (5)

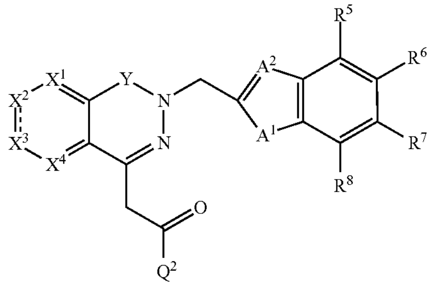

with

-continued (6)

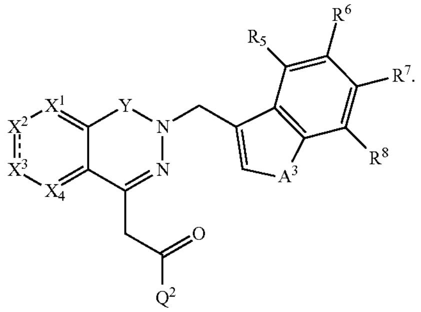

Similarly, the compounds of Formula (I-3) can also generally be prepared according to Scheme 4-9, by replacing (5)

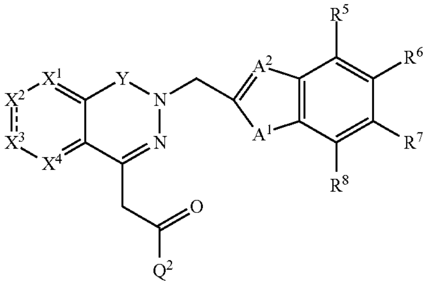

with (7)

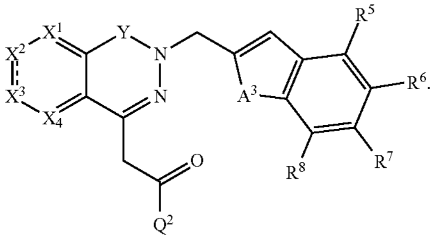

Exemplary descriptions regarding synthesis of certain compounds of Formula (I-1), Formula (I-2), and Formula (I-3) are described in U.S. Pat. No. 8,916,563 and WO2017/038505; each of which is hereby incorporated by reference in its entirety.

Compounds of Formula (5), (6), and (7)

Exemplary descriptions regarding synthesis of certain compounds of Formula (5), (6), and (7) are described in U.S. Pat. No. 8,916,563 and WO2017/38505; each of which is hereby incorporated by reference in its entirety.

Compounds of Formula (1)

Exemplary descriptions regarding synthesis of certain compounds of Formula (1) are described in U.S. Pat. No. 8,916,563 and WO2017/38505; each of which is hereby incorporated by reference in its entirety.

Compounds of Formula (2), (3), and (4)

Exemplary descriptions regarding synthesis of certain compounds of Formula (2), (3), and (4) are described in U.S. Pat. No. 8,916,563 and WO2017/038505; each of which is hereby incorporated by reference in its entirety.

Additional exemplary syntheses of certain compounds of Formula (2), (3), and (4) are described in *J. Med. Chem.* (1991), Vol. 34, pp. 108-122; *J Med. Chem.* (1992), Vol. 35, No. 3, pp. 457-465; and U.S. Pat. No. 8,916,563; each of which hereby incorporated by reference in its entirety.

Exemplary pro-drug esters can be prepared as described by Placzek et al., in *Bioorganic & Medicinal Chemistry* 2016, 24, 5842-5854, which is hereby incorporated by reference in its entirety.

Compounds or compositions of the invention can be useful in applications that benefit from inhibition of aldose reductase enzymes. Exemplary utility of aldose reductase inhibition may be found, for example, in U.S. Pat. Nos. 8,916,563; 9,650,383; 5,677,342; 5,155,259; 4,939,140; U.S. Publication Number US 2006/0293265; WO 2017/223179; Danish Patent Application DK2326632; U.S Publication Number 2017/0224651; Korean Patent Application KR[10] 20090084439; US Publication Number 2017/0319584; Korean Patent KR1020120055370; Lo et al., in *Journal of Cerebral Blood Flow & Metabolism* 2007, 27, 1496-1509; Ip et al., in *BMC Complement Altern Med* 2016, 16,437; Shen et al., in *Brain Res* 2010, 118-129; Ramirez et al., in *Pharmacotherapy* 2008, 28(5), 646-55; Tang et al., in *PLoS One* 2013, 8 (4); P. Pacher, NIH Grant 1Z01AA000375-03; and Roy et al., in *Diabetes Research and Clinical Practice* 1990, 10(1), 91-97; and references cited therein; each of which hereby incorporated by reference in its entirety. Inhibition of aldose reductase also has been found to prevent metastasis of colon cancer and mitosis in colon cancer cells (See, for example, Tammali, R. et al., Inhibition of Aldose Reductase Prevents Colon Cancer Metastasis, *Carcinogenesis* 2011, doi: 10.1093/carcin/bgrl02; published online: Jun. 3, 2011*; Angiogenesis* 2011 May; 14(2):209-21; and *Mol. Cancer Ther.* 2010, April; 9(4): 813-824; each of which hereby incorporated by reference in its entirety).

In certain embodiments, compounds and/or compositions of the invention can be useful in promoting healthy aging of skin, the treatment of skin disorders, the treatment of angiogenesis disorders such as cancers, including colon cancer, the treatment of non-cardiac tissue damage, the treatment of cardiovascular disorders, the treatment of renal disorders, the treatment of evolving myocardial infarction, the treatment of ischemic injury, and the treatment various other disorders, such as complications arising from diabetes. Such disorders can include, but are not limited to, atherosclerosis, coronary artery disease, diabetic nephropathy, diabetic neuropathy, diabetic retinopathy, infections of the skin, peripheral vascular disease, stroke, asthma and the like.

In certain embodiments, compounds and/or compositions of the invention can be useful in the treatment of stroke, ischemic stroke, tissue damage, brain damage, neural damage, an autoimmune disease, and galactosemia in a subject. In certain embodiments, compounds and/or compositions of the invention can be useful in the treatment of stroke in a subject. In certain embodiments, compounds and/or compositions of the invention can be useful in the treatment of ischemic stroke in a subject. In certain embodiments, compounds and/or compositions of the invention can be useful in the treatment of tissue damage in a subject. In certain embodiments, compounds and/or compositions of the invention can be useful in the treatment of brain damage in a subject. In certain embodiments, compounds and/or compositions of the invention can be useful in the treatment of neural damage in a subject. In certain embodiments, compounds and/or compositions of the invention can be useful in the treatment of an autoimmune disease in a subject. In certain embodiments, compounds and/or compositions of the invention can be useful in the treatment of galactosemia in a subject. The compounds and/or compositions described herein can be administered to a subject in need thereof for the treatment of PMM2-CDG.

The compounds and/or compositions described herein can be administered to a subject in need thereof for the treatment of cutaneous aging. Accordingly, the methods disclosed herein can reduce or delay the signs of cutaneous aging, such as the appearance of as lines, creases, wrinkles and crepey skin and loss of elasticity or firmness of the skin. In the practice of the disclosed methods, the aldose reductase inhibitor can be topically administered to the skin, for example by application to the surface of the skin (e.g., of a topical formulation that contains the aldose reductase inhibitor). The aldose reductase inhibitor can be applied to the surface of any desired area of the skin. For example, the aldose reductase inhibitor can be applied to the surface of skin that is typically exposed in social settings, such as the skin of the face, neck, chest, arms, hands or any combination of the foregoing, to reduce or delay cutaneous aging in those areas of the skin.

In certain embodiments, compounds and/or compositions of the invention can be useful in cardiovascular applications. For example, compounds and/or compositions of the invention can be used to treat patients undergoing a heart bypass surgery to improve recovery after the surgery. In another example, compounds and/or compositions of the invention can be used to inhibit or reduce accumulation or rapid onset of atherosclerotic plaque. In another example, compounds and/or compositions of the invention can be used to treat cardiomyopathy. In another example, compounds and/or compositions of the invention can be used to treat diabetic cardiomyopathy.

In some other embodiments, compounds and/or compositions of the invention can be useful in topical applications. For example, compounds and/or compositions of the invention can be used to retard or reduce skin aging.

In certain embodiments, compounds disclosed herein can be administered to a subject in need of treatment at dosages ranging from about 0.5 to about 25 mg/kg body weight of the subject to be treated per day, such as from about 1.0 to 10 mg/kg. However, additional variations are within the scope of the invention.

The compounds disclosed herein can be administered alone or in combination with pharmaceutically acceptable carriers, such as diluents, fillers, aqueous solution, and even organic solvents. The compound and/or compositions of the invention can be administered as a tablet, powder, lozenge, syrup, injectable solution, and the like. Additional ingredients, such as flavoring, binder, excipients, and the like are within the scope of the invention.

In certain embodiments, pharmaceutically acceptable compositions can contain a compound disclosed herein (e.g., a compound of Formula (I)) and/or a pharmaceutically acceptable salt thereof at a concentration ranging from about 0.01 to about 2 wt %, such as 0.01 to about 1 wt % or about 0.05 to about 0.5 wt %. The composition can be formulated as a solution, suspension, ointment, or a capsule, and the like. The pharmaceutical composition can be prepared as an aqueous solution and can contain additional components, such as preservatives, buffers, tonicity agents, antioxidants, stabilizers, viscosity-modifying ingredients and the like.

Other modes of administration can be found in U.S. Pat. No. 4,939,140, hereby incorporated by reference herein in its entirety.

In certain embodiments, the present invention provides for the use of pharmaceutical compositions and/or medicaments comprised of a compound of Formula (I), or a pharmaceutically acceptable salt, hydrate, solvate, or prodrug thereof, in a method of treating a disease state, and/or condition caused by or related to aldose reductase.

In certain embodiments, the method of treatment comprises the steps of (i) identifying a subject in need of such treatment; (ii) providing a compound disclosed herein, or a pharmaceutically acceptable salt, hydrate, solvate, or pro-drug thereof; and (iii) administering said compound in a therapeutically effective amount to treat, suppress and/or prevent the disease state or condition in a subject in need of such treatment.

In certain embodiments the method of treatment comprises the steps of (i) identifying a subject in need of such treatment; (ii) providing a composition comprising a compound as disclosed herein, or a pharmaceutically acceptable salt, hydrate, solvate, or pro-drug thereof; and (iii) administering said composition in a therapeutically effective amount to treat, suppress and/or prevent the disease state or condition in a subject in need of such treatment.

In certain embodiments, the subject in need is an animal. In another embodiment, the patient in need is an animal. Animals include all members of the animal kingdom, but are not limited to humans, mice, rats, cats, monkeys, dogs, horses, and swine. In some embodiments, the subject in need is a human. In some embodiments, the subject in need is a mouse, a rat, a cat, monkey, a dog, a horse, or a pig. In some embodiments, the patient in need is a human. In some embodiments, the patient in need is a mouse, a rat, a cat, a monkey, a dog, a horse, or a pig.

In certain embodiments, the compound or composition is administered orally. In certain embodiments, the compound or composition is administered intravenously.

In certain embodiments, the methods comprise administering to the subject an effective amount of a compound disclosed herein, or a pharmaceutically acceptable salt, solvate, hydrate or pro-drug thereof; or a composition comprising a compound as disclosed herein, or a pharmaceutically acceptable salt, solvate, hydrate or pro-drug thereof, and a pharmaceutically acceptable carrier.

Pharmaceutically acceptable carriers are well-known to those skilled in the art, and include, for example, adjuvants, diluents, excipients, fillers, lubricants and vehicles. In some embodiments, the carrier is a diluent, adjuvant, excipient, or vehicle. In some embodiments, the carrier is a diluent, adjuvant, or excipient. In some embodiments, the carrier is a diluent or adjuvant. In some embodiments, the carrier is an excipient. Often, the pharmaceutically acceptable carrier is chemically inert toward the active compounds and is non-toxic under the conditions of use. Examples of pharmaceutically acceptable carriers may include, for example, water or saline solution, polymers such as polyethylene glycol, carbohydrates and derivatives thereof, oils, fatty acids, or alcohols. Non-limiting examples of oils as pharmaceutical carriers include oils of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in e.g., Remington's: The Science and Practice of Pharmacy, $22^{nd}$ Ed. (Allen, Loyd V., Jr ed., Pharmaceutical Press (2012)); Modem Pharmaceutics, $5^{th}$ Ed. (Alexander T. Florence, Juergen Siepmann, CRC Press (2009)); Handbook of Pharmaceutical Excipients, $7^{th}$ Ed. (Rowe, Raymond C.; Sheskey, Paul J.; Cook, Walter G.; Fenton, Marian E. eds., Pharmaceutical Press (2012)) (each of which hereby incorporated by reference in its entirety).

In one embodiment, a pharmaceutical composition is a mixture of one or more of the compounds described herein, or pharmaceutically acceptable salts, solvates, pro-drugs or hydrates thereof, with other chemical components, such as physiologically acceptable carriers and excipients. The purpose of a pharmaceutical composition is to facilitate administration of a compound to an organism or subject.

In certain embodiments, the method of treatment, prevention and/or suppression of a disease state or disorder or condition related to aldose reductase comprises the steps of: (i) identifying a subject in need of such treatment; (ii) providing a compound disclosed herein, or a pharmaceutically acceptable salt, solvate, hydrate or pro-drug thereof; or a composition comprising a compound as disclosed herein, or a pharmaceutically acceptable salt, solvate, hydrate or pro-drug thereof, and a pharmaceutically acceptable carrier; and (iii) administering said compound or composition in a therapeutically effective amount to treat, prevent and/or suppress the disease state or disorder or condition related to aldose reductase in a subject in need of such treatment.

A "pro-drug" or "pro-drug" refers to an agent which is converted into the active drug in vivo. Pro-drugs are often useful because, in some situations, they are easier to administer than the parent drug. They are bioavailable, for instance, by oral administration whereas the parent drug is either less bioavailable or not bioavailable. In some embodiments, the pro-drug has improved solubility in pharmaceutical compositions over the parent drug. For example, the compound carries protective groups that are removed in vivo, thus releasing active compound. The term "pro-drug" may apply to such functionalities as, for example, the acid functionalities of the compounds of Formula (I). Pro-drugs may be comprised of structures wherein an acid group is masked, for example, as an ester or amide. Further examples of pro-drugs are discussed herein and, for example, by Alexander et al., *J Med. Chem.* 1988, 31, 318 (hereby incorporated by reference in its entirety).

In certain embodiments, the present invention also encompasses methods comprising administration of pro-drugs of compounds of Formula (I) and/or pharmaceutical compositions thereof. Pro-drugs include derivatives of compounds that can hydrolyze, oxidize, or otherwise react under biological conditions (in vitro or in vivo) to provide an active compound of the invention. Examples of pro-drugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, and biohydrolyzable phosphate analogues. Pro-drugs may be comprised of structures wherein a acid group is masked, for example, as an ester or amide. Further examples of pro-drugs are discussed, for example, by Alexander et al., *J Med. Chem.* 1988, 31, 318; and in *The Practice of Medicinal Chemistry* (Camille Wermuth, ed., 1999, Academic Press; hereby incorporated by reference in its entirety). Pro-drugs are often useful because, in some situations, they are easier to administer than the parent drug. They are bioavailable, for instance, by oral administration whereas the parent drug is either less bioavailable or not bioavailable. In some embodiments, the pro-drug has improved solubility in pharmaceutical compositions over the parent drug. For example, the compound carries protective groups that are removed in vivo, thus releasing active compound. Pro-drugs, in some cases, offer enhanced permeability across the blood brain barrier relative to the parent compound. In some embodiments, the pro-drug utilizes transport mechanisms to cross the blood brain barrier.

In certain embodiments, pro-drugs of compounds with carboxyl functional groups are the ($C_1$-$C_4$) alkyl esters of the carboxylic acid. The carboxylate esters are conveniently formed by esterifying any of the carboxylic acid moieties present on the molecule. Pro-drugs can typically be prepared using well-known methods, such as those described by *Burger's Medicinal Chemistry and Drug Discovery* 6$^{th}$ ed. (Donald J. Abraham ed., 2001, Wiley) and *Design and Application of Pro-drugs* (H. Bundgaard ed., 1985, Harwood Academic Publishers Gmfh; each of which hereby incorporated by reference in its entirety). Biohydrolyzable moieties of a compound of Formula (I) (i) do not interfere with the biological activity of the compound but can confer upon that compound advantageous properties in vivo, such as uptake, duration of action, or onset of action; or (ii) may be biologically inactive but are converted in vivo to the biologically active compound. Examples of biohydrolyzable esters include, but are not limited to, ($C_1$-$C_4$) alkyl esters, alkoxyacyloxy esters, alkyl acylamino alkyl esters, and choline esters. Examples of biohydrolyzable amides include, but are not limited to, ($C_1$-$C_4$) alkyl amides, α-amino acid amides, alkoxyacyl amides, and alkylaminoalkylcarbonyl amides. Examples of biohydrolyzable carbamates include, but are not limited to, ($C_1$-$C_4$) alkylamines, substituted ethylenediamines, aminoacids, hydroxyalkylamines, heterocyclic and heteroaromatic amines, and polyether amines.

In some embodiments, the biohydrolyzable moiety is an ester comprising a ($C_1$-$C_6$)-alkyl linker, a ($C_1$-$C_6$)-hydroxyalkyl linker, a ($C_1$-$C_6$)-aminoalkyl linker, an aryl linker, a heteroaryl linker, a biaryl linker, or a benzyl linker. In some embodiments, the biohydrolyzable moiety is an ester comprising a ($C_1$-$C_6$)-alkyl linker, a ($C_1$-$C_6$)-hydroxyalkyl linker, or a ($C_1$-$C_6$)-aminoalkyl linker. In some embodiments, the biohydrolyzable moiety is an ester comprising a ($C_1$-$C_6$)-alkyl linker or a ($C_1$-$C_6$)-hydroxyalkyl linker. In some embodiments, the biohydrolyzable moiety is an ester comprising a ($C_1$-$C_6$)-alkyl linker or a ($C_1$-$C_6$)-aminoalkyl linker. In some embodiments, the biohydrolyzable moiety is an ester comprising a ($C_1$-$C_6$)-hydroxyalkyl linker or a ($C_1$-$C_6$)-aminoalkyl linker. In some embodiments, the biohydrolyzable moiety is an ester comprising an aryl linker, a heteroaryl linker, a biaryl linker, or a benzyl linker. In some embodiments, the biohydrolyzable moiety is an ester comprising an aryl linker, a heteroaryl linker, or a benzyl linker. In some embodiments, the biohydrolyzable moiety is an ester comprising an aryl linker or a benzyl linker. In some embodiments, the biohydrolyzable moiety is an ester comprising an aryl linker or a heteroaryl linker.

In some embodiments, the biohydrolyzable moiety is an amide comprising a ($C_1$-$C_6$)-alkyl linker, a ($C_1$-$C_6$)-hydroxyalkyl linker, a ($C_1$-$C_6$)-aminoalkyl linker, an aryl linker, a heteroaryl linker, a biaryl linker, or a benzyl linker. In some embodiments, the biohydrolyzable moiety is an amide comprising a ($C_1$-$C_6$)-alkyl linker, a ($C_1$-$C_6$) hydroxyalkyl linker, or a ($C_1$-$C_6$)-aminoalkyl linker. In some embodiments, the biohydrolyzable moiety is an amide comprising a ($C_1$-$C_6$)-alkyl linker or a ($C_1$-$C_6$) hydroxyalkyl linker. In some embodiments, the biohydrolyzable moiety is an amide comprising a ($C_1$-$C_6$)-alkyl linker or a ($C_1$-$C_6$)-aminoalkyl linker. In some embodiments, the biohydrolyzable moiety is an amide comprising a ($C_1$-$C_6$)-hydroxyalkyl linker or a ($C_1$-$C_6$) aminoalkyl linker. In some embodiments, the biohydrolyzable moiety is an amide comprising an aryl linker, a heteroaryl linker, a biaryl linker, or a benzyl linker. In some embodiments, the biohydrolyzable moiety is an amide comprising an aryl linker, a heteroaryl linker, or a benzyl linker. In some embodiments, the biohydrolyzable moiety is an amide comprising an aryl linker or a benzyl linker. In some embodiments, the biohydrolyzable moiety is an amide comprising an aryl linker or a heteroaryl linker.

In certain embodiments, the compounds of the invention are formulated into pharmaceutical compositions for administration to subjects in a biologically compatible form suitable for administration in vivo. According to another aspect, the present invention provides a pharmaceutical composition comprising a compound of Formula (I) in admixture with a pharmaceutically acceptable diluent and/or carrier. The pharmaceutically-acceptable carrier is "acceptable" in the sense of being compatible with the other ingredients of the composition and not deleterious to the recipient thereof. The pharmaceutically-acceptable carriers employed herein may be selected from various organic or inorganic materials that are used as materials for pharmaceutical formulations and which are incorporated as analgesic agents, buffers, binders, disintegrants, diluents, emulsifiers, excipients, extenders, glidants, solubilizers, stabilizers, suspending agents, tonicity agents, vehicles and viscosity-increasing agents. Pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others. In one embodiment, the term "pharmaceutically acceptable" means approved by a regulatory agency of the Federal or a state government or listed in the U.S. Pharmacopeia or other generally recognized pharmacopeia for use in animals, and more particularly in humans.

Surfactants such as, for example, detergents, are also suitable for use in the formulations. Specific examples of surfactants include polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; alkyl sulfates, in particular sodium lauryl sulfate and sodium cetyl sulfate; sodium dodecylbenzenesulphonate or sodium dioctyl sulphosuccinate; or fatty acids, in particular those derived from coconut oil, cationic surfactants, such as water-soluble quaternary ammonium salts of formula $N^+R'R''R'''R''''Y$—, in which the R radicals are identical or different optionally hydroxylated hydrocarbon radicals and y- is an anion of a strong acid, such as halide, sulfate and sulfonate anions; cetyltrimethylammonium bromide is one of the cationic surfactants which can be used, amine salts of formula N+R'R"R'", in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine.

When administered to a subject, the compound of Formula (I) and pharmaceutically acceptable carriers can be sterile. Suitable pharmaceutical carriers may also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, may also contain minor amounts of wetting or emulsifying agents, or pH buffering agents.

The pharmaceutical formulations of the present invention are prepared by methods well-known in the pharmaceutical arts. Optionally, one or more accessory ingredients (e.g., buffers, flavoring agents, surface active agents, and the like) also are added. The choice of carrier is determined by the solubility and chemical nature of the compounds, chosen route of administration and standard pharmaceutical practice.

Additionally, the compounds and/or compositions of the present invention are administered to a human or animal subject by known procedures including oral administration, sublingual or buccal administration. In one embodiment, the compound and/or composition is administered orally.

For oral administration, a formulation of the compounds of the invention may be presented in dosage forms such as capsules, tablets, powders, granules, or as a suspension or solution. Capsule formulations may be gelatin, soft-gel or solid. Tablets and capsule formulations may further contain one or more adjuvants, binders, diluents, disintegrants, excipients, fillers, or lubricants, each of which are known in the art. Examples of such include carbohydrates such as lactose or sucrose, dibasic calcium phosphate anhydrous, cornstarch, mannitol, xylitol, cellulose or derivatives thereof, microcrystalline cellulose, gelatin, stearates, silicon dioxide, talc, sodium starch glycolate, acacia, flavoring agents, preservatives, buffering agents, disintegrants, and colorants. Orally administered compositions may contain one or more optional agents such as, for example, sweetening agents such as fructose, aspartame or saccharin; flavoring agents such as peppermint, oil of wintergreen, or cherry; coloring agents; and preservative agents, to provide a pharmaceutically palatable preparation.

In some embodiments, the composition is in unit dose form such as a tablet, capsule or single-dose vial. Suitable unit doses, i.e., therapeutically effective amounts, may be determined during clinical trials designed appropriately for each of the conditions for which administration of a chosen compound is indicated and will, of course, vary depending on the desired clinical endpoint.

In accordance with the methods of the present invention, the compounds of the invention are administered to the subject in a therapeutically effective amount, for example to reduce or ameliorate symptoms related to aldose reductase activity in the subject. This amount is readily determined by the skilled artisan, based upon known procedures, including analysis of titration curves established in vivo and methods and assays disclosed herein.

In certain embodiments, the methods comprise administration of a therapeutically effective dosage of the compounds of the invention. In some embodiments, the therapeutically effective dosage is at least about 0.05 mg/kg body weight, at least about 0.1 mg/kg body weight, at least about 0.25 mg/kg body weight, at least about 0.3 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 350 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight. It will be recognized that any of the dosages listed herein may constitute an upper or lower dosage range, and may be combined with any other dosage to constitute a dosage range comprising an upper and lower limit.

In some embodiments, the methods comprise a single dosage or administration (e.g., as a single injection or deposition). Alternatively, the methods comprise administration once daily, twice daily, three times daily or four times daily to a subject in need thereof for a period of from about 2 to about 28 days, or from about 7 to about 10 days, or from about 7 to about 15 days, or longer. In some embodiments, the methods comprise chronic administration. In yet other embodiments, the methods comprise administration over the course of several weeks, months, years or decades. In still other embodiments, the methods comprise administration over the course of several weeks. In still other embodiments, the methods comprise administration over the course of several months. In still other embodiments, the methods comprise administration over the course of several years. In still other embodiments, the methods comprise administration over the course of several decades.

The dosage administered can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion. These are all readily determined and may be used by the skilled artisan to adjust or titrate dosages and/or dosing regimens.

The precise dose to be employed in the compositions will also depend on the route of administration, and should be decided according to the judgment of the practitioner and each patient's circumstances. In specific embodiments of the invention, suitable dose ranges for oral administration of the compounds of the invention are generally about 1 mg/day to about 1000 mg/day. In one embodiment, the oral dose is about 1 mg/day to about 800 mg/day. In one embodiment, the oral dose is about 1 mg/day to about 500 mg/day. In another embodiment, the oral dose is about 1 mg/day to about 250 mg/day. In another embodiment, the oral dose is about 1 mg/day to about 100 mg/day. In another embodiment, the oral dose is about 5 mg/day to about 50 mg/day. In another embodiment, the oral dose is about 5 mg/day. In another embodiment, the oral dose is about 10 mg/day. In another embodiment, the oral dose is about 20 mg/day. In another embodiment, the oral dose is about 30 mg/day. In another embodiment, the oral dose is about 40 mg/day. In another embodiment, the oral dose is about 50 mg/day. In another embodiment, the oral dose is about 60 mg/day. In another embodiment, the oral dose is about 70 mg/day. In another embodiment, the oral dose is about 100 mg/day. It will be recognized that any of the dosages listed herein may constitute an upper or lower dosage range, and may be combined with any other dosage to constitute a dosage range comprising an upper and lower limit.

Any of the compounds and/or compositions of the invention may be provided in a kit comprising the compounds and/or compositions. Thus, in one embodiment, the compound and/or composition of the invention is provided in a kit.

Those skilled in the art will recognize, or be able to ascertain using no more than routine experimentation, many equivalents to the specific embodiments of the invention described herein. Such equivalents are intended to be within the scope of the present invention.

The invention is further described by the following non-limiting Examples.

EXAMPLES

Examples are provided below to facilitate a more complete understanding of the invention. The following examples serve to illustrate the exemplary modes of making and practicing the invention. However, the scope of the invention is not to be construed as limited to specific embodiments disclosed in these Examples, which are illustrative only.

Example 1: Preparation of (2R,3R,4S,5R,6R)-2,3,5-trihydroxy-6-(hydroxymethyl)tetrahydro-2H-pyran-4-yl 2-(4-oxo-3-((5-(trifluoromethyl)benzo[d]thiazol-2-yl)methyl)-3,4-dihydrothieno[3,4-d]pyridazin-1-yl)acetate (Compound 21)

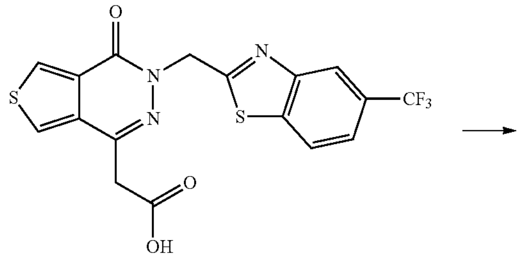

22

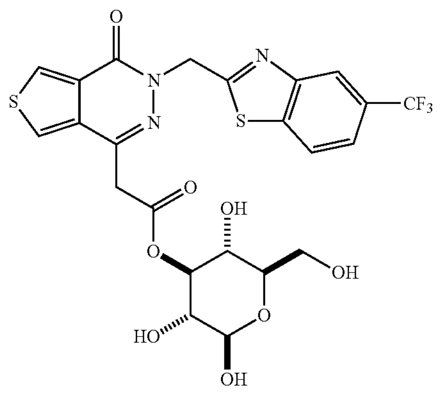

21

2-(4-oxo-3-((5-(trifluoromethyl)benzo[d]thiazol-2-yl)methyl)-3,4-dihydrothieno[3,4-d]pyridazin-1-yl)acetic acid (Compound 22) is prepared using the same method described previously in WO2017/038505.

(2R,3R,4S,5R,6R)-2,3,5-trihydroxy-6-(hydroxymethyl)tetrahydro-2H-pyran-4-yl 2-(4-oxo-3-((5-(trifluoromethyl)benzo[d]thiazol-2-yl)methyl)-3,4-dihydrothieno[3,4-d]pyridazin-1-yl)acetate (Compound 21): (Step 1) To a stirred solution of Compound 22 and (3aR,5S,6S,6aR)-5-((R)-2,2-dimethyl-1,3-dioxolan-4-yl)-2,2-dimethyltetrahydrofuro[2,3-d][1,3]dioxol-6-ol (Compound 9) in THF is added 1-ethyl-3-(3-dimethylaminopropyl)carbodiimide, $NEt_3$, and DMAP (catalytic). The reaction is stirred at room temperature until completion, as monitored by TLC. The reaction mixture is concentrated in vacuo. (Step 2) The crude residue is taken up in $CH_2Cl_2$ and trifluoroacetic acid is added. The reaction mixture is stirred at ambient temperature for 2 hours. The reaction mixture is concentrated in vacuo and the residue partitioned between ether and saturated aqueous $NaHCO_3$. The layers were separated and the ethereal layer washed with saturated aqueous $NaHCO_3$ (1×). The ethereal layers are combined and concentrated in vacuo. The resulting residue is purified via flash column chromatography over silica gel to give (2R,3R,4S,5R,6R)-2,3,5-trihydroxy-6-(hydroxymethyl)tetrahydro-2H-pyran-4-yl 2-(4-oxo-3-((5-(trifluoromethyl)benzo[d]thiazol-2-yl)methyl)-3,4-dihydrothieno[3,4-d]pyridazin-1-yl)acetate (Compound 21).

Example 2: Preparation of (2R Benzyl 2-(4-oxo-3-((5-(trifluoromethyl)benzo[d]thiazol-2-yl)methyl)-3,4-dihydrothieno[3,4-d]pyridazin-1-yl)acetate (Compound 23)

23

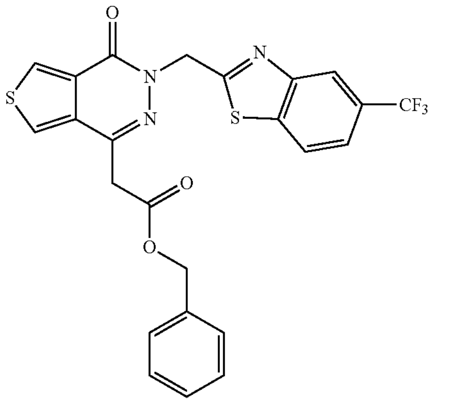

(2R Benzyl 2-(4-oxo-3-((5-(trifluoromethyl)benzo[d]thiazol-2-yl)methyl)-3,4-dihydrothieno[3,4-d]pyridazin-1-yl)acetate (Compound 23): The first step in the preparation described for Compound 21 was repeated except that benzyl alcohol was the reagent employed in place of (3aR,5S,6S,6aR)-5-((R)-2,2-dimethyl-1,3-dioxolan-4-yl)-2,2-dimethyltetrahydrofuro[2,3-d][1,3]dioxol-6-ol. The crude residue is purified via flash column chromatography over silica gel to give Benzyl 2-(4-oxo-3-((5-(trifluoromethyl)benzo[d]thiazol-2-yl)methyl)-3,4-dihydrothienof 3,4-d]pyridazin-1-yl)acetate (Compound 23).

Example 3: Preparation of (2R,3R,4S,5R,6R)-2,3,5-trihydroxy-6-(hydroxymethyl) tetrahydro-2H-pyran-4-yl 2-(8-oxo-7-((5-(trifluoromethyl)benzo[d]thiazol-2-yl)methyl)-7,8-dihydropyrazinof2,3-d] pyridazin-5-yl)acetate (Compound 25)

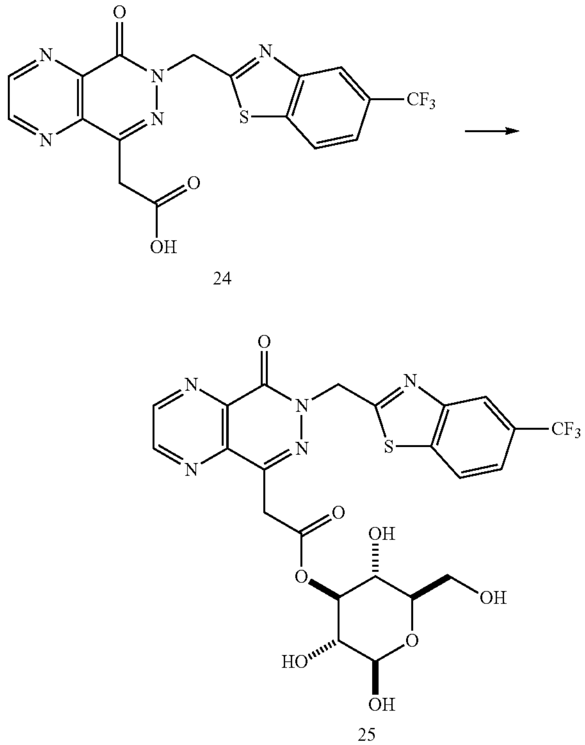

24

25

2-(8-oxo-7-((5-(trifluoromethyl)benzo[d]thiazol-2-yl) methyl)-7,8-dihydropyrazino[2,3-d]pyridazin-5-yl)acetic acid (Compound 24) is prepared using the same method described previously in U.S. Pat. No. 8,916,563.

(2R,3R,4S,5R,6R)-2,3,5-trihydroxy-6-(hydroxymethyl) tetrahydro-2H-pyran-4-yl 2-(8-oxo-7-((5-(trifluoromethyl) benzo[d]thiazol-2-yl)methyl)-7,8-dihydropyrazinof2,3-d] pyridazin-5-yl)acetate (Compound 25): To a stirred solution of Compound 24 and (3aR,5S,6S,6aR)-5-((R)-2,2-dimethyl-1,3-dioxolan-4-yl)-2,2-dimethyltetrahydrofuro[2,3-d][1,3] dioxol-6-ol (Compound 9) in THF is added 1-ethyl-3-(3-dimethylaminopropyl)carbodiimide, $NEt_3$, and DMAP (catalytic). The reaction is stirred at room temperature until completion, as monitored by TLC. The reaction mixture is concentrated in vacuo. The crude residue is taken up in $CH_2Cl_2$ and trifluoroacetic acid is added. The reaction mixture is stirred at ambient temperature for 2 hours. The reaction mixture is concentrated in vacuo and the residue partitioned between ether and saturated aqueous $NaHCO_3$. The layers were separated and the ethereal layer washed with saturated aqueous $NaHCO_3$ (1×). The ethereal layers are combined and concentrated in vacuo. The resulting residue is purified via flash column chromatography over silica gel to give (2R,3R,4S,5R,6R)-2,3,5-trihydroxy-6-(hydroxymethyl)tetrahydro-2H-pyran-4-yl 2-(8-oxo-7-((5-(trifluoromethyl)benzo[d]thiazol-2-yl)methyl)-7,8-dihydropyrazino[2,3-d]pyridazin-5-yl)acetate (Compound 25).

Example 4: Preparation of propyl 2-(4-oxo-3-((5-(trifluoromethyl)benzo[d]thiazol-2-yl)methyl)-3,4-dihydrothieno[3,4-d]pyridazin-1-yl)acetate (Compound 26)

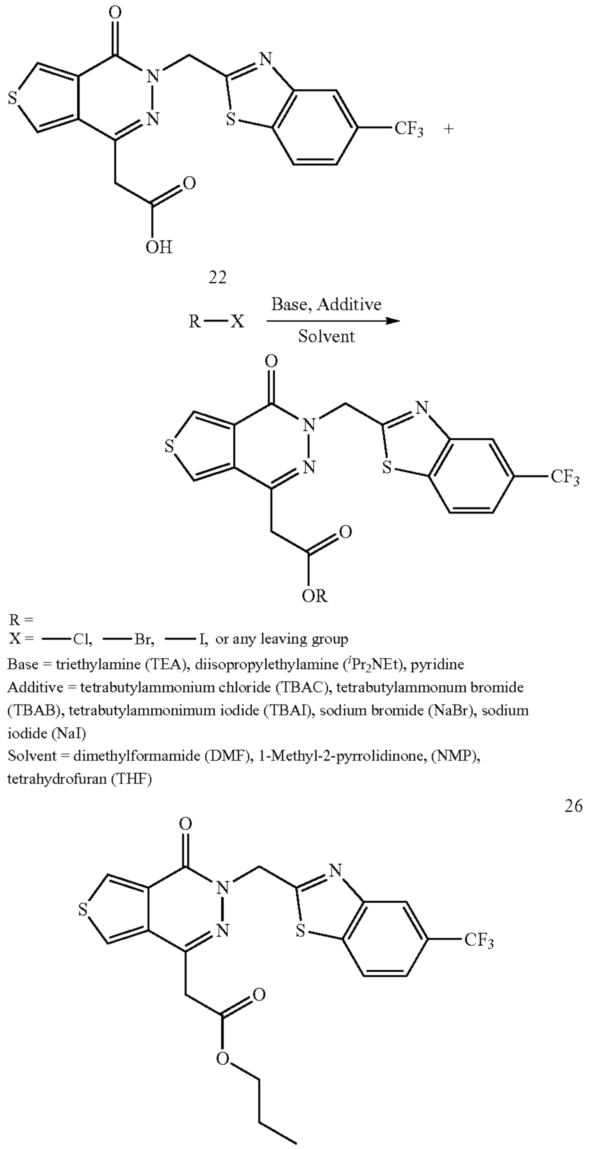

22

26

To a heterogeneous mixture of Compound 22 (0.150 g, $3.53\times10^{-4}$ mol), 1-bromopropane (39% L, $4.24\times10^{-4}$ mol), and TBAB (0.119 g, $3.70\times10^{-4}$ mol) in DMF (3.0 mL) was added TEA (64 μL, $4.59\times10^{-4}$ mol). The resulting homogeneous reaction mixture was stirred at ambient temperature overnight. The reaction mixture was partitioned between diethyl ether and water, the layers separated, and the ethereal layer washed sequentially with water (1×), saturated aqueous $NaHCO_3$ (1×), water (1×), 1.0M HCl(aq) (1×), and brine (1×). The ethereal layer was dried over $Na_2SO_4$, filtered, and concentrated in vacuo. The obtained residue was purified via flash chromatography over silica gel (monitored by thin layer chromatography) and eluted with 2:1 (v/v) hexanes: ethyl acetate. Evaporation of the collected fractions yielded 0.105 g (64% yield) of propyl 2-(4-oxo-3-((5-(trifluoromethyl)benzo[d]thiazol-2-yl)methyl)-3,4-dihydrothieno[3,4-d]pyridazin-1-yl)acetate (Compound 26): $^1$H NMR (acetone-$d_6$, 400 MHz): $\delta_{ppm}$ 8.60 (d, J=3.2 Hz, 1H), 8.30 (d, J=3.2 Hz, 1H), 8.29 (s, 1H), 8.26 (d, J=8.4 Hz, 1H), 7.74 (d, J=8.4 Hz, 1H), 5.74 (s, 2H), 4.04 (t, J=6.4 Hz, 2H), 3.97 (s, 2H), 1.61-1.52 (m, 2H), 0.81 (t, J=7.2 Hz, 3H)); MS ESI (m/z) 468 $(M+1)^+$.

Example 5: Preparation of isopropyl 2-(4-oxo-3-((5-(trifluoromethyl)benzo[d]thiazol-2-yl)methyl)-3,4-dihydrothieno[3,4-d]pyridazin-1-yl)acetate (Compound 27)

27

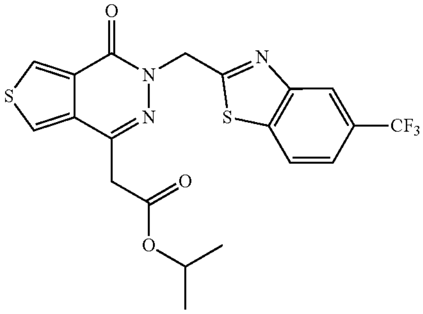

To a heterogeneous mixture of Compound 22 (0.150 g, $3.53\times10^{-4}$ mol), 2-bromopropane (40 μL, $4.24\times10^{-4}$ mol), and TBAB (0.119 g, $3.70\times10^{-4}$ mol) in DMF (3.0 mL) was added TEA (64 μL, $4.59\times10^{-4}$ mol). The resulting homogeneous reaction mixture was stirred at ambient temperature overnight. The reaction mixture was partitioned between diethyl ether and water, the layers separated, and the ethereal layer washed sequentially with water (1×), saturated aqueous $NaHCO_3$ (1×), water (1×), 1.0M $HCl_{(aq)}$ (1×), and brine (1×). The ethereal layer was dried over $Na_2SO_4$, filtered, and concentrated in vacuo. The obtained residue was purified via flash chromatography over silica gel (monitored by thin layer chromatography) and eluted with 2:1 (v/v) hexanes:ethyl acetate. Evaporation of the collected fractions yielded 0.052 g (32% yield) of isopropyl 2-(4-oxo-3-((5-(trifluoromethyl)benzo[d]thiazol-2-yl)methyl)-3,4-dihydrothieno[3,4-d]pyridazin-1-yl)acetate (Compound 27): $^1$H NMR ($CDCl_3$, 400 MHz): $\delta_{ppm}$ 8.46 (d, J=3.2 Hz, 1H), 8.29 (s, 1H), 7.92 (d, J=8.4 Hz, 1H), 7.83 (d, J=3.2 Hz, 1H), 7.59 (d, J=8.4 Hz, 1H), 5.75 (s, 2H), 5.04 (sept, J=6.4 Hz, 1H), 3.84 (s, 2H), 1.21 (d, J=6.4 Hz, 6H); MS ESI (m/z) 468 $(M+1)^+$.

Example 6: butyl 2-(4-oxo-3-((5-(trifluoromethyl)benzo[d]thiazol-2-yl)methyl)-3,4-dihydrothieno[3,4-d]pyridazin-1-yl)acetate (Compound 28)

To a heterogeneous mixture of Compound 22 (0.150 g, $3.53\times10^{-4}$ mol), 1-bromobutane (45 μL, $4.24\times10^{-4}$ mol), and TBAB (0.119 g, $3.70\times10^{-4}$ mol) in DMF (3.0 mL) was added TEA (64 μL, $4.59\times10^{-4}$ mol). The resulting homogeneous reaction mixture was stirred at ambient temperature overnight. The reaction mixture was partitioned between diethyl ether and water, the layers separated, and the ethereal layer washed sequentially with water (1×), saturated aqueous $NaHCO_3$ (1×), water (1×), 1.0M $HCl_{(aq)}$ (1×), and brine (1×). The ethereal layer was dried over $Na_2SO_4$, filtered, and concentrated in vacuo. The obtained residue was purified via flash chromatography over silica gel (monitored by thin layer chromatography) and eluted with 2:1 (v/v) hexanes:ethyl acetate. Evaporation of the collected fractions yielded 0.103 g (61% yield) of butyl 2-(4-oxo-3-((5-(trifluoromethyl)benzo[d]thiazol-2-yl)methyl)-3,4-dihydrothieno[3,4-d]pyridazin-1-yl)acetate (Compound 28): $^1$H NMR (acetone-$d_6$, 400 MHz): $\delta_{ppm}$ 8.60 (d, J=2.8 Hz, 1H), 8.30-8.28 (m, 2H), 8.26 (d, J=8.4 Hz, 1H), 7.74 (d, J=8.4 Hz, 1H), 5.74 (s, 2H), 4.08 (t, J=6.8 Hz, 2H), 3.97 (s, 2H), 1.55-1.50 (m, 2H), 1.29-1.21 (m, 2H), 0.81 (t, J=7.2 Hz, 3H); MS ESI (m/z) 482 $(M+1)^+$.

28

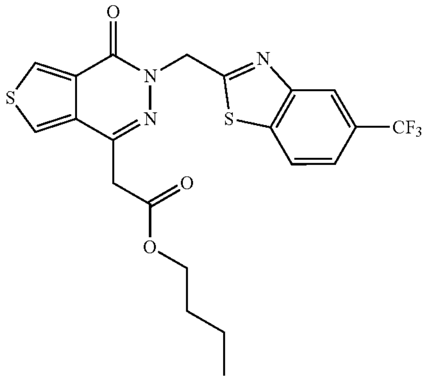

Example 7: Preparation of sec-butyl 2-(4-oxo-3-((5-(trifluoromethyl)benzo[d]thiazol-2-yl)methyl)-3,4-dihydrothieno[3,4-d]pyridazin-1-yl)acetate (Compound 29)

29

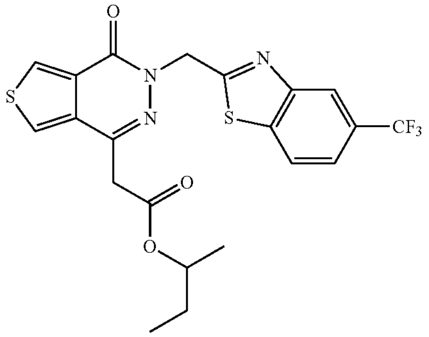

To a heterogeneous mixture of Compound 22 (0.150 g, $3.53\times10^{-4}$ mol), 2-bromobutane (46 μL, $4.24\times10^{-4}$ mol), and TBAB (0.119 g, $3.70\times10^{-4}$ mol) in DMF (3.0 mL) was added TEA (64 μL, $4.59\times10^{-4}$ mol). The resulting homogeneous reaction mixture was stirred at ambient temperature overnight. The reaction mixture was partitioned between diethyl ether and water, the layers separated, and the ethereal layer washed sequentially with water (1×), saturated aqueous $NaHCO_3$ (1×), water (1×), 1.0M $HCl_{(aq)}$ (1×), and brine (1×). The ethereal layer was dried over $Na_2SO_4$, filtered, and concentrated in vacuo. The obtained residue was purified via flash chromatography over silica gel (monitored by thin layer chromatography) and eluted with 2:1 (v/v) hexanes:ethyl acetate. Evaporation of the collected fractions yielded 0.028 g (17% yield) of sec-butyl 2-(4-oxo-3-((5-(trifluoromethyl)benzo[d]thiazol-2-yl)methyl)-3,4-dihydrothieno[3,4-d]pyridazin-1-yl)acetate (Compound IV): $^1$H NMR (acetone-$d_6$, 400 MHz): $\delta_{ppm}$ 8.60 (d, J=2.4 Hz, 1H), 8.30-8.28 (m, 2H), 8.26 (d, J=8.4 Hz, 1H), 7.74 (d, J=8.4 Hz, 1H), 5.74 (s, 2H), 4.84-4.79 (m, 1H), 3.95 (s, 2H), 1.53-1.46 (m, 2H), 1.13 (d, J=6.0 Hz, 3H), 0.76 (t, J=8 Hz, 3H); MS ESI (m/z) 482 $(M+1)^+$.

Example 8: Preparation of benzyl 2-(4-oxo-3-((5-(trifluoromethyl)benzo[d]thiazol-2-yl)methyl)-3,4-dihydrothieno[3,4-d]pyridazin-1-yl)acetate (Compound 23)

23

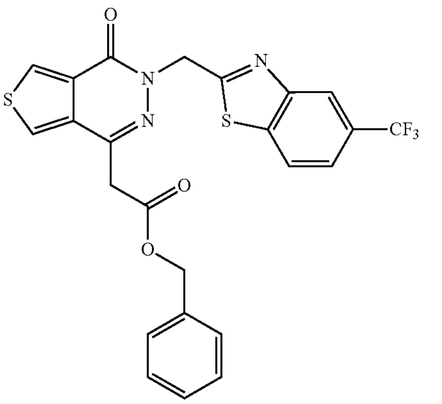

To a heterogeneous mixture of Compound 22 (0.150 g, $3.53\times10^{-4}$ mol), benzyl bromide (50 μL, $4.24\times10^{-4}$ mol), and TBAB (0.119 g, $3.70\times10^{-4}$ mol) in DMF (3.0 mL) was added TEA (64 μL, $4.59\times10^{-4}$ mol). The resulting homogeneous reaction mixture was stirred at ambient temperature overnight. The reaction mixture was partitioned between diethyl ether and water, the layers separated, and the ethereal layer washed sequentially with water (1×), saturated aqueous $NaHCO_3$ (1×), water (1×), 1.0M $HCl_{(aq)}$ (1×), and brine (1×). The ethereal layer was dried over $Na_2SO_4$, filtered, and concentrated in vacuo. The obtained residue was purified via flash chromatography over silica gel (monitored by thin layer chromatography) and eluted with 2:1 (v/v) hexanes:ethyl acetate. Evaporation of the collected fractions yielded 0.120 g (66% yield) of benzyl 2-(4-oxo-3-((5-(trifluoromethyl)benzo[d]thiazol-2-yl)methyl)-3,4-dihydrothieno[3,4-d]pyridazin-1-yl)acetate (Compound 23): $^1$H NMR ($CDCl_3$, 400 MHz): $\delta_{ppm}$ 8.45 (d, J=2.8 Hz, 1H), 8.28 (s, 1H), 7.89 (d, J=8.4 Hz, 1H), 7.73 (d, J=2.8 Hz, 1H), 7.59 (d, J=8.4 Hz, 1H), 7.31-7.27 (m, 5H), 5.73 (s, 2H), 5.16 (s, 2H), 3.92 (s, 2H); MS ESI (m/z) 516 $(M+1)^+$.

Example 9: Preparation of 2-methoxy-2-oxoethyl 2-(4-oxo-3-((5-(trifluoromethyl)benzo[d]thiazol-2-yl)methyl)-3,4-dihydrothieno[3,4-d]pyridazin-1-yl) acetate (Compound 30)

30

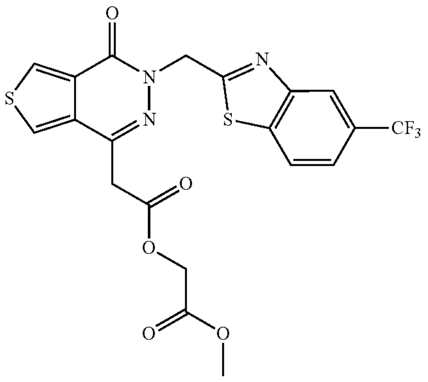

To a heterogeneous mixture of Compound 22 (0.100 g, $2.35\times10^{-4}$ mol), methyl bromoacetate (25 μL, $2.59\times10^{-4}$ mol), and TBAB (0.080 g, $2.47\times10^{-4}$ mol) in DMF (3.0 mL) was added TEA (43 μL, $3.06\times10^{-4}$ mol). The resulting homogeneous reaction mixture was stirred at ambient temperature overnight. The reaction mixture was partitioned between diethyl ether and water, the layers separated, and the ethereal layer washed sequentially with water (1×), saturated aqueous $NaHCO_3$ (1×), water (1×), 1.0M $HCl_{(aq)}$ (1×), and brine (1×). The ethereal layer was dried over $Na_2SO_4$, filtered, and concentrated in vacuo. The obtained residue was purified via flash chromatography over silica gel (monitored by thin layer chromatography) and eluted with 2:1 (v/v) hexanes:ethyl acetate. Evaporation of the collected fractions yielded 0.116 g (99% yield) of 2-methoxy-2-oxoethyl 2-(4-oxo-3-((5-(trifluoromethyl)benzo[d]thiazol-2-yl)methyl)-3,4-dihydrothieno[3,4-d]pyridazin-1-yl)acetate (Compound 30): $^1$H NMR ($CDCl_3$, 400 MHz): $\delta_{ppm}$ 8.46 (d, J=3.2 Hz, 1H), 8.29 (s, 1H), 7.97 (d, J=3.2 Hz, 1H), 7.93 (d, J=8.4 Hz, 1H), 7.60 (d, J=8.4 Hz, 1H), 5.75 (s, 2H), 4.68 (s, 2H), 4.00 (s, 2H), 3.75 (s, 3H); MS ESI (m/z) 498 $(M+1)^+$.

Example 10: Preparation of 2-ethoxy-2-oxoethyl 2-(4-oxo-3-((5-(trifluoromethyl)benzo[d]thiazol-2-yl)methyl)-3,4-dihydrothieno[3,4-d]pyridazin-1-yl) acetate (Compound 31)

31

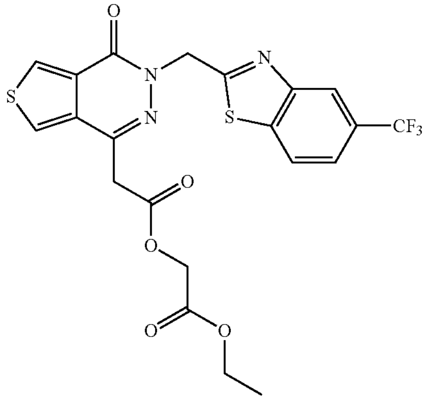

To a heterogeneous mixture of Compound 22 (0.100 g, $2.35\times10^{-4}$ mol), ethyl bromoacetate (29 μL, $2.59\times10^{-4}$ mol), and TBAB (0.080 g, $2.47\times10^{-4}$ mol) in DMF (3.0 mL) was added TEA (43 μL, $3.06\times10^{-4}$ mol). The resulting homogeneous reaction mixture was stirred at ambient temperature overnight. The reaction mixture was partitioned between diethyl ether and water, the layers separated, and the ethereal layer washed sequentially with water (1×), saturated aqueous $NaHCO_3$ (1×), water (1×), 1.0M $HCl_{(aq)}$ (1×), and brine (1×). The ethereal layer was dried over $Na_2SO_4$, filtered, and concentrated in vacuo. The obtained residue was purified via flash chromatography over silica gel (monitored by thin layer chromatography) and eluted with 2:1 (v/v) hexanes: ethyl acetate. Evaporation of the collected fractions yielded 0.110 g (92% yield) of 2-ethoxy-2-oxoethyl 2-(4-oxo-3-((5-(trifluoromethyl)benzo[d]thiazol-2-yl)methyl)-3,4-dihydrothieno[3,4-d]pyridazin-1-yl)acetate (Compound 31): $^1H$ NMR ($CDCl_3$, 400 MHz): $\delta_{ppm}$ 8.46 (d, J=3.2 Hz, 1H), 8.29 (s, 1H), 7.97 (d, J=3.2 Hz, 1H), 7.93 (d, J=8.4 Hz, 1H), 7.60 (d, J=8.4 Hz, 1H), 5.75 (s, 2H), 4.66 (s, 2H), 4.20 (q, J=7.2 Hz, 2H), 4.00 (s, 2H), 1.25 (t, J=7.2 Hz, 3H); MS ESI (m/z) 512 $(M+1)^+$.

Example 11: Preparation of 2-isopropoxy-2-oxoethyl 2-(4-oxo-3-((5-(trifluoromethyl)benzo[d]thiazol-2-yl)methyl)-3,4-dihydrothieno[3,4-d] pyridazin-1-yl)acetate (Compound 32)

31

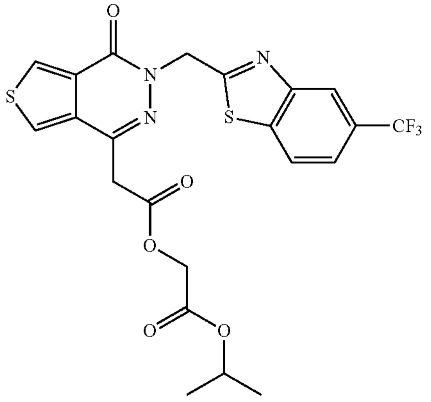

To a heterogeneous mixture of Compound 22 (0.100 g, $2.35\times10^{-4}$ mol), isopropyl bromoacetate (33 μL, $2.59\times10^{-4}$ mol), and TBAB (0.080 g, $2.47\times10^{-4}$ mol) in DMF (3.0 mL) was added TEA (43 μL, $3.06\times10^{-4}$ mol). The resulting homogeneous reaction mixture was stirred at ambient temperature overnight. The reaction mixture was partitioned between diethyl ether and water, the layers separated, and the ethereal layer washed sequentially with water (1×), saturated aqueous $NaHCO_3$ (1×), water (1×), 1.0M $HCl_{(aq)}$ (1×), and brine (1×). The ethereal layer was dried over $Na_2SO_4$, filtered, and concentrated in vacuo. The obtained residue was purified via flash chromatography over silica gel (monitored by thin layer chromatography) and eluted with 2:1 (v/v) hexanes:ethyl acetate. Evaporation of the collected fractions yielded 0.102 g (82% yield) of 2-isopropoxy-2-oxoethyl 2-(4-oxo-3-((5-(trifluoromethyl)benzo[d]thiazol-2-yl)methyl)-3,4-dihydrothieno[3,4-d]pyridazin-1-yl)acetate (Compound 32): $^1H$ NMR ($CDCl_3$, 400 MHz): $\delta_{ppm}$ 8.45 (d, J=3.2 Hz, 1H), 8.29 (s, 1H), 7.98 (d, J=3.2 Hz, 1H), 7.93 (d, J=8.4 Hz, 1H), 7.60 (d, J=8.4 Hz, 1H), 5.75 (s, 2H), 5.07 (sept, J=6.4 Hz, 1H), 4.62 (s, 2H), 4.00 (s, 2H), 1.23 (d, J=6.4 Hz, 6H); MS ESI (m/z) 526 $(M+1)^+$.

Example 12: Preparation of 2-(tert-butoxy)-2-oxoethyl 2-(4-oxo-3-((5-(trifluoromethyl)benzo[d]thiazol-2-yl)methyl)-3,4-dihydrothieno[3,4-d] pyridazin-1-yl)acetate (Compound 33)

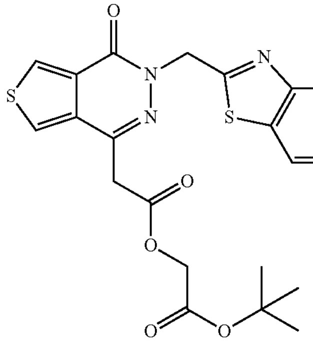

33

To a heterogeneous mixture of Compound 22 (0.150 g, $3.53\times10^{-4}$ mol), tert-butylbromoacetate (57 μL, $3.88\times10^{-4}$ mol), and TBAB (0.119 g, $3.70\times10^{-4}$ mol) in DMF (3.0 mL) was added TEA (64 μL, $4.59\times10^{-4}$ mol). The resulting homogeneous reaction mixture was stirred at ambient temperature overnight. The reaction mixture was partitioned between diethyl ether and water, the layers separated, and the ethereal layer washed sequentially with water (1×), saturated aqueous $NaHCO_3$ (1×), water (1×), 1.0M $HCl_{(aq)}$ (1×), and brine (1×). The ethereal layer was dried over $Na_2SO_4$, filtered, and concentrated in vacuo. The obtained residue was dissolved in a minimum amount of EtOAc and then hexanes added to precipitate out a white solid. The solid was collected via vacuum filtration and washed with hexanes. Subsequent drying under vacuum yielded 0.165 g (87% yield) of 2-(tert-butoxy)-2-oxoethyl 2-(4-oxo-3-((5-(trifluoromethyl)benzo[d]thiazol-2-yl)methyl)-3,4-dihydrothieno[3,4-d]pyridazin-1-yl)acetate (Compound 33): $^1H$ NMR ($CDCl_3$, 400 MHz): $\delta_{ppm}$ 8.45 (d, J=2.8 Hz, 1H), 8.29 (s, 1H), 7.99 (d, J=2.8 Hz, 1H), 7.92 (d, J=8.4 Hz, 1H), 7.59 (d, J=8.4 Hz, 1H), 5.75 (s, 2H), 4.55 (s, 2H), 3.99 (s, 2H), 1.45 (s, 9H); MS ESI (m/z) 540 $(M+1)^+$.

Example 13: Preparation of 2-(2-(4-oxo-3-((5-(trifluoromethyl)benzo[d]thiazol-2-yl)methyl)-3,4-dihydrothieno[3,4-d]pyridazin-1-yl)acetoxy)acetic acid (Compound 34)

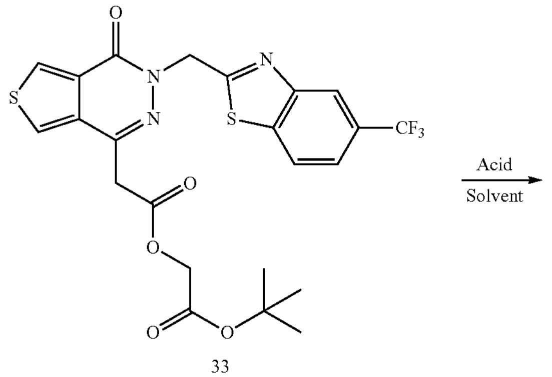

33

-continued

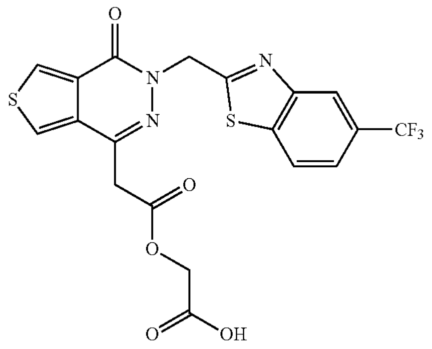

34

Acid = HCl, $H_2SO_4$, $H_3PO_4$, TFA
Solvent = ether, THF, dioxane. EtOAc

To a solution of Compound 33 (0.155 g, $2.87\times10^{-4}$ mol) in EtOAc (1.0 mL) at 0° C. was added $H_3PO_4$ (2.0 mL, >85% wt. in $H_2O$). The reaction mixture was warmed to ambient temperature and stirred for 2 hours. Subsequently, diluted the reaction mixture with EtOAc and washed the organic layer with water (4×) followed by brine (1×). The organic layer was dried over $Na_2SO_4$, filtered, and concentrated in vacuo. The obtained solid was suspended in ether and collected via vacuum filtration. The solid was washed with cold (0° C.) EtOAc (2×) and dried under vacuum to yield 0.061 g (44% yield) of 2-(2-(4-oxo-3-((5-(trifluoromethyl)benzo[d]thiazol-2-yl)methyl)-3,4-dihydrothieno[3,4-d]pyridazin-1-yl)acetoxy)acetic acid (Compound 34): $^1H$ NMR ($CD_3OD$, 400 MHz): $\delta_{ppm}$ 8.58 (d, J=3.2 Hz, 1H), 8.31 (d, J=3.2 Hz, 1H), 8.24 (s, 1H), 8.15 (d, J=8.4 Hz, 1H), 7.68 (d, J=8.4 Hz, 1H), 5.76 (s, 2H), 4.66 (s, 2H), 4.09 (s, 2H); MS ESI (m/z) 484 $(M+1)^+$.

Example 14: Preparation of pentan-2-yl 2-(4-oxo-3-((5-(trifluoromethyl)benzo[d]thiazol-2-yl)methyl)-3,4-dihydrothieno[3,4-d]pyridazin-1-yl)acetate (Compound 35)

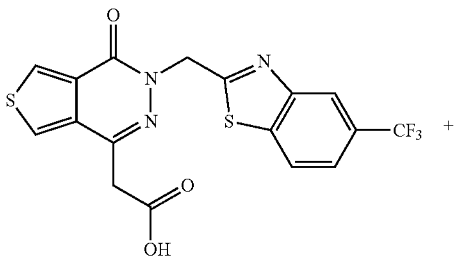

22

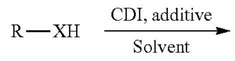

-continued

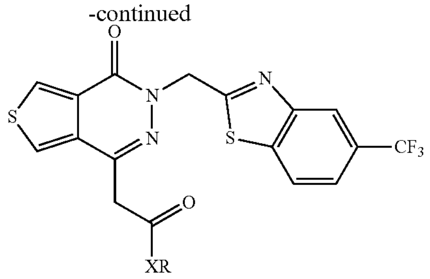

R =
X = O, NH, $NR^2$
Additive = none, 4-dimethylaminopyridine (DMAP)
Solvent = dimethylformamide (DMF), 1-Methyl-2-pyrrolidinone, (NMP), tetrahydrofuran (THF)

35

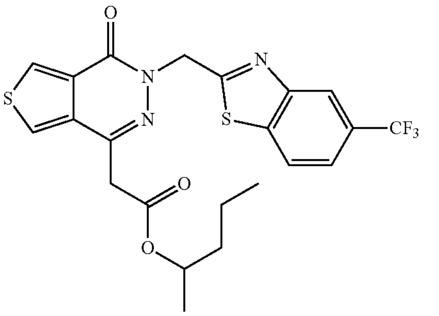

To a solution of Compound 22 (0.050 g, $1.18\times10^{-4}$ mol) in DMF (1.5 mL) was added CDI (23 mg, $1.41\times10^{-4}$ mol). The reaction mixture was stirred at ambient temperature for 1 h before 2-pentanol (18 μL, $1.65\times10^{-4}$ mol) and DMAP (7 mg, $5.88\times10^{-5}$ mol) were added. The resulting reaction mixture was warmed to 40° C. and stirred overnight. Cooled the reaction mixture to ambient temperature and partitioned between diethyl ether and water, the layers separated, and the ethereal layer washed sequentially with water (1×), saturated aqueous $NaHCO_3$ (1×), water (1×), 1.0M $HCl_{(aq)}$ (1×), and brine (1×). The ethereal layer was dried over $Na_2SO_4$, filtered, and concentrated in vacuo. The obtained residue was purified via flash chromatography over silica gel (monitored by thin layer chromatography) and eluted with 2:1 (v/v) hexanes:ethyl acetate. Evaporation of the collected fractions yielded 0.031 g (53% yield) of pentan-2-yl 2-(4-oxo-3-((5-(trifluoromethyl)benzo[d]thiazol-2-yl)methyl)-3,4-dihydrothieno[3,4-d]pyridazin-1-yl)acetate (Compound 35): $^1$H NMR ($CDCl_3$, 400 MHz): $\delta_{ppm}$ 8.46 (d, J=2.8 Hz, 1H), 8.29 (s, 1H), 7.92 (d, J=8.4 Hz, 1H), 7.83 (d, J=2.8 Hz, 1H), 7.60 (d, J=8.4 Hz, 1H), 5.76 (s, 2H), 4.97-4.90 (m, 1H), 3.85 (s, 2H), 1.49-1.45 (m, 2H), 1.29-1.20 (m, 2H), 1.17 (d, J=6.4 Hz, 3H), 0.82 (t, J=6.8 Hz, 3H); MS ESI (m/z) 496 $(M+1)^+$.

Example 15: Preparation of pentan-3-yl 2-(4-oxo-3-((5-(trifluoromethyl)benzo[d]thiazol-2-yl)methyl)-3,4-dihydrothieno[3,4-d]pyridazin-1-yl)acetate (Compound 36)

36

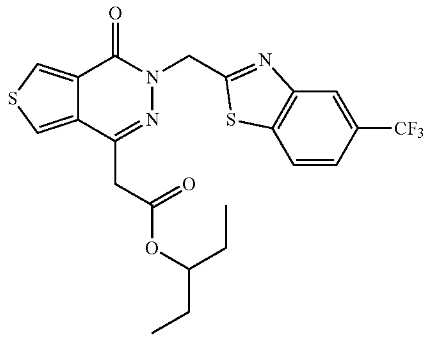

To a solution of Compound 22 (0.100 g, $2.35\times10^{-4}$ mol) in DMF (3.0 mL) was added CDI (46 mg, $2.82\times10^{-4}$ mol). The reaction mixture was stirred at ambient temperature for 1 h before 3-pentanol (35 μL, $3.29\times10^{-4}$ mol) and DMAP (14 mg, $1.18\times10^{-4}$ mol) were added. The resulting reaction mixture was warmed to 40° C. and stirred overnight. Cooled the reaction mixture to ambient temperature and partitioned between diethyl ether and water, the layers separated, and the ethereal layer washed sequentially with water (1×), saturated aqueous $NaHCO_3$ (1×), water (1×), 1.0M $HCl_{(aq)}$ (1×), and brine (1×). The ethereal layer was dried over $Na_2SO_4$, filtered, and concentrated in vacuo. The obtained residue was purified via flash chromatography over silica gel (monitored by thin layer chromatography) and eluted with 2:1 (v/v) hexanes:ethyl acetate. Evaporation of the collected fractions yielded 0.057 g (49% yield) of pentan-3-yl 2-(4-oxo-3-((5-(trifluoromethyl)benzo[d]thiazol-2-yl)methyl)-3,4-dihydrothieno[3,4-d]pyridazin-1-yl)acetate (Compound 36): $^1$H NMR ($CDCl_3$, 400 MHz): $\delta_{ppm}$ 8.46 (d, J=2.8 Hz, 1H), 8.29 (s, 1H), 7.91 (d, J=8.4 Hz, 1H), 7.83 (d, J=2.8 Hz, 1H), 7.60 (d, J=8.4 Hz, 1H), 5.76 (s, 2H), 4.77 (pent, J=6.4 Hz, 1H), 3.87 (s, 2H), 1.55-1.45 (m, 4H), 0.76 (t, J=7.6 Hz, 6H); MS ESI (m/z) 496 $(M+1)^+$.

Example 16: Preparation of cyclohexyl 2-(4-oxo-3-((5-(trifluoromethyl)benzo[d]thiazol-2-yl)methyl)-3,4-dihydrothieno[3,4-d]pyridazin-1-yl)acetate (Compound 37)

37

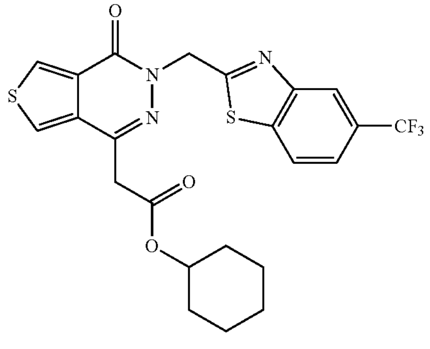

To a solution of Compound 22 (0.100 g, $2.35\times10^{-4}$ mol) in DMF (3.0 mL) was added CDI (46 mg, $2.82\times10^{-4}$ mol). The reaction mixture was stirred at ambient temperature for 1 h before cyclohexanol (35 μL, $3.29\times10^{-4}$ mol) and DMAP (14 mg, $1.18\times10^{-4}$ mol) were added. The resulting reaction mixture was warmed to 40° C. and stirred overnight. Cooled the reaction mixture to ambient temperature and partitioned between diethyl ether and water, the layers separated, and the ethereal layer washed sequentially with water (1×), saturated aqueous $NaHCO_3$ (1×), water (1×), 1.0M $HCl_{(aq)}$ (1×), and brine (1×). The ethereal layer was dried over $Na_2SO_4$, filtered, and concentrated in vacuo. The obtained residue was purified via flash chromatography over silica gel (monitored by thin layer chromatography) and eluted with 2:1 (v/v) hexanes:ethyl acetate. Evaporation of the collected fractions yielded 0.084 g (71% yield) of 2-(4-oxo-3-((5-(trifluoromethyl)benzo[d]thiazol-2-yl)methyl)-3,4-dihydrothieno[3,4-d]pyridazin-1-yl)acetate (Compound 37): $^1H$ NMR ($CDCl_3$, 400 MHz): $\delta_{ppm}$ 8.46 (d, J=3.2 Hz, 1H), 8.29 (s, 1H), 7.92 (d, J=8.0 Hz, 1H), 7.83 (d, J=3.2 Hz, 1H), 7.60 (d, J=8.0 Hz, 1H), 5.76 (s, 2H), 4.82-4.77 (m, 1H), 3.85 (s, 2H), 1.78-1.73 (m, 2H), 1.61-1.56 (m, 1H), 1.53-1.45 (m, 1H), 1.39-1.24 (m, 5H), 1.20-1.14 (m, 1H); MS ESI (m/z) 508 $(M+1)^+$.

Example 17: Preparation of methyl (S)-2-(2-(4-oxo-3-((5-(trifluoromethyl)benzo[d]thiazol-2-yl)methyl)-3,4-dihydrothieno[3,4-d]pyridazin-1-yl)acetoxy) propanoate (Compound 38)

38

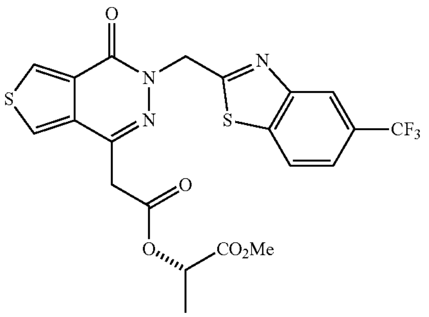

To a solution of Compound 22 (0.300 g, $7.06\times10^{-4}$ mol) in DMF (5.0 mL) was added CDI (0.137 g, $8.47\times10^{-4}$ mol). The reaction mixture was stirred at ambient temperature for 1 h before methyl L-(−)-lactate (94 μL, $9.88\times10^{-4}$ mol) and DMAP (43 mg, $3.53\times10^{-4}$ mol) were added. The resulting reaction mixture was warmed to 40° C. and stirred overnight. Cooled the reaction mixture to ambient temperature and partitioned between diethyl ether and water, the layers separated, and the ethereal layer washed sequentially with water (1×), saturated aqueous $NaHCO_3$ (1×), water (1×), 1.0M $HCl_{(aq)}$ (1×), and brine (1×). The ethereal layer was dried over $Na_2SO_4$, filtered, and concentrated in vacuo. The obtained residue was purified via flash chromatography over silica gel (monitored by thin layer chromatography) and eluted with 2:1 (v/v) hexanes:ethyl acetate to 1:1 (v/v) hexanes:ethyl acetate. Evaporation of the collected fractions yielded 0.094 g (26% yield) of methyl (S)-2-(2-(4-oxo-3-((5-(trifluoromethyl)benzo[d]thiazol-2-yl)methyl)-3,4-dihydrothieno[3,4-d]pyridazin-1-yl)acetoxy)propanoate_(Compound 38): $^1H$ NMR ($CDCl_3$, 400 MHz): $\delta_{ppm}$ 8.46 (d, J=3.2 Hz, 1H), 8.29 (s, 1H), 7.95 (d, J=3.2 Hz, 1H), 7.92 (d, J=8.4 Hz, 1H), 7.60 (d, J=8.4 Hz, 1H), 5.75 (d, J=4.4 Hz, 2H), 5.14 (q, J=6.8 Hz, 1H), 3.97 (d, J=9.6 Hz, 2H), 3.72 (s, 3H), 1.48 (d, J=6.8 Hz, 3H); MS ESI (m/z) 512 $(M+1)^+$.

Example 18: Preparation of methyl (R)-2-(2-(4-oxo-3-((5-(trifluoromethyl)benzo[d]thiazol-2-yl)methyl)-3,4-dihydrothieno[3,4-d]pyridazin-1-yl)acetoxy)propanoate (Compound 39)

39

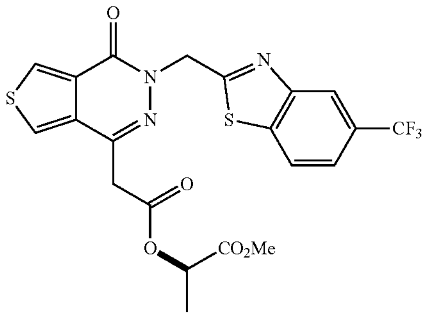

To a solution of Compound 22 (0.300 g, $7.06\times10^{-4}$ mol) in DMF (5.0 mL) was added CDI (0.137 g, $8.47\times10^{-4}$ mol). The reaction mixture was stirred at ambient temperature for 1 h before methyl D-(+)-lactate (94 μL, $9.88\times10^{-4}$ mol) and DMAP (43 mg, $3.53\times10^{-4}$ mol) were added. The resulting reaction mixture was warmed to 40° C. and stirred overnight. Cooled the reaction mixture to ambient temperature and partitioned between diethyl ether and water, the layers separated, and the ethereal layer washed sequentially with water (1×), saturated aqueous $NaHCO_3$ (1×), water (1×), 1.0M $HCl_{(aq)}$ (1×), and brine (1×). The ethereal layer was dried over $Na_2SO_4$, filtered, and concentrated in vacuo. The obtained residue was purified via flash chromatography over silica gel (monitored by thin layer chromatography) and eluted with 2:1 (v/v) hexanes:ethyl acetate to 1:1 (v/v) hexanes:ethyl acetate. Evaporation of the collected fractions yielded 0.099 g (27% yield) of methyl (R)-2-(2-(4-oxo-3-((5-(trifluoromethyl)benzo[d]thiazol-2-yl)methyl)-3,4-dihydrothieno[3,4-d]pyridazin-1-yl)acetoxy)propanoate (Compound 39): $^1H$ NMR ($CDCl_3$, 400 MHz): $\delta_{ppm}$ 8.46 (d, J=3.2 Hz, 1H), 8.29 (s, 1H), 7.95 (d, J=3.2 Hz, 1H), 7.92 (d, J=8.4 Hz, 1H), 7.60 (d, J=8.4 Hz, 1H), 5.75 (d, J=4.4 Hz, 2H), 5.14 (q, J=6.8 Hz, 1H), 3.97 (d, J=9.6 Hz, 2H), 3.72 (s, 3H), 1.48 (d, J=6.8 Hz, 3H); MS ESI (m/z) 512 $(M+1)^+$.

Example 19: Preparation of ethyl (S)-2-(2-(4-oxo-3-((5-(trifluoromethyl)benzo[d]thiazol-2-yl)methyl)-3,4-dihydrothieno[3,4-d]pyridazin-1-yl)acetoxy)propanoate (Compound 40)

40

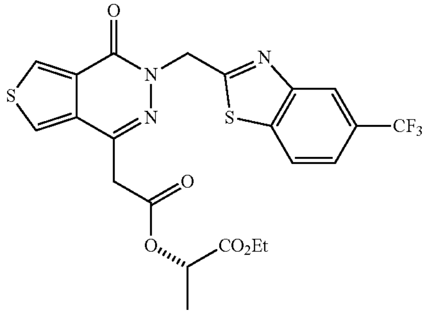

To a solution of Compound 22 (0.200 g, $4.71\times10^{-4}$ mol) in DMF (4.0 mL) was added CDI (0.092 g, $5.65\times10^{-4}$ mol). The reaction mixture was stirred at ambient temperature for 1 h before ethyl L-(−)-lactate (74 μL, $6.59\times10^{-4}$ mol) and DMAP (29 mg, $2.35\times10^{-4}$ mol) were added. The resulting reaction mixture was warmed to 40° C. and stirred overnight. Cooled the reaction mixture to ambient temperature and partitioned between diethyl ether and water, the layers separated, and the ethereal layer washed sequentially with water (1×), saturated aqueous $NaHCO_3$ (1×), water (1×), 1.0M $HCl_{(aq)}$ (1×), and brine (1×). The ethereal layer was dried over $Na_2SO_4$, filtered, and concentrated in vacuo. The obtained residue was purified via flash chromatography over silica gel (monitored by thin layer chromatography) and eluted with 2:1 (v/v) hexanes:ethyl acetate to 1:1 (v/v) hexanes:ethyl acetate. Evaporation of the collected fractions yielded 0.059 g (24% yield) of ethyl (S)-2-(2-(4-oxo-3-((5-(trifluoromethyl)benzo[d]thiazol-2-yl)methyl)-3,4-dihydrothieno[3,4-d]pyridazin-1-yl)acetoxy)propanoate (Compound 40): $^1H$ NMR ($CDCl_3$, 400 MHz): $\delta_{ppm}$ 8.45 (d, J=3.2 Hz, 1H), 8.29 (s, 1H), 7.95 (d, J=3.2 Hz, 1H), 7.92 (d, J=8.4 Hz, 1H), 7.60 (d, J=8.4 Hz, 1H), 5.75 (d, J=5.6 Hz, 2H), 5.11 (q, J=7.2 Hz, 1H), 4.17 (q, J=7.2 Hz, 2H), 3.97 (d, J=8.8 Hz, 2H), 1.48 (d, J=7.2 Hz, 3H), 1.23 (t, J=7.2 Hz, 3H); MS ESI (m/z) 526 $(M+1)^+$.

Example 20: Preparation of 2-(dimethylamino)ethyl 2-(4-oxo-3-((5-(trifluoromethyl)benzo[d]thiazol-2-yl)methyl)-3,4-dihydrothieno[3,4-d]pyridazin-1-yl)acetate (Compound 41)

41

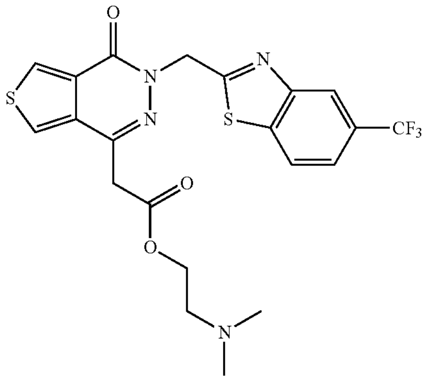

To a solution of Compound 22 (0.150 g, $3.53\times10^{-4}$ mol) in DMF (3.0 mL) was added CDI (63 mg, $3.88\times10^{-4}$ mol). The reaction mixture was stirred at ambient temperature for 1 h before 2-dimethylaminoethanol (42 μL, $4.24\times10^{-4}$ mol) was added. The resulting reaction mixture was stirred at ambient temperature overnight. The reaction mixture was partitioned between ether and saturated aqueous $NaHCO_3$, the layers separated, and the organic layer washed with saturated aqueous $NaHCO_3$ (1×) followed by water (2×). Subsequently, the organic layer was extracted with 1.0M $HCl_{(aq)}$ (2×) and the acidic aqueous layer combined and treated with solid $NaHCO_3$ until pH-9 reached. The now basic aqueous layer was extracted with EtOAc (2×) and the combined EtOAc layers washed with brine (1×), dried over $Na_2SO_4$, filtered, and concentrated in vacuo to yield 0.121 g (69% yield) of 2-(dimethylamino)ethyl 2-(4-oxo-3-((5-(trifluoromethyl)benzo[d]thiazol-2-yl)methyl)-3,4-dihydrothieno[3,4-d]pyridazin-1-yl)acetate (Compound 41): $^1H$ NMR ($CDCl_3$, 400 MHz): $\delta_{ppm}$ 8.43 (d, J=3.2 Hz, 1H), 8.28 (s, 1H), 7.92-7.90 (m, 2H), 7.58 (d, J=9.2 Hz, 1H), 5.73 (s, 2H), 4.21 (t, J=5.2 Hz, 2H), 3.89 (s, 2H), 2.50 (t, J=5.2 Hz, 2H), 2.19 (s, 6H); MS ESI (m/z) 497 $(M+1)^+$.

Example 21: Preparation of 2-((tert-butoxycarbonyl)amino)ethyl 2-(4-oxo-3-((5-(trifluoromethyl)benzo[d]thiazol-2-yl)methyl)-3,4-dihydrothieno[3,4-d]pyridazin-1-yl)acetate (Compound 42)

42

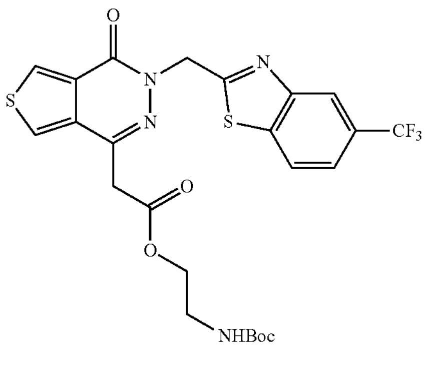

To a solution of Compound 22 (0.150 g, $3.53\times10^{-4}$ mol) in DMF (3.0 mL) was added CDI (63 mg, $3.88\times10^{-4}$ mol). The reaction mixture was stirred at ambient temperature for 1 h before N-Boc-ethanolamine (71 μL, $4.59\times10^{-4}$ mol) was added. The resulting reaction mixture was warmed to 50° C. and stirred overnight. Cooled the reaction mixture to ambient temperature and partitioned between diethyl ether and water, the layers separated, and the ethereal layer washed sequentially with water (1×), saturated aqueous $NaHCO_3$ (1×), water (1×), 1.0M $HCl_{(aq)}$ (1×), and brine (1×). The ethereal layer was dried over $Na_2SO_4$, filtered, and concentrated in vacuo. The obtained residue was purified via flash chromatography over silica gel (monitored by thin layer chromatography) and eluted with 2:1 (v/v) hexanes:ethyl acetate to 1:1 (v/v) hexanes:ethyl acetate. Evaporation of the collected fractions yielded 0.109 g (55% yield) of 2-((tert-butoxycarbonyl)amino)ethyl 2-(4-oxo-3-((5-(trifluoromethyl)benzo[d]thiazol-2-yl)methyl)-3,4-dihydrothieno[3,4-d]pyridazin-1-yl)acetate (Compound 42): $^1$H NMR ($CDCl_3$, 400 MHz): $\delta_{ppm}$ 8.47 (d, J=2.8 Hz, 1H), 8.29 (s, 1H), 7.95-7.92 (m, 2H), 7.60 (d, J=8.8 Hz, 1H), 5.75 (s, 2H), 4.20 (t, J=5.6 Hz, 2H), 3.90 (s, 2H), 3.39-3.36 (m, 2H), 1.43 (s, 9H); MS ESI (m/z) 569 $(M+1)^+$.

Example 22: Preparation of ethyl (S)-2-((tert-butoxycarbonyl)amino)-3-(4-(2-(4-oxo-3-((5-(trifluoromethyl)benzo[d]thiazol-2-yl)methyl)-3,4-dihydrothieno[3,4-d]pyridazin-1-yl)acetoxy)phenyl)propanoate (Compound 43)

43

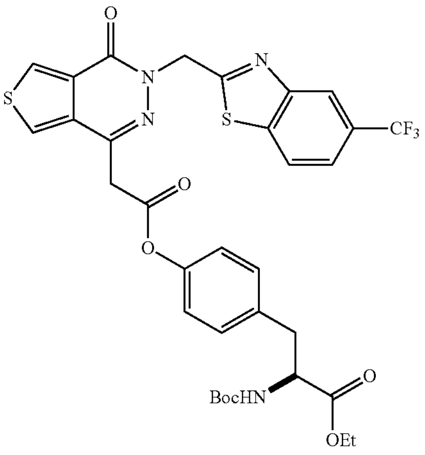

To a solution of Compound 22 (0.143 g, $3.36\times10^{-4}$ mol) in DMF (4.0 mL) was added CDI (0.065 g, $4.04\times10^{-4}$ mol). The reaction mixture was stirred at ambient temperature for 1 h before ethyl (tert-butoxycarbonyl)-L-tyrosinate (0.104 g, $3.36\times10^{-4}$ mol) and DMAP (21 mg, $1.68\times10^{-4}$ mol) were added. The resulting reaction mixture was warmed to 40° C. and stirred overnight. Cooled the reaction mixture to ambient temperature and partitioned between EtOAc and water, the layers separated, and the organic layer washed sequentially with water (1×), saturated aqueous $NaHCO_3$ (1×), water (1×), 1.0M $HCl_{(aq)}$ (1×), and brine (1×). The organic layer was dried over $Na_2SO_4$, filtered, and concentrated in vacuo. The obtained residue was purified via flash chromatography over silica gel (monitored by thin layer chromatography) and eluted with 1:1 (v/v) hexanes:ethyl acetate. Evaporation of the collected fractions yielded 0.079 g (33% yield) of ethyl (S)-2-((tert-butoxycarbonyl)amino)-3-(4-(2-(4-oxo-3-((5-(trifluoromethyl)benzo[d]thiazol-2-yl)methyl)-3,4-dihydrothieno[3,4-d]pyridazin-1-yl)acetoxy)phenyl)propanoate (Compound 43): $^1$H NMR ($CDCl_3$, 400 MHz): $\delta_{ppm}$ 8.50 (d, J=2.8 Hz, 1H), 8.29 (s, 1H), 7.92-7.90 (m, 2H), 7.60 (d, J=8.0 Hz, 1H), 7.11 (d, J=8.0 Hz, 2H), 6.96 (d, J=8.0 Hz, 2H), 5.78 (s, 2H), 4.98-4.96 (m, 1H), 4.54-4.52 (m, 1H), 4.14 (q, J=6.8 Hz, 2H), 4.10 (s, 2H), 3.08-3.03 (m, 2H), 1.41 (s, 9H), 1.22 (t, J=6.8 Hz, 3H); MS ESI (m/z) 717 $(M+1)^+$.

Example 23: Preparation of ethyl (S)-2-amino-3-(4-(2-(4-oxo-3-((5-(trifluoromethyl)benzo[d]thiazol-2-yl)methyl)-3,4-dihydrothieno[3,4-d]pyridazin-1-yl)acetoxy)phenyl)propanoate hydrochloride (Compound 44)

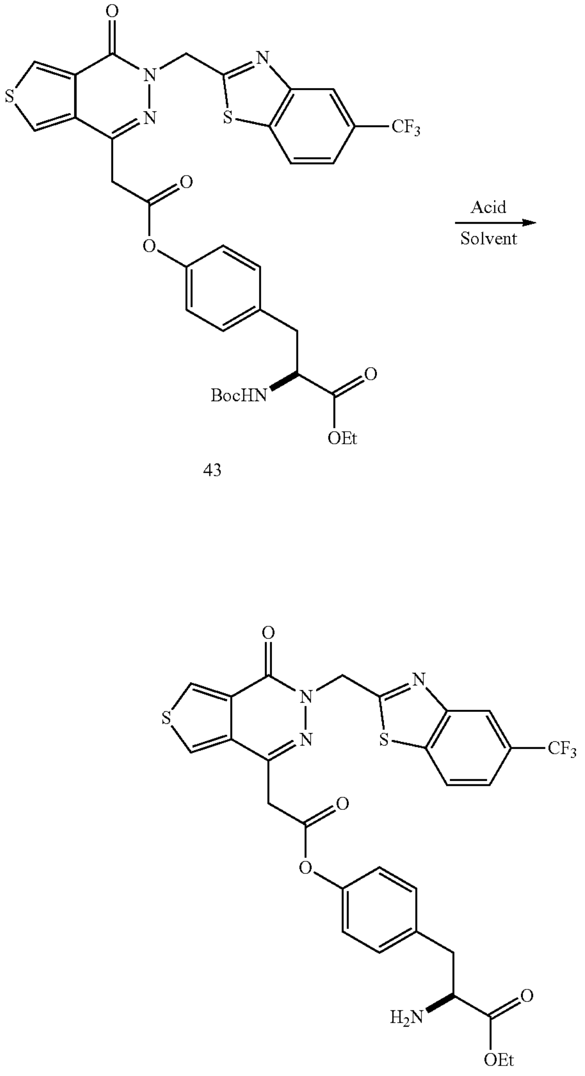

43

Acid = HCl, $H_2SO_4$, $H_3PO_4$, TFA
Solvent = ether, THF, dioxane. EtOAc

-continued

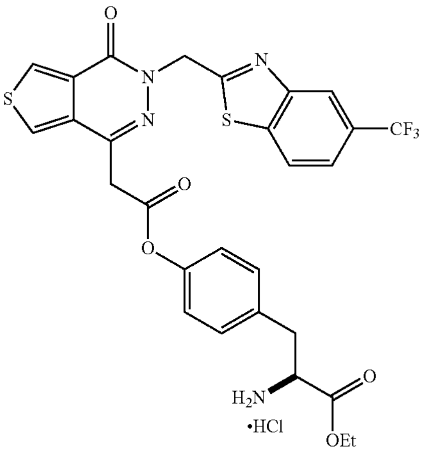

44

To a solution of Compound 43 (0.079 g, $1.10\times10^{-4}$ mol) in $CH_2Cl_2$ (1.5 mL) was added 2.0M HCl in ether (1.5 mL). The reaction mixture was stirred at ambient temperature overnight. Subsequently, the reaction mixture was diluted with ether and the precipitated white solid collected via vacuum filtration and washed with ether. The obtained solid was dried in vacuo to yield 0.053 g (74% yield) of ethyl (S)-2-amino-3-(4-(2-(4-oxo-3-((5-(trifluoromethyl)benzo[d]thiazol-2-yl)methyl)-3,4-dihydrothieno[3,4-d]pyridazin-1-yl)acetoxy)phenyl)propanoate hydrochloride (Compound 44): $^1H$ NMR ($D_2O$, 400 MHz): $\delta_{ppm}$ 8.54 (d, J=2.8 Hz, 1H), 8.26 (d, J=2.8 Hz, 1H), 8.00 (s, 1H), 7.79 (d, J=8.4 Hz, 1H), 7.49 (d, J=8.4 Hz, 1H), 7.02 (d, J=8.8 Hz, 2H), 6.79 (d, J=8.8 Hz, 2H), 5.69 (s, 2H), 4.28-4.13 (m, 5H), 3.12 (d, J=7.2 Hz, 2H), 1.11 (t, J=6.8 Hz, 3H); MS ESI (m/z) 617 $(M+1)^+$.

Example 24: Preparation of 2-aminoethyl 2-(4-oxo-3-((5-(trifluoromethyl)benzo[d]thiazol-2-yl)methyl)-3,4-dihydrothieno[3,4-d]pyridazin-1-yl)acetate hydrochloride (Compound 45)

-continued

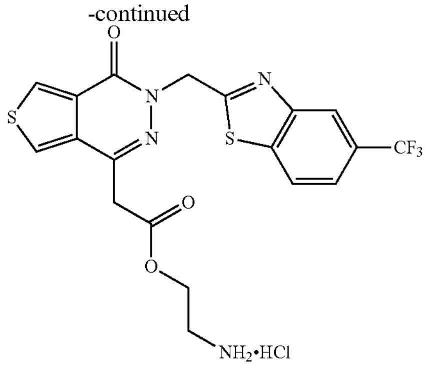

45

Acid = HCl, $H_2SO_4$, $H_3PO_4$, TFA
Solvent = ether, THF, dioxane. EtOAc

45

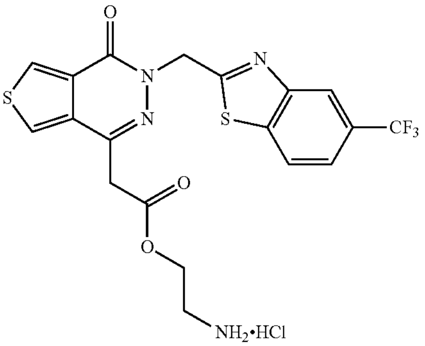

To a solution of Compound 42 (0.113 g, $1.99\times10^{-4}$ mol) in THF (2.0 mL) was added 4M HCl in dioxane (2.0 mL). The reaction mixture was stirred at ambient temperature for 1 hour. To the reaction mixture was added ether and the precipitated solid collected via vacuum filtration. The solid was washed with EtOAc and dried in vacuo to yield 0.089 g (89% yield) of 2-aminoethyl 2-(4-oxo-3-((5-(trifluoromethyl)benzo[d]thiazol-2-yl)methyl)-3,4-dihydrothieno[3,4-d]pyridazin-1-yl)acetate hydrochloride (Compound 45): $^1H$ NMR ($CD_3OD$, 400 MHz): $\delta_{ppm}$ 8.62 (d, J=3.2 Hz, 1H), 8.26 (d, J=3.2 Hz, 1H), 8.24 (s, 1H), 8.16 (d, J=8.8 Hz, 1H), 7.70 (d, J=8.8 Hz, 1H), 5.76 (s, 2H), 4.38 (t, J=4.8 Hz, 2H), 4.07 (s, 2H), 3.25 (t, J=4.8 Hz, 2H); MS ESI (m/z) 469 $(M+1)^+$.

Example 25: Preparation of methyl (2-(4-oxo-3-((5-(trifluoromethyl)benzo[d]thiazol-2-yl)methyl)-3,4-dihydrothieno[3,4-d]pyridazin-1-yl)acetyl)glycinate (Compound 46)

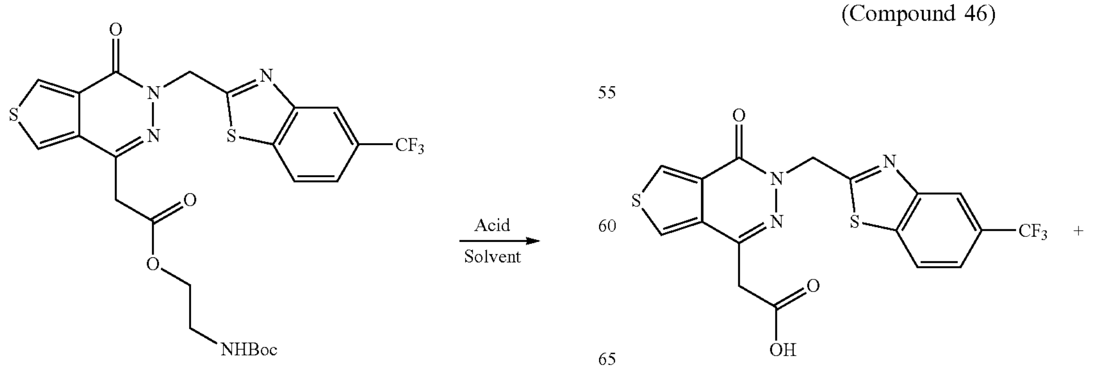

42

22

-continued

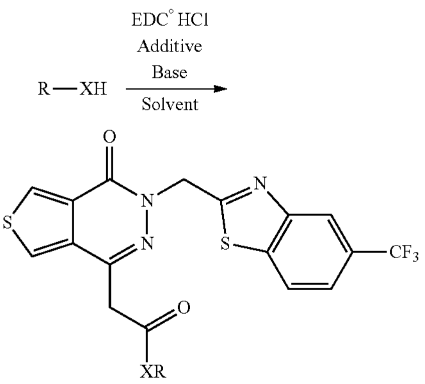

R =
X = O, NH, $NR^2$
Additive = none, N-Hyroxysuccinimide (NHS), 4-Dimethylaminopyridine (DMAP), Hydroxybenzotriazole (HOBT)
Base = triethylamine (TEA), diisopropylethylamine ($^iPr_2NEt$), pyridine
Solvent = dimethylformamide (DMF), 1-Methyl-2-pyrrolidinone, (NMP), tetrahydrofuran (THF)

46

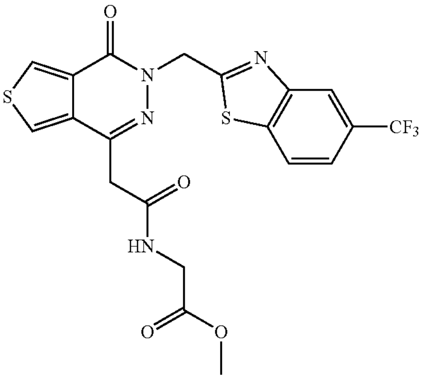

To a heterogeneous solution of Compound 22 (0.100 g, $2.35\times10^{-4}$ mol), EDC-HCl (59 mg, $3.06\times10^{-4}$ mol), NHS (35 mg, $3.06\times10^{-4}$ mol), and glycine methyl ester hydrochloride (38 mg, $3.06\times10^{-4}$ mol) in DMF (4.0 mL) was added TEA (0.130 mL, $9.41\times10^{-4}$ mol). The resulting homogeneous reaction mixture was stirred at ambient temperature overnight. Subsequently, the reaction mixture was partitioned between EtOAc and water, the layers separated, and the organic layer washed sequentially with water (1×), saturated aqueous $NaHCO_3$ (1×), water (1×), 1.0M $HCl_{(aq)}$ (1×), and brine (1×). The organic layer was dried over $Na_2SO_4$, filtered, and concentrated in vacuo. The obtained residue was purified via flash chromatography over silica gel (monitored by thin layer chromatography) and eluted with 2:1 (v/v) hexanes:ethyl acetate to 19:1 (v/v) $CH_2Cl_2$:methanol. Evaporation of the collected fractions yielded 0.028 g (24% yield) of methyl (2-(4-oxo-3-((5-(trifluoromethyl) benzo[d]thiazol-2-yl)methyl)-3,4-dihydrothieno[3,4-d] pyridazin-1-yl)acetyl)glycinate (Compound 46): $^1H$ NMR ($CDCl_3$, 400 MHz): $\delta_{ppm}$ 8.47 (d, J=2.8 Hz, 1H), 8.28 (s, 1H), 8.02 (d, J=2.8 Hz, 1H), 7.95 (d, J=8.0 Hz, 1H), 7.60 (d, J=8.0 Hz, 1H), 6.71 (br s, 1H), 5.77 (s, 2H), 4.00 (d, J=5.2 Hz, 2H), 3.84 (s, 2H), 3.68 (s, 3H); MS ESI (m/z) 497 $(M+1)^+$.

Example 26: Preparation of ethyl (2-(4-oxo-3-((5-(trifluoromethyl)benzo[d]thiazol-2-yl)methyl)-3,4-dihydrothieno[3,4-d]pyridazin-1-yl)acetyl)glycinate (Compound 47)

47

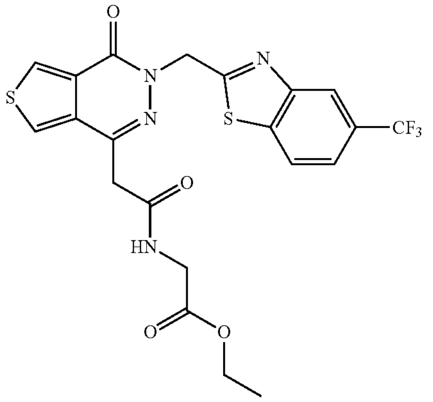

To a heterogeneous solution of Compound 22 (0.100 g, $2.35\times10^{-4}$ mol), EDC-HCl (59 mg, $3.06\times10^{-4}$ mol), NHS (35 mg, $3.06\times10^{-4}$ mol), and glycine ethyl ester hydrochloride (42 mg, $3.06\times10^{-4}$ mol) in DMF (4.0 mL) was added TEA (0.130 mL, $9.41\times10^{-4}$ mol). The resulting homogeneous reaction mixture was stirred at ambient temperature overnight. Subsequently, the reaction mixture was partitioned between EtOAc and water, the layers separated, and the organic layer washed sequentially with water (1×), saturated aqueous $NaHCO_3$ (1×), water (1×), 1.0M $HCl_{(aq)}$ (1×), and brine (1×). The organic layer was dried over $Na_2SO_4$, filtered, and concentrated in vacuo. The obtained residue was purified via flash chromatography over silica gel (monitored by thin layer chromatography) and eluted with 19:1 (v/v) $CH_2Cl_2$:methanol. Evaporation of the collected fractions yielded a solid that was suspended in ether and collected via vacuum filtration. The collected solid was washed with ether and dried in vacuo to yield 0.018 g (15% yield) of ethyl (2-(4-oxo-3-((5-(trifluoromethyl)benzo[d]thiazol-2-yl)methyl)-3,4-dihydrothieno[3,4-d]pyridazin-1-yl) acetyl)glycinate (Compound 47): $^1H$ NMR ($CDCl_3$, 400 MHz): $\delta_{ppm}$ 8.46 (d, J=2.8 Hz, 1H), 8.28 (s, 1H), 8.02 (d, J=2.8 Hz, 1H), 7.95 (d, J=8.8 Hz, 1H), 7.60 (d, J=8.8 Hz, 1H), 6.69 (br s, 1H), 5.77 (s, 2H), 4.12 (q, J=6.8 Hz, 2H), 3.98 (d, J=4.8 Hz, 2H), 3.84 (s, 2H), 1.22 (t, J=6.8 Hz, 3H); MS ESI (m/z) 511 $(M+1)^+$.

Example 27: Preparation of isopropyl (2-(4-oxo-3-((5-(trifluoromethyl)benzo[d]thiazol-2-yl)methyl)-3,4-dihydrothieno[3,4-d]pyridazin-1-yl)acetyl)glycinate (Compound 48)

48

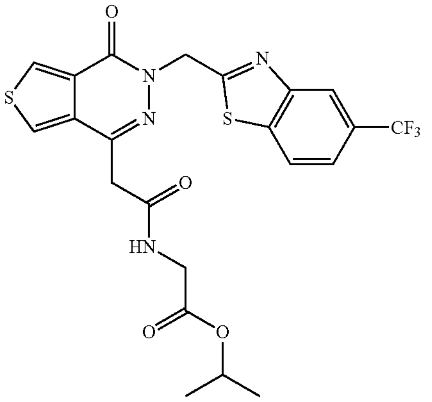

To a heterogeneous solution of Compound 22 (0.100 g, $2.35\times10^{-4}$ mol), EDC-HCl (59 mg, $3.06\times10^{-4}$ mol), NHS (35 mg, $3.06\times10^{-4}$ mol), and glycine isopropyl ester hydrochloride (47 mg, $3.06\times10^{-4}$ mol) in DMF (4.0 mL) was added TEA (0.130 mL, $9.41\times10^{-4}$ mol). The resulting homogeneous reaction mixture was stirred at ambient temperature overnight. Subsequently, the reaction mixture was partitioned between EtOAc and water, the layers separated, and the organic layer washed sequentially with water (1×), saturated aqueous $NaHCO_3$ (1×), water (1×), 1.0M $HCl_{(aq)}$ (1×), and brine (1×). The organic layer was dried over $Na_2SO_4$, filtered, and concentrated in vacuo. The obtained residue was purified via flash chromatography over silica gel (monitored by thin layer chromatography) and eluted with 1:1 (v/v) hexanes:ethyl acetate. Evaporation of the collected fractions yielded 0.021 g (17% yield) of isopropyl (2-(4-oxo-3-((5-(trifluoromethyl)benzo[d]thiazol-2-yl)methyl)-3,4-dihydrothieno[3,4-d]pyridazin-1-yl)acetyl)glycinate (Compound 48): $^1H$ NMR ($CDCl_3$, 400 MHz): $\delta_{ppm}$ 8.46 (d, J=2.8 Hz, 1H), 8.29 (s, 1H), 8.03 (d, J=2.8 Hz, 1H), 7.94 (d, J=8.4 Hz, 1H), 7.60 (d, J=8.4 Hz, 1H), 6.66 (br s, 1H), 5.77 (s, 2H), 4.97 (sept, J=6.4 Hz, 1H), 3.94 (d, J=5.2 Hz, 2H), 3.84 (s, 2H), 1.19 (d, J=6.4 Hz, 6H); MS ESI (m/z) 525 $(M+1)^+$.

Example 28: Preparation of methyl (2-(4-oxo-3-((5-(trifluoromethyl)benzo[d]thiazol-2-yl)methyl)-3,4-dihydrothieno[3,4-d]pyridazin-1-yl)acetyl)-L-alaninate (Compound 49)

49

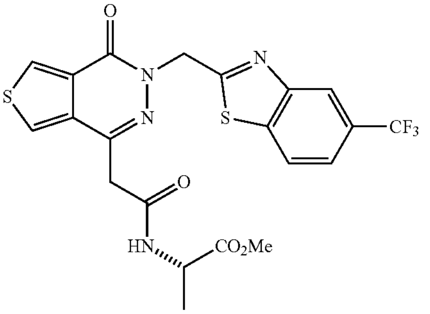

To a heterogeneous solution of Compound 22 (0.300 g, $7.06\times10^{-4}$ mol), EDC-HCl (0.176 g, $9.18\times10^{-4}$ mol), NHS (0.106 g, $9.18\times10^{-4}$ mol), and L-alanine methyl ester hydrochloride (0.128 g, $9.18\times10^{-4}$ mol) in DMF (10 mL) was added TEA (0.40 mL, $2.82\times10^{-3}$ mol). The resulting homogeneous reaction mixture was stirred at ambient temperature overnight. Subsequently, the reaction mixture was partitioned between EtOAc and water, the layers separated, and the organic layer washed sequentially with water (1×), saturated aqueous $NaHCO_3$ (1×), water (1×), 1.0M $HCl_{(aq)}$ (1×), and brine (1×). The organic layer was dried over $Na_2SO_4$, filtered, and concentrated in vacuo. The obtained residue was purified via flash chromatography over silica gel (monitored by thin layer chromatography) and eluted with 1:1 (v/v) hexanes:ethyl acetate. Evaporation of the collected fractions yielded 0.101 g (28% yield) of methyl (2-(4-oxo-3-((5-(trifluoromethyl)benzo[d]thiazol-2-yl)methyl)-3,4-dihydrothieno[3,4-d]pyridazin-1-yl)acetyl)-L-alaninate (Compound 49): $^1H$ NMR ($CDCl_3$, 400 MHz): $\delta_{ppm}$ 8.46 (d, J=3.2 Hz, 1H), 8.29 (s, 1H), 8.02 (d, J=3.2 Hz, 1H), 7.94 (d, J=8.0 Hz, 1H), 7.60 (d, J=8.0 Hz, 1H), 6.70 (br s, 1H), 5.77 (s, 2H), 4.52 (m, 1H), 3.80 (s, 2H), 3.65 (s, 3H), 1.32 (d, J=7.6 Hz, 3H); MS ESI (m/z) 511 $(M+1)^+$.

Example 29: Preparation of ethyl (2-(4-oxo-3-((5-(trifluoromethyl)benzo[d]thiazol-2-yl)methyl)-3,4-dihydrothieno[3,4-d]pyridazin-1-yl)acetyl)-L-alaninate (Compound 50)

50

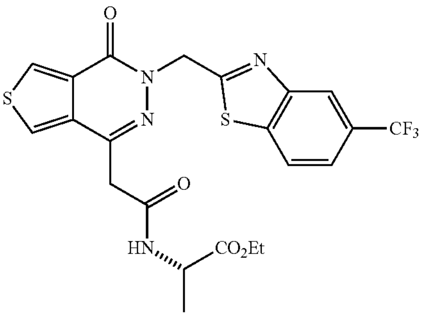

To a heterogeneous solution of Compound 22 (0.100 g, $2.35\times10^{-4}$ mol), EDC-HCl (59 mg, $3.06\times10^{-4}$ mol), NHS (35 mg, $3.06\times10^{-4}$ mol), and L-alanine ethyl ester hydrochloride (47 mg, $3.06\times10^{-4}$ mol) in DMF (4.0 mL) was added TEA (0.130 mL, $9.41\times10^{-4}$ mol). The resulting homogeneous reaction mixture was stirred at ambient temperature overnight. Subsequently, the reaction mixture was partitioned between EtOAc and water, the layers separated, and the organic layer washed sequentially with water (1×), saturated aqueous $NaHCO_3$ (1×), water (1×), 1.0M $HCl_{(aq)}$ (1×), and brine (1×). The organic layer was dried over $Na_2SO_4$, filtered, and concentrated in vacuo. The obtained residue was purified via flash chromatography over silica gel (monitored by thin layer chromatography) and eluted with 1:1 (v/v) hexanes:ethyl acetate. Evaporation of the collected fractions yielded a solid that was suspended in cold (0° C.) ether and collected via vacuum filtration. The collected solid was washed with cold (0° C.) ether and dried in vacuo to yield 0.037 g (30% yield) of ethyl (2-(4-oxo-3-((5-(trifluoromethyl)benzo[d]thiazol-2-yl)methyl)-3,4-dihydrothieno[3,4-d]pyridazin-1-yl)acetyl)-L-alaninate (Compound 50): $^1H$ NMR ($CDCl_3$, 400 MHz): $\delta_{ppm}$ 8.46 (d, J=2.8 Hz, 1H), 8.29 (s, 1H), 8.02 (d, J=2.8 Hz, 1H), 7.94 (d, J=8.4 Hz, 1H), 7.60 (d, J=8.4 Hz, 1H), 6.69 (br s, 1H), 5.77 (s, 2H), 4.49 (m, 1H), 4.09 (q, J=7.2 Hz, 2H), 3.80 (s, 2H), 1.31 (d, J=7.2 Hz, 3H), 1.20 (t, J=7.2 Hz, 3H); MS ESI (m/z) 525 $(M+1)^+$.

Example 30: Preparation of 2-(4-oxo-3-((5-(trifluoromethyl)benzo[d]thiazol-2-yl)methyl)-3,4-dihydrothieno[3,4-d]pyridazin-1-yl)acetamide (Compound 51)

51

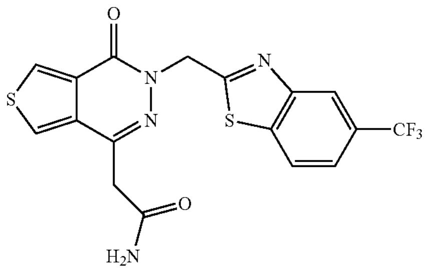

To a heterogeneous solution of Compound 22 (0.100 g, $2.35\times10^{-4}$ mol), EDC-HCl (59 mg, $3.06\times10^{-4}$ mol), NHS (35 mg, $3.06\times10^{-4}$ mol), and ammonium acetate (24 mg, $3.06\times10^{-4}$ mol) in DMF (3.0 mL) was added TEA (0.160 mL, $1.18\times10^{-3}$ mol). The resulting homogeneous reaction mixture was stirred at ambient temperature overnight. Subsequently, the reaction mixture was partitioned between EtOAc and water, the layers separated, and the organic layer washed sequentially with water (1×), saturated aqueous $NaHCO_3$ (1×), water (1×), 1.0M $HCl_{(aq)}$ (1×), and brine (1×). The organic layer was dried over $Na_2SO_4$, filtered, and concentrated in vacuo. The obtained residue was purified via flash chromatography over silica gel (monitored by thin layer chromatography) and eluted with 19:1 (v/v) $CH_2Cl_2$: methanol. Evaporation of the collected fractions yielded 0.071 g (71% yield) of 2-(4-oxo-3-((5-(trifluoromethyl)benzo[d]thiazol-2-yl)methyl)-3,4-dihydrothieno[3,4-d]pyridazin-1-yl)acetamide (Compound 51): $^1H$ NMR ($CD_3OD$, 400 MHz): $\delta_{ppm}$ 8.58 (d, J=2.8 Hz, 1H), 8.26 (d, J=2.8 Hz, 1H), 8.23 (s, 1H), 8.15 (d, J=8.4 Hz, 1H), 7.68 (d, J=8.4 Hz, 1H), 5.77 (s, 2H), 3.82 (s, 2H); MS ESI (m/z) 425 $(M+1)^+$.

Example 31: Preparation of tert-butyl (S)-2-((tert-butoxycarbonyl)amino)-3-(4-(2-(4-oxo-3-((5-(trifluoromethyl)benzo[d]thiazol-2-yl)methyl)-3,4-dihydrothieno[3,4-d]pyridazin-1-yl)acetoxy)phenyl)propanoate (Compound 52)

52

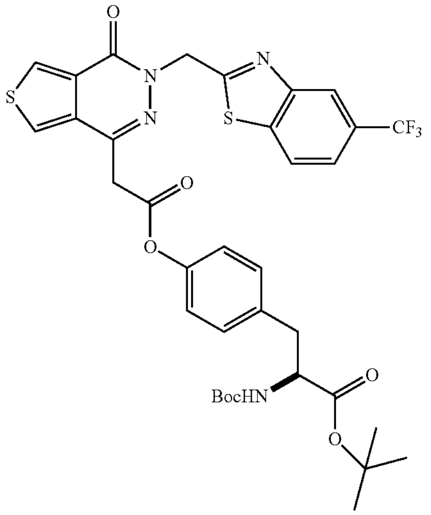

To a heterogeneous solution of Compound 22 (0.100 g, $2.35\times10^{-4}$ mol), EDC-HCl (59 mg, $3.06\times10^{-4}$ mol), NHS (35 mg, $3.06\times10^{-4}$ mol), and tert-butyl (tert-butoxycarbonyl)-L-tyrosinate (0.103 g, $3.06\times10^{-4}$ mol) in DMF (4.0 mL) was added TEA (0.130 mL, $9.41\times10^{-4}$ mol). The resulting homogeneous reaction mixture was stirred at ambient temperature overnight. Subsequently, the reaction mixture was partitioned between EtOAc and water, the layers separated, and the organic layer washed sequentially with water (1×), saturated aqueous $NaHCO_3$ (1×), water (1×), 1.0M $HCl_{(aq)}$ (1×), and brine (1×). The organic layer was dried over $Na_2SO_4$, filtered, and concentrated in vacuo. The obtained residue was purified via flash chromatography over silica gel (monitored by thin layer chromatography) and eluted with 4:1 (v/v) hexanes:ethyl acetate to 1:1 (v/v) hexanes:ethyl acetate. Evaporation of the collected fractions yielded 0.049 g (28% yield) of tert-butyl (S)-2-((tert-butoxycarbonyl)amino)-3-(4-(2-(4-oxo-3-((5-(trifluoromethyl)benzo[d]thiazol-2-yl)methyl)-3,4-dihydrothieno[3,4-d]pyridazin-1-yl)acetoxy)phenyl)propanoate (Compound 52): $^1H$ NMR ($CDCl_3$, 400 MHz): $\delta_{ppm}$ 8.50 (d, J=3.2 Hz, 1H), 8.28 (s, 1H), 7.92-7.90 (m, 2H), 7.59 (d, J=8.8 Hz, 1H), 7.14 (d, J=8.4 Hz, 2H), 6.96 (d, J=8.4 Hz, 2H), 5.78 (s, 2H), 4.98-4.96 (m, 1H), 4.48-4.41 (m, 1H), 4.10 (s, 2H), 3.06-3.01 (m, 2H), 1.41 (s, 9H), 1.38 (s, 9H); MS ESI (m/z) 745 $(M+1)^+$.

Example 32: Preparation of (S)-2-amino-3-(4-(2-(4-oxo-3-((5-(trifluoromethyl)benzo[d]thiazol-2-yl)methyl)-3,4-dihydrothieno[3,4-d]pyridazin-1-yl)acetoxy)phenyl)propanoic acid hydrochloride (Compound 53)

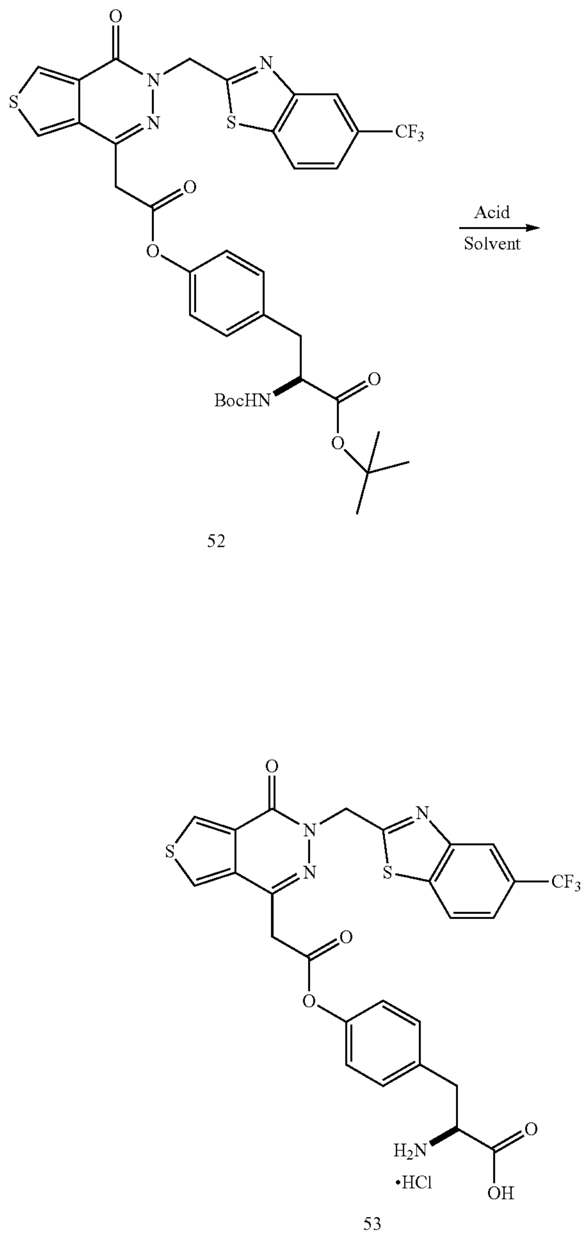

52

53

Acid = HCl, $H_2SO_4$, $H_3PO_4$, TFA
Solvent = ether, THF, dioxane. EtOAc

-continued

53

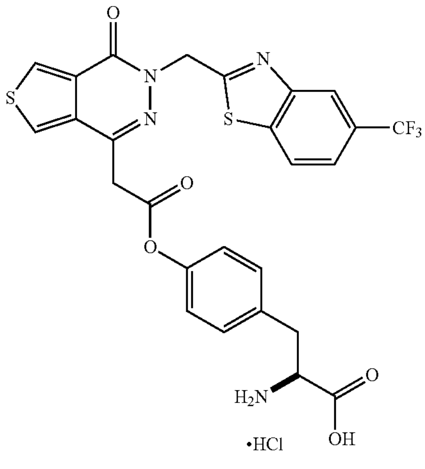

To a solution of Compound 52 (0.049 g, $6.58\times10^{-5}$ mol) in $CH_2Cl_2$ (1.5 mL) was added 4.0M HCl in dioxane (1.5 mL). The reaction mixture was stirred at ambient temperature overnight. Subsequently, the reaction mixture was concentrated in vacuo and the obtained white solid suspended in diethyl ether. The white solid was collected via vacuum filtration, washed with ether, and dried under vacuum to yield 0.032 g (78% yield) of (S)-2-amino-3-(4-(2-(4-oxo-3-((5-(trifluoromethyl)benzo[d]thiazol-2-yl)methyl)-3,4-dihydrothieno[3,4-d]pyridazin-1-yl)acetoxy)phenyl)propanoic acid hydrochloride (Compound 53): MS ESI (m/z) 589 $(M+1)^+$.

Example 33: Preparation of (2-(4-oxo-3-((5-(trifluoromethyl)benzo[d]thiazol-2-yl)methyl)-3,4-dihydrothieno[3,4-d]pyridazin-1-yl)acetyl)glycine (Compound 54)

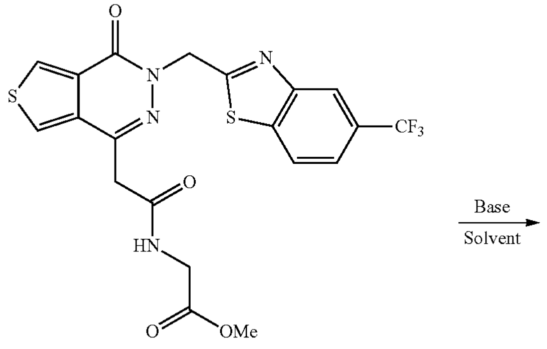

46

-continued

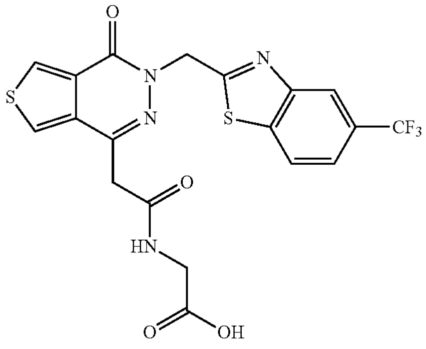

54

Base = NaOH, LiOH, KOH
Solvent = water, MeOH, EtOH, $^{i}$PrOH, THF

54

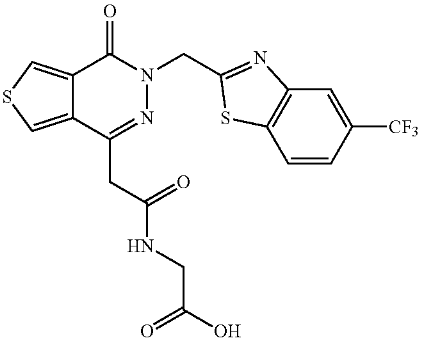

To a heterogeneous mixture of Compound 46 (0.096 g, $1.94 \times 10^{-4}$ mol) in MeOH (1.5 mL) was added 1.0M NaOH $_{(aq)}$ (0.5 mL). The reaction mixture was stirred at ambient temperature overnight. The resulting homogeneous reaction mixture was partitioned between ether and water, the layers separated, and the aqueous layer washed with ether (2×). The basic aqueous layer was acidified to a pH-2 by addition of 1.0M $HCl_{(aq)}$. The acidic aqueous layer was extracted with EtOAc (3×) and the organic layer washed with brine (1×) then dried over $Na_2SO_4$, filtered, and concentrated in vacuo. The obtained solid was suspended in ether and stirred for 5 minutes. The solid was collected via vacuum filtration and washed with ether. The obtained solid was dried under vacuum to yield 0.069 g (75% yield) of (2-(4-oxo-3-((5-(trifluoromethyl)benzo[d]thiazol-2-yl)methyl)-3,4-dihydrothieno[3,4-d]pyridazin-1-yl)acetyl)glycine (Compound 54): $^{1}H$ NMR ($CD_3OD$, 400 MHz): $\delta_{ppm}$ 8.56 (d, J=3.2 Hz, 1H), 8.34 (d, J=3.2 Hz, 1H), 8.23 (s, 1H), 8.16 (d, J=8.8 Hz, 1H), 7.68 (d, J=8.8 Hz, 1H), 5.77 (s, 2H), 3.92 (s, 2H), 3.90 (s, 2H); MS ESI (m/z) 483 $(M+1)^+$.

Example 34: Preparation of (2-(4-oxo-3-((5-(trifluoromethyl)benzo[d]thiazol-2-yl)methyl)-3,4-dihydrothieno[3,4-d]pyridazin-1-yl)acetyl)-L-alanine (Compound 55)

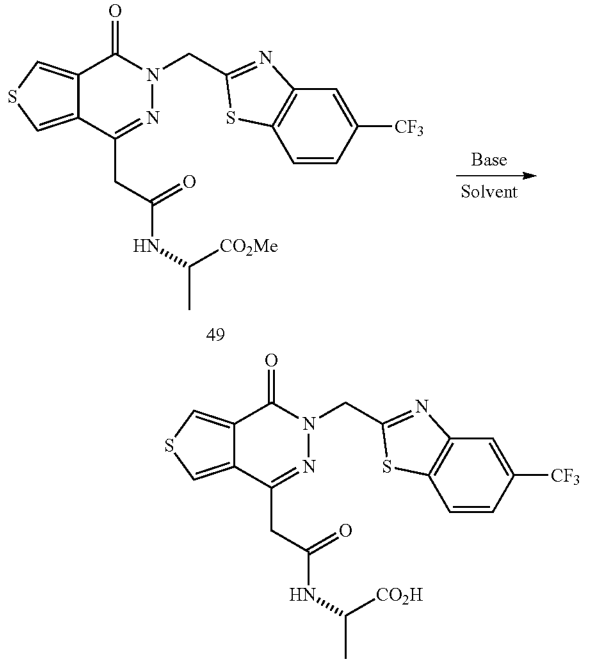

49

55

Base = NaOH, LiOH, KOH
Solvent = water, MeOH, EtOH, $^{i}$PrOH, THF

55

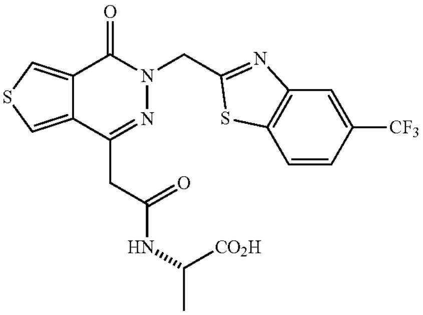

To a heterogeneous mixture of Compound 49 (0.101 g, $1.98 \times 10^{-4}$ mol) in MeOH (1.5 mL) was added 1.0M NaOH $_{(aq)}$ (0.5 mL). The reaction mixture was stirred at ambient temperature overnight. The resulting homogeneous reaction mixture was partitioned between ether and water, the layers separated, and the aqueous layer washed with ether (2×). The basic aqueous layer was acidified to a pH-2 by addition of 1.0M $HCl_{(aq)}$. The acidic aqueous layer was extracted with EtOAc (3×) and the organic layer washed with brine (1×) then dried over $Na_2SO_4$, filtered, and concentrated in vacuo. The obtained solid was suspended in ether and stirred for 5 minutes. The solid was collected via vacuum filtration and washed with ether. The obtained solid was dried under vacuum to yield 0.085 g (87% yield) of (2-(4-oxo-3-((5-(trifluoromethyl)benzo[d]thiazol-2-yl)methyl)-3,4-dihydrothieno[3,4-d]pyridazin-1-yl)acetyl)-L-alanine (Compound 55): $^{1}H$ NMR ($CDCl_3$, 400 MHz): $\delta_{ppm}$ 8.47 (d, J=2.8

Hz, 1H), 8.27 (s, 1H), 8.00 (d, J=2.8 Hz, 1H), 7.94 (d, J=8.8 Hz, 1H), 7.60 (d, J=8.8 Hz, 1H), 6.87-6.84 (br s, 1H), 5.77 (s, 2H), 4.57-4.52 (m, 1H), 3.82 (s, 2H), 1.37 (d, J=7.2 Hz, 3H); MS ESI (m/z) 497 $(M+1)^+$.

Example 35: Characterization of Aldose Reductase Inhibitor Compounds

The compounds are characterized in terms of physical characteristics (solubility and Log D).

Equilibrium Solubility in Phosphate Buffer, pH 7.4: The equilibrium solubility of test articles are measured in pH 7.4 aqueous buffers. The pH 7.4 buffer is prepared by combining 50 mL of 0.2 M $KH_2PO_4$ with 150 mL of $H_2O$, and then adjusting to pH 7.4 with 10 N NaOH. At least 1 mg of powder for each test article is combined with 1 mL of buffer to make a ≥1 mg/mL mixture. These samples are shaken on a Thermomixer® overnight at room temperature. The samples are then centrifuged for 10 minutes at 10,000 rpm The supernatant is sampled and diluted in duplicate 10-fold, 100-fold, and 10,000-fold into a mixture of 1:1 buffer: acetonitrile (ACN) prior to analysis. All samples are assayed by LC-MS/MS using electrospray ionization against standards prepared in a mixture of 1:1 assay buffer:ACN. Standard concentrations ranged from 1.0 μM to 1.0 nM.

Octanol/buffer partition coefficient (Log D) at pH 7.4: The octanol/buffer partition coefficient of three test articles are measured at pH 7.4. The pH 7.4 buffer is prepared by combining 50 mL of 0.2 M solution of $KH_2PO_4$ with 150 mL of dH2O, and then adjusting to pH 7.4 with 10 N NaOH. In a single incubation, 15 μL of a 10 mM DMSO solution of each test article (100 μM) is added to test tubes which contained 0.75 mL of octanol and 0.75 mL of pH 7.4 phosphate buffer. Testosterone is also introduced to each tube as an internal control, also at a dosing concentration of 100 μM. These samples are gently mixed on a benchtop rotator for 1 hour at room temperature. The tubes are then removed from the rotator and the aqueous and organic phases are allowed to separate for 1 hour. An aliquot of the organic layer is taken and diluted 200-fold into a mixture of 1:1 buffer: acetonitrile (ACN). An aliquot of the aqueous layer is taken and diluted 2-fold, 10-fold, and 200-fold into a mixture of 1:1 buffer:ACN. All samples are assayed by LC-MS/MS using electrospray ionization. Testosterone is utilized as a positive control (with a published/known Log D of 3.0-3.4).

Example 36: In Vitro Studies: Aldose Reductase Enzymatic Inhibition

The compounds are characterized in terms of biochemical characteristics, such as ability to inhibit Aldose Reductase enzymatic activity in vitro. The reductase activity of the compounds of the invention are spectrophotometrically assayed by following the decrease of NADPH at 25° C. for 4 min as described in Sato, S. (1992), "Rat kidney aldose reductase and aldehyde reductase and polyolproduction in rat kidney" *Am. J Physiol.* 263, F799.F805, incorporated by reference herein in its entirety.

The reaction mixture (total volume 1 ml) contains 0.1 mM NADPH, 100 mM substrate (DL-glyceraldehyde or L-xylose) and human recombinant aldose reductase (100 mU) in 0.1 M phosphate buffer, pH 6.2. Experiments are carried out in a microplate assay for AR inhibition using D-Glyceraldehyde and NADPH and the absorbance changes are monitored at 340 nm and % inhibition is calculated for ARIs at concentrations ranging from 0.1 nM to 100 μM. The reaction is started by adding the substrate (glyceraldehyde or xylose) as well as the same reaction mixture in which the substrate replaced by deionized water is used as a control. One enzyme unit (U) is defined as the activity consuming 1 μmole of NADPH per min at 25° C. The enzymatic inhibition assay is performed as described in WO 2012/009553, which is hereby incorporated by reference in its entirety.

Example 37: Ex Vivo Studies

Rat studies are performed with the approval of the Institutional Animal Care and Use Committee at Columbia University, New York. This investigation conforms to the *Guide for the Care and Use of Laboratory Animals* published by the US National Institutes of Health (NIH publication No. 85-23, 1996; hereby incorporated by reference in its entirety).

Experiments are performed using an isovolumic isolated rat heart preparation as described by Hwang Y C, Sato S, Tsai J Y, Yan S, Bakr S, Zhang H, Oates P J, Ramasamy R (2002), "Aldose reductase activation is a key component of myocardial response to ischemia," *Faseb J* 16, 243-245 and Ramasamy R, Hwang Y C, Whang J, Bergmann S R (2001), "Protection of ischemic hearts by high glucose is mediated, in part, by GLUT-4, *" American Journal of Physiology.* 281, H290-297; each of which hereby incorporated by reference in its entirety.

Male Wistar rats (300.350 g, 3 to 4 months old) are anesthetized with a mixture of ketamine (80 mg/kg) and xylazine (10 mg/kg). After deep anesthesia is achieved, hearts are rapidly excised, placed into iced saline, and retrogradely perfused at 37° C. in a non-recirculating mode through the aorta at a rate of 12.5 ml/min. Hearts are perfused with modified Krebs-Henseleit buffer containing (in mM) NaCl 118, KCl 4.7, $CaCl_2$) 2.5, $MgCl_2$ 1.2, $NaHCO_3$ 25, glucose 5, palmitate 0.4, bovine serum albumin 0.4, and 70 mU/L insulin. The perfusate is equilibrated with a mixture of 95% 02-5% $CO_2$, which maintains perfusate $PO_2$>600 mmHg. Left ventricular developed pressure (LVDP) and left ventricular end diastolic pressure (LVEDP) are measured using a latex balloon in the left ventricle. LVDP, heart rate, and coronary perfusion pressure are monitored continuously on an ADI recorder. All rat hearts are subjected to 20 min of zero-flow ischemia and 60 min of reperfusion (I/R).

In studies involving the use of aldose reductase inhibitor, hearts are perfused with modified Krebs-Henseleit buffer containing a compound of the invention, at a final concentration of 100 nM, 10 min prior to ischemia and is continued throughout the perfusion protocol. Creatine kinase (CK) release, a marker of myocardial I/R injury, is measured as described by Hwang Y C, Sato S, Tsai J Y, Yan S, Bakr S, Zhang H, Oates P J, Ramasamy R (2002), "Aldose reductase activation is a key component of myocardial response to ischemia," *Faseb J.* 16, 243-245 and Ramasamy R, Hwang Y C, Whang J, Bergmann S R (2001), "Protection of ischemic hearts by high glucose is mediated, in part, by GLUT-4, *" American Journal of Physiology.* 281, H290-297; each of which hereby incorporated by reference in its entirety.

Isolated perfused hearts are subjected to ischemia reperfusion (1/R) injury and the measures of cardiac injury and cardiac function are monitored. Creatine kinase (CK) release during reperfusion, a marker of cardiac ischemic injury, is measured in rat hearts treated with a compound of the invention and in untreated hearts. Left ventricular developed pressure (LVDP) is measured in rat hearts treated with a compound of the invention and in untreated hearts after I/R.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways within the scope and spirit of the invention.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

What is claimed is:

1. A compound of Formula (I-4)

(I-4)

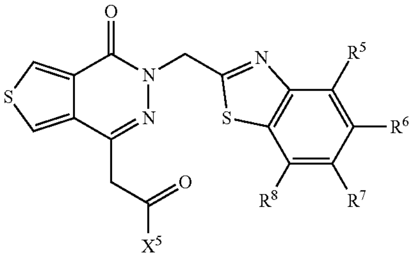

wherein, $R^5$ through $R^8$ are independently hydrogen, halogen, or haloalkyl $X^5$ is Q-$R^{10}$;

Q is O, NH, O—($C_1$-$C_6$)-alkyl, O—($C_1$-$C_6$)-hydroxyalkyl, O—($C_1$-$C_6$)-aminoalkyl, O-aryl, O-heteroaryl, O-biaryl, O-benzyl, NH—($C_1$-$C_6$)-alkyl, NH—($C_1$-$C_6$)-hydroxyalkyl, NH—($C_1$-$C_6$)-aminoalkyl, NH-aryl, NH-heteroaryl, NH-biaryl, NH-benzyl, or a bond;

$R^{10}$ is

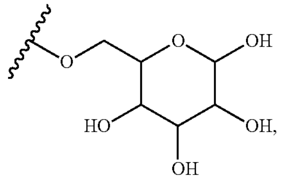

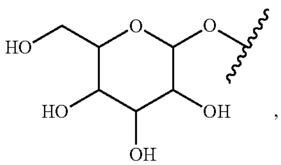

,

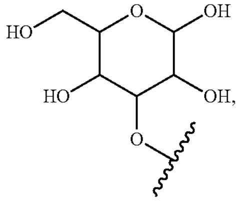

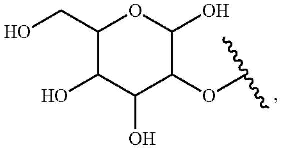

,

-continued

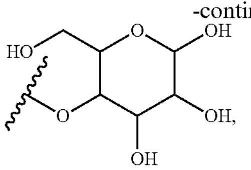

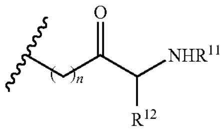

,

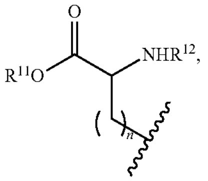

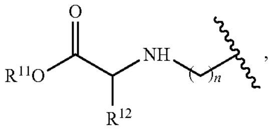

,

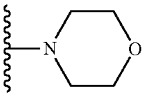

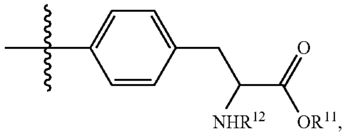

aryl, heteroaryl, biaryl, benzyl, heterocycle, or C(O)$OR^{11}$, with the proviso that when Q is not a bond, $R^{10}$ can be bonded to any substitutable atom in Q, and when Q is NH, $R^{10}$ can also be H or OH; and $R^{11}$ and $R^{12}$ are independently H or ($C_1$-$C_6$)-alkyl optionally substituted with one or more substituents selected from the group consisting of $OR^{13}$, $NHR^{13}$, $SR^{13}$, $CO_2R^{13}$, $CONHR^{13}$, aryl, hydroxyaryl, indolyl, imidazolyl, and $NH(CNH)NH_2$;

or $R^{11}$ and $R^{12}$, taken together with the atoms to which they are attached, form a 3-7 membered heterocyclic ring;

$R^{13}$ is H or ($C_1$-$C_6$)-alkyl; and n is 0, 1, or 2;

or a pharmaceutically acceptable salt thereof.

2. The compound of claim 1, wherein $X^5$ is selected from a group consisting of

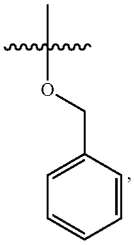

,

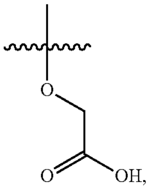

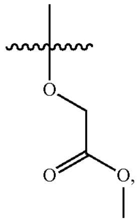

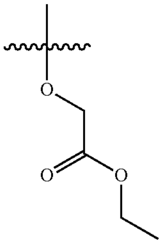

,

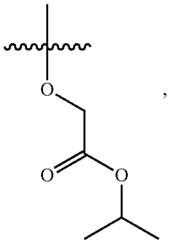

,

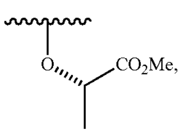

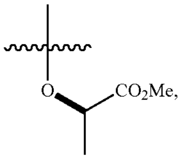

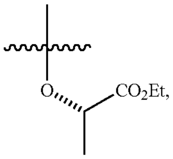

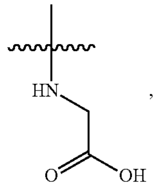

,

-continued

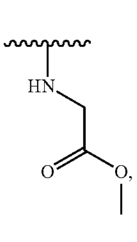
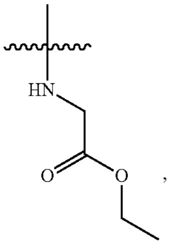
,
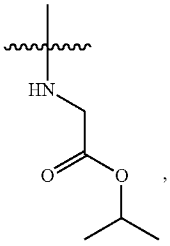
,

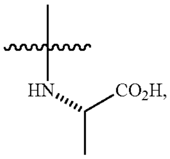
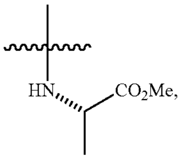
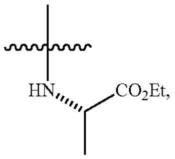

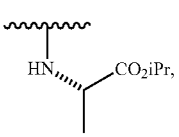
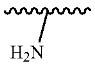
,
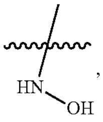
,

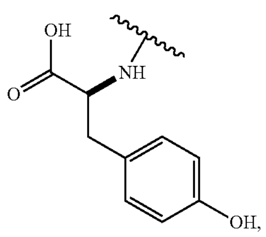
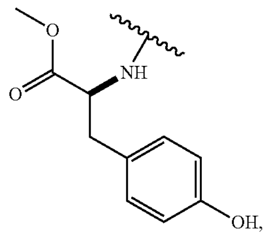

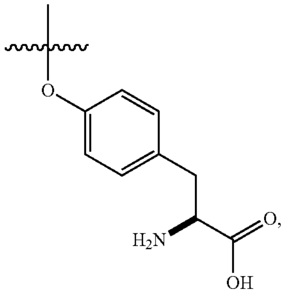
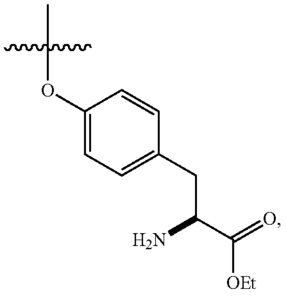

-continued

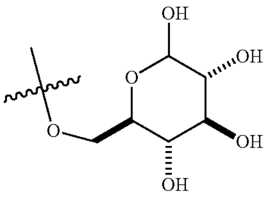
and
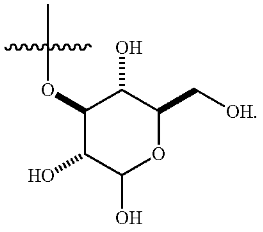

3. The compound of claim 1, wherein $R^5$, $R^7$ and $R^8$ are each H; and $R^6$ is halogen or haloalkyl.

4. The compound of claim 3, wherein $R^6$ is trifluoromethyl.

5. A pharmaceutical composition comprising a compound of claim 1 and a pharmaceutically acceptable carrier.

6. The compound of claim 1, wherein the compound is selected from the group consisting of

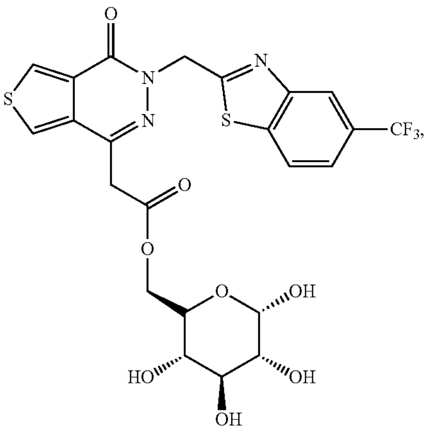

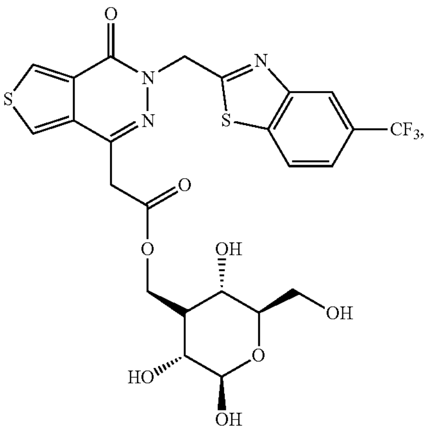

-continued
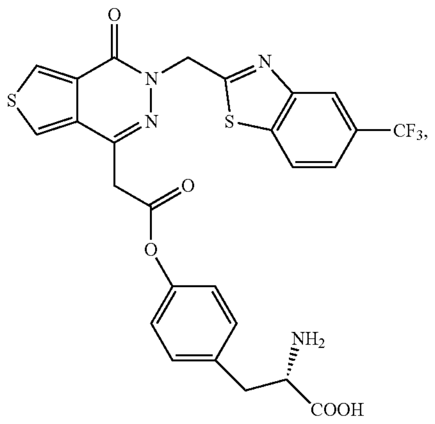
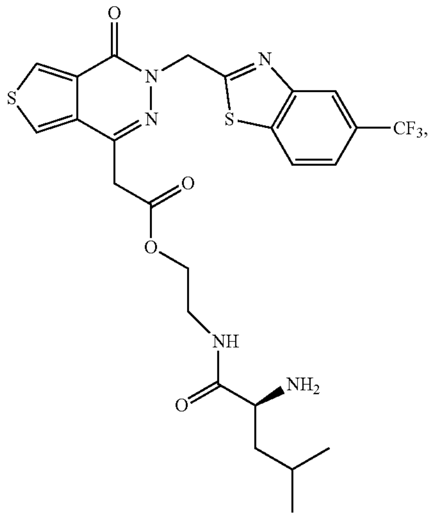
-continued
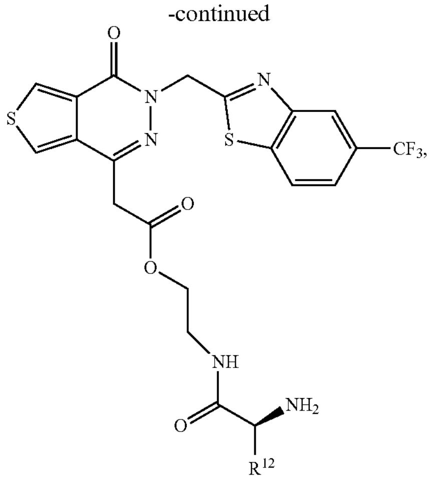
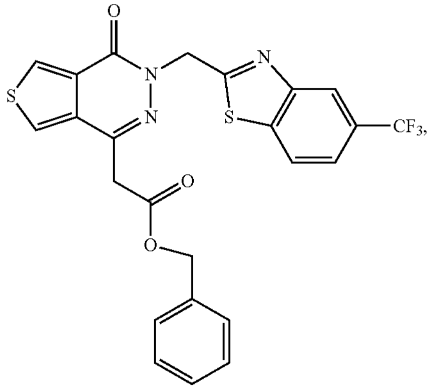
and pharmaceutically acceptable salts thereof, wherein $R^{12}$ is H or ($C_1$-$C_6$)-alkyl optionally substituted with one or more substituents selected from the group consisting of $OR^{13}$, $NHR^{13}$, $SR^{13}$, $CO_2R^{13}$, $CONHR^{13}$, aryl, hydroxyaryl, indolyl, imidazolyl, and $NH(CNH)NH_2$, and wherein $R^{13}$ is H or ($C_1$-$C_6$)-alkyl.
* * * * *